US012624098B2

(12) United States Patent
    Osborne et al.

(10) Patent No.: US 12,624,098 B2
(45) Date of Patent:    May 12, 2026

(54) TREATMENT OF AGE-RELATED MACULAR DEGENERATION AND DIABETIC MACULAR EDEMA BY ADMINISTRATION OF A BISPECIFIC ANTIBODY TO VEGF AND ANG-2

(71) Applicants: Hoffmann-La Roche Inc., Little Falls, NJ (US); Genentech, Inc., South San Francisco, CA (US)

(72) Inventors: Aaron Osborne, South San Francisco, CA (US); Jayashree Sahni, Basel (CH); Robert James Weikert, Basel (CH)

(73) Assignees: Hoffmann-La Roche Inc., Little Falls, NJ (US); Genentech, Inc., South San Francisco, CA (US)

( * ) Notice: Subject to any disclaimer, the term of this patent is extended or adjusted under 35 U.S.C. 154(b) by 0 days.

(21) Appl. No.: 18/166,996

(22) Filed: Feb. 9, 2023

(65) Prior Publication Data

US 2023/0416353 A1     Dec. 28, 2023

Related U.S. Application Data

(63) Continuation of application No. 16/985,477, filed on Aug. 5, 2020, now abandoned, which is a continuation of application No. PCT/EP2019/052704, filed on Feb. 5, 2019.

(60) Provisional application No. 62/729,333, filed on Sep. 10, 2018, provisional application No. 62/627,103, filed on Feb. 6, 2018.

(51) Int. Cl.
    *A61K 39/395*        (2006.01)
    *A61P 27/02*          (2006.01)
    *C07K 16/22*          (2006.01)
    *A61K 39/00*          (2006.01)

(52) U.S. Cl.
    CPC ............. *C07K 16/22* (2013.01); *A61P 27/02* (2018.01); *A61K 2039/505* (2013.01); *A61K 2039/545* (2013.01); *C07K 2317/31* (2013.01); *C07K 2317/565* (2013.01)

(58) Field of Classification Search
    None
    See application file for complete search history.

(56) References Cited

U.S. PATENT DOCUMENTS

| | | | |
|---|---|---|---|
| 4,275,149 A | 6/1981 | Litman et al. |
| 4,318,980 A | 3/1982 | Boguslaski et al. |
| 4,490,473 A | 12/1984 | Brunhouse |
| 4,676,980 A | 6/1987 | Segal et al. |
| 4,737,456 A | 4/1988 | Weng et al. |
| 4,752,601 A | 6/1988 | Hahn |
| 4,816,567 A | 3/1989 | Cabilly et al. |

| | | | |
|---|---|---|---|
| 5,047,335 A | 9/1991 | Paulson et al. |
| 5,091,178 A | 2/1992 | Hellstrom et al. |
| 5,202,238 A | 4/1993 | Fell et al. |
| 5,204,244 A | 4/1993 | Fell et al. |
| 5,208,020 A | 5/1993 | Chari et al. |
| 5,225,539 A | 7/1993 | Winter |
| 5,278,299 A | 1/1994 | Wong et al. |
| 5,348,876 A | 9/1994 | Michaelsen et al. |
| 5,412,468 A | 5/1995 | Lundberg et al. |
| 5,416,064 A | 5/1995 | Chari et al. |
| 5,419,904 A | 5/1995 | Irie et al. |
| 5,510,261 A | 4/1996 | Goochee et al. |
| 5,571,894 A | 11/1996 | Wels et al. |
| 5,576,184 A | 11/1996 | Better et al. |
| 5,587,458 A | 12/1996 | King et al. |
| 5,624,821 A | 4/1997 | Winter et al. |
| 5,635,483 A | 6/1997 | Pettit et al. |
| 5,648,237 A | 7/1997 | Carter et al. |
| 5,648,260 A | 7/1997 | Winter et al. |
| 5,698,449 A | 12/1997 | Baumann et al. |
| 5,712,374 A | 1/1998 | Kunstmann et al. |
| 5,714,586 A | 2/1998 | Kunstmann et al. |
| 5,730,977 A | 3/1998 | Ooka et al. |
| 5,731,168 A | 3/1998 | Carter et al. |
| 5,736,137 A | 4/1998 | Anderson et al. |
| 5,739,116 A | 4/1998 | Hamann et al. |
| 5,747,035 A | 5/1998 | Presta et al. |
| 5,750,373 A | 5/1998 | Garrard et al. |
| 5,767,285 A | 6/1998 | Hamann et al. |
| 5,770,429 A | 6/1998 | Lonberg et al. |
| 5,770,701 A | 6/1998 | McGahren et al. |
| 5,770,710 A | 6/1998 | McGahren et al. |
| 5,773,001 A | 6/1998 | Hamann et al. |

(Continued)

FOREIGN PATENT DOCUMENTS

| | | |
|---|---|---|
| CA | 2369292 | 10/2000 |
| CA | 2645891 A1 | 9/2007 |

(Continued)

OTHER PUBLICATIONS

Asahara et al., "Tie2 Receptor Ligands, Angiopoietin-1 and Angiopoietin-2, Modulate VEGF-Induced Postnatal Neovascularization" Circulation Research 83:233-240 ( 1998).

(Continued)

*Primary Examiner* — Christine J Saoud
(74) *Attorney, Agent, or Firm* — Jelena Libby

(57)        ABSTRACT

The current invention relates to the use of bispecific antibodies that bind to human vascular endothelial growth factor (VEGF) and to human angiopoietin-2 (ANG-2) for the treatment of ophthalmologic diseases, such as age-related macular degeneration and diabetic macular edema, where the bispecific antibodies are administered intravitreally every 8 weeks or less frequently.

19 Claims, 7 Drawing Sheets

Specification includes a Sequence Listing.

(56)                 References Cited

U.S. PATENT DOCUMENTS

| | | | |
|---|---|---|---|
| 5,780,588 A | 7/1998 | Pettit et al. |
| 5,789,199 A | 8/1998 | Joly et al. |
| 5,821,337 A | 10/1998 | Carter et al. |
| 5,834,597 A | 11/1998 | Tso et al. |
| 5,840,523 A | 11/1998 | Simmons et al. |
| 5,843,398 A | 12/1998 | Kaminski et al. |
| 5,859,205 A | 1/1999 | Adair et al. |
| 5,869,046 A | 2/1999 | Presta et al. |
| 5,877,296 A | 3/1999 | Hamann et al. |
| 5,885,573 A | 3/1999 | Bluestone et al. |
| 5,959,177 A | 9/1999 | Hein et al. |
| 5,985,599 A | 11/1999 | McKenzie et al. |
| 6,030,613 A | 2/2000 | Blumberg et al. |
| 6,040,498 A | 3/2000 | Stomp et al. |
| 6,054,297 A | 4/2000 | Carter et al. |
| 6,075,181 A | 6/2000 | Kucherlapati et al. |
| 6,086,875 A | 7/2000 | Blumberg et al. |
| 6,136,310 A | 10/2000 | Hanna et al. |
| 6,150,584 A | 11/2000 | Kucherlapati et al. |
| 6,165,464 A | 12/2000 | Hudziak et al. |
| 6,165,745 A | 12/2000 | Ward et al. |
| 6,166,185 A | 12/2000 | Davis et al. |
| 6,171,586 B1 | 1/2001 | Lam et al. |
| 6,172,213 B1 | 1/2001 | Lowman et al. |
| 6,180,377 B1 | 1/2001 | Morgan et al. |
| 6,194,551 B1 | 2/2001 | Idusogie et al. |
| 6,242,195 B1 | 6/2001 | Idusogie et al. |
| 6,248,516 B1 | 6/2001 | Winter et al. |
| 6,267,958 B1 | 7/2001 | Andya et al. |
| 6,277,375 B1 | 8/2001 | Ward |
| 6,323,321 B1 | 11/2001 | Buhring et al. |
| 6,417,429 B1 | 7/2002 | Hein et al. |
| 6,420,548 B1 | 7/2002 | Vezina et al. |
| 6,485,726 B1 | 11/2002 | Blumberg et al. |
| 6,491,916 B1 | 12/2002 | Bluestone et al. |
| 6,528,624 B1 | 3/2003 | Idusogie et al. |
| 6,538,124 B1 | 3/2003 | Idusogie et al. |
| 6,582,959 B2 | 6/2003 | Kim |
| 6,586,207 B2 | 7/2003 | Tirrell et al. |
| 6,630,579 B2 | 10/2003 | Chari et al. |
| 6,676,927 B1 | 1/2004 | Ravetch |
| 6,703,020 B1 | 3/2004 | Thorpe et al. |
| 6,706,265 B1 | 3/2004 | Bolt et al. |
| 6,737,056 B1 | 5/2004 | Presta et al. |
| 6,815,540 B1 | 11/2004 | Pluckthun et al. |
| 6,821,505 B2 | 11/2004 | Ward |
| 6,897,044 B1 | 5/2005 | Braslawsky et al. |
| 6,946,292 B2 | 9/2005 | Kanda et al. |
| 6,982,321 B2 | 1/2006 | Winter et al. |
| 7,041,870 B2 | 5/2006 | Tomizuka et al. |
| 7,060,269 B1 | 6/2006 | Baca et al. |
| 7,083,784 B2 | 8/2006 | Dall'Acqua et al. |
| 7,087,409 B2 | 8/2006 | Barbas et al. |
| 7,122,637 B2 | 10/2006 | Presta |
| 7,125,978 B1 | 10/2006 | Vezina et al. |
| 7,129,330 B1 | 10/2006 | Little et al. |
| 7,183,387 B1 | 2/2007 | Presta |
| 7,189,826 B2 | 3/2007 | Rodman |
| 7,214,775 B2 | 5/2007 | Hanai et al. |
| 7,276,585 B2 | 10/2007 | Lazar et al. |
| 7,297,775 B2 | 11/2007 | Idusogie et al. |
| 7,317,091 B2 | 1/2008 | Lazar et al. |
| 7,332,581 B2 | 2/2008 | Presta et al. |
| 7,335,742 B2 | 2/2008 | Presta |
| 7,364,731 B2 | 4/2008 | Idusogie et al. |
| 7,371,826 B2 | 5/2008 | Presta et al. |
| 7,416,727 B2 | 8/2008 | Presta |
| 7,498,298 B2 | 3/2009 | Doronina et al. |
| 7,521,053 B2 | 4/2009 | Oliner |
| 7,521,541 B2 | 4/2009 | Eigenbrot et al. |
| 7,527,791 B2 | 5/2009 | Adams et al. |
| 7,563,441 B2 | 7/2009 | Graus et al. |
| 7,598,055 B2 | 10/2009 | Bobrowicz et al. |
| 7,632,497 B2 | 12/2009 | Stavenhagen et al. |
| 7,658,924 B2 | 2/2010 | Oliner et al. |
| 7,678,373 B2 | 3/2010 | Desnoyers et al. |
| 7,691,977 B2 | 4/2010 | Fuh et al. |
| 7,741,072 B2 | 6/2010 | Idusogie et al. |
| 7,785,791 B2 | 8/2010 | Presta |
| 7,790,858 B2 | 9/2010 | Presta |
| 7,919,257 B2 | 4/2011 | Hoogenboom et al. |
| 7,923,538 B2 | 4/2011 | Shitara et al. |
| 7,931,895 B2 | 4/2011 | Beliard et al. |
| 7,960,512 B2 | 6/2011 | Stavenhagen et al. |
| 7,994,290 B2 | 8/2011 | Shitara et al. |
| 8,088,376 B2 | 1/2012 | Chamberlain et al. |
| 8,133,979 B2 | 3/2012 | Brinkmann et al. |
| 8,163,882 B2 | 4/2012 | Presta |
| RE43,568 E | 8/2012 | Graus et al. |
| 8,268,314 B2 | 9/2012 | Baehner et al. |
| 8,361,747 B2 | 1/2013 | Brinkmann et al. |
| 8,399,626 B2 | 3/2013 | Brinkmann et al. |
| RE44,359 E | 7/2013 | Graus et al. |
| 8,674,083 B2 | 3/2014 | Presta |
| 8,703,130 B2 | 4/2014 | Baehner et al. |
| 8,945,552 B2 | 2/2015 | Baehner et al. |
| 8,969,526 B2 | 3/2015 | Baehner et al. |
| 9,017,671 B2 | 4/2015 | Andya et al. |
| 9,695,233 B2 | 7/2017 | Duerr et al. |
| 9,708,396 B2 | 7/2017 | Baehner et al. |
| 10,683,345 B2 | 6/2020 | Duerr et al. |
| 2001/0036459 A1 | 11/2001 | Ravetch et al. |
| 2002/0098193 A1 | 7/2002 | Ward et al. |
| 2002/0197256 A1 | 12/2002 | Grewal et al. |
| 2003/0064053 A1 | 4/2003 | Liu et al. |
| 2003/0108546 A1 | 6/2003 | Fukushima et al. |
| 2003/0115614 A1 | 6/2003 | Kanda et al. |
| 2003/0118592 A1 | 6/2003 | Ledbetter et al. |
| 2003/0124129 A1 | 7/2003 | Oliner et al. |
| 2003/0158389 A1 | 8/2003 | Idusogie et al. |
| 2003/0161826 A1 | 8/2003 | Arnason et al. |
| 2003/0166868 A1 | 9/2003 | Presta et al. |
| 2003/0190311 A1 | 10/2003 | Dall'Acqua et al. |
| 2003/0190317 A1 | 10/2003 | Baca et al. |
| 2003/0203409 A1 | 10/2003 | Kim |
| 2003/0206899 A1 | 11/2003 | Ferrara et al. |
| 2004/0002587 A1 | 1/2004 | Watkins et al. |
| 2004/0110226 A1 | 6/2004 | Lazar et al. |
| 2004/0132101 A1 | 7/2004 | Lazar et al. |
| 2004/0191244 A1 | 9/2004 | Presta |
| 2004/0191256 A1 | 9/2004 | Raju |
| 2004/0191265 A1 | 9/2004 | Schenerman et al. |
| 2004/0214988 A1 | 10/2004 | Tirrell et al. |
| 2004/0228856 A1 | 11/2004 | Presta |
| 2005/0014934 A1 | 1/2005 | Hinton et al. |
| 2005/0031613 A1 | 2/2005 | Nakamura et al. |
| 2005/0031626 A1 | 2/2005 | Stevenson |
| 2005/0032114 A1 | 2/2005 | Hinton et al. |
| 2005/0037000 A1 | 2/2005 | Stavenhagen et al. |
| 2005/0054832 A1 | 3/2005 | Lazar et al. |
| 2005/0079170 A1 | 4/2005 | LeGall et al. |
| 2005/0079574 A1 | 4/2005 | Bond et al. |
| 2005/0079605 A1 | 4/2005 | Umana et al. |
| 2005/0112126 A1 | 5/2005 | Baca et al. |
| 2005/0118174 A1 | 6/2005 | Presta |
| 2005/0119455 A1 | 6/2005 | Fuh et al. |
| 2005/0136051 A1 | 6/2005 | Scallon |
| 2005/0142133 A1 | 6/2005 | Lazar et al. |
| 2005/0152894 A1 | 7/2005 | Krummen et al. |
| 2005/0186208 A1 | 8/2005 | Fyfe et al. |
| 2005/0227324 A1 | 10/2005 | Huang et al. |
| 2005/0233382 A1 | 10/2005 | Presta |
| 2005/0249722 A1 | 11/2005 | Beliard et al. |
| 2005/0249723 A1 | 11/2005 | Lazar |
| 2005/0260186 A1 | 11/2005 | Bookbinder et al. |
| 2005/0266000 A1 | 12/2005 | Bond et al. |
| 2005/0272916 A1 | 12/2005 | Hanai et al. |
| 2005/0276799 A1 | 12/2005 | Hinton et al. |
| 2005/0276805 A1 | 12/2005 | Hanai et al. |
| 2006/0009360 A1 | 1/2006 | Pifer et al. |
| 2006/0018909 A1 | 1/2006 | Oliner et al. |
| 2006/0018911 A1 | 1/2006 | Ault-Riche et al. |
| 2006/0024292 A1 | 2/2006 | Gerngross et al. |
| 2006/0024298 A1 | 2/2006 | Lazar |

(56)  References Cited

U.S. PATENT DOCUMENTS

| | | |
|---|---|---|
| 2006/0024300 A1 | 2/2006 | Adams et al. |
| 2006/0024304 A1 | 2/2006 | Gerngross et al. |
| 2006/0025576 A1 | 2/2006 | Miller et al. |
| 2006/0029604 A1 | 2/2006 | Gerngross et al. |
| 2006/0034828 A1 | 2/2006 | Gerngross et al. |
| 2006/0034829 A1 | 2/2006 | Gerngross et al. |
| 2006/0034830 A1 | 2/2006 | Gerngross et al. |
| 2006/0067930 A1 | 3/2006 | Adams et al. |
| 2006/0074225 A1 | 4/2006 | Chamberlain et al. |
| 2006/0088523 A1 | 4/2006 | Andya et al. |
| 2006/0104968 A1 | 5/2006 | Bookbinder et al. |
| 2006/0121032 A1 | 6/2006 | Dahiyat et al. |
| 2006/0122370 A1 | 6/2006 | Oliner et al. |
| 2006/0134709 A1 | 6/2006 | Stavenhagen et al. |
| 2006/0140934 A1 | 6/2006 | Gegg et al. |
| 2006/0153838 A1 | 7/2006 | Watkins et al. |
| 2006/0160996 A9 | 7/2006 | Lazar et al. |
| 2006/0173170 A1 | 8/2006 | Chamberlain et al. |
| 2006/0194290 A1 | 8/2006 | Presta |
| 2006/0194291 A1 | 8/2006 | Presta |
| 2006/0194954 A1 | 8/2006 | Idusogie et al. |
| 2006/0194957 A1 | 8/2006 | Presta |
| 2006/0198840 A1 | 9/2006 | Dall'Acqua et al. |
| 2006/0235208 A1 | 10/2006 | Lazar et al. |
| 2006/0246004 A1 | 11/2006 | Adams et al. |
| 2006/0246071 A1 | 11/2006 | Green et al. |
| 2006/0275282 A1 | 12/2006 | Moore et al. |
| 2006/0275283 A1 | 12/2006 | Van Vlijmen et al. |
| 2006/0280747 A1 | 12/2006 | Fuh et al. |
| 2007/0003546 A1 | 1/2007 | Lazar et al. |
| 2007/0009523 A1 | 1/2007 | Presta |
| 2007/0020260 A1 | 1/2007 | Presta |
| 2007/0020267 A1 | 1/2007 | Fuh et al. |
| 2007/0036806 A1 | 2/2007 | Glaesner et al. |
| 2007/0041966 A1 | 2/2007 | Armour et al. |
| 2007/0048300 A1 | 3/2007 | Taylor et al. |
| 2007/0053901 A1 | 3/2007 | Lazar et al. |
| 2007/0061900 A1 | 3/2007 | Murphy et al. |
| 2007/0117126 A1 | 5/2007 | Sidhu et al. |
| 2007/0122403 A1 | 5/2007 | Dall'Acqua et al. |
| 2007/0122406 A1 | 5/2007 | Chamberlain et al. |
| 2007/0135620 A1 | 6/2007 | Chamberlain et al. |
| 2007/0141065 A1 | 6/2007 | Fuh et al. |
| 2007/0148171 A1 | 6/2007 | Lazar et al. |
| 2007/0160597 A1 | 7/2007 | Lazar et al. |
| 2007/0160598 A1 | 7/2007 | Dennis et al. |
| 2007/0161783 A1 | 7/2007 | Barbosa et al. |
| 2007/0166309 A1 | 7/2007 | Lazar et al. |
| 2007/0202098 A1 | 8/2007 | Lazar et al. |
| 2007/0219133 A1 | 9/2007 | Lazar et al. |
| 2007/0224189 A1 | 9/2007 | Lazar et al. |
| 2007/0224192 A1 | 9/2007 | Lazar et al. |
| 2007/0231329 A1 | 10/2007 | Lazar et al. |
| 2007/0237764 A1 | 10/2007 | Birtalan et al. |
| 2007/0237765 A1 | 10/2007 | Lazar et al. |
| 2007/0237766 A1 | 10/2007 | Lazar et al. |
| 2007/0237767 A1 | 10/2007 | Lazar et al. |
| 2007/0238665 A1 | 10/2007 | Lazar et al. |
| 2007/0243188 A1 | 10/2007 | Lazar et al. |
| 2007/0248602 A1 | 10/2007 | Lazar et al. |
| 2007/0248603 A1 | 10/2007 | Lazar et al. |
| 2007/0286859 A1 | 12/2007 | Lazar et al. |
| 2007/0292936 A1 | 12/2007 | Barthelemy et al. |
| 2008/0051563 A1 | 2/2008 | Lazar et al. |
| 2008/0057056 A1 | 3/2008 | Lazar et al. |
| 2008/0069820 A1 | 3/2008 | Fuh et al. |
| 2008/0095762 A1 | 4/2008 | Presta |
| 2008/0138338 A1 | 6/2008 | Idusogie et al. |
| 2008/0152649 A1 | 6/2008 | Chamberlain et al. |
| 2008/0154025 A1 | 6/2008 | Lazar et al. |
| 2008/0161541 A1 | 7/2008 | Lazar et al. |
| 2008/0181890 A1 | 7/2008 | Lazar et al. |
| 2008/0206242 A1 | 8/2008 | Lawrence et al. |
| 2008/0213215 A1 | 9/2008 | Krishnan et al. |
| 2008/0274105 A1 | 11/2008 | Presta |
| 2008/0274108 A1 | 11/2008 | Presta |
| 2009/0041770 A1 | 2/2009 | Chamberlain et al. |
| 2009/0054323 A1 | 2/2009 | Oliner et al. |
| 2009/0060911 A1 | 3/2009 | Ravetch |
| 2009/0068182 A1 | 3/2009 | Young et al. |
| 2009/0148441 A1 | 6/2009 | Gillies |
| 2009/0162359 A1 | 6/2009 | Klein et al. |
| 2009/0162360 A1 | 6/2009 | Klein et al. |
| 2009/0163699 A1 | 6/2009 | Chamberlain et al. |
| 2009/0175851 A1 | 7/2009 | Klein |
| 2009/0215991 A1 | 8/2009 | Lazar et al. |
| 2009/0232811 A1 | 9/2009 | Klein et al. |
| 2010/0098730 A1 | 4/2010 | Lowman et al. |
| 2010/0166740 A1 | 7/2010 | Endl et al. |
| 2010/0166749 A1 | 7/2010 | Presta |
| 2011/0044998 A1 | 2/2011 | Bedian et al. |
| 2011/0052584 A1 | 3/2011 | Ravetch |
| 2011/0086050 A1 | 4/2011 | Presta et al. |
| 2011/0250130 A1 | 10/2011 | Benatuil et al. |
| 2011/0293632 A1 | 12/2011 | Presta |
| 2012/0201813 A1 | 8/2012 | Presta |
| 2012/0321627 A1 | 12/2012 | Baehner et al. |
| 2013/0156789 A1 | 6/2013 | Brinkmann et al. |
| 2014/0017244 A1 | 1/2014 | Duerr et al. |
| 2014/0065151 A1 | 3/2014 | Brinkmann et al. |
| 2014/0065707 A1 | 3/2014 | Brinkmann et al. |
| 2015/0004166 A1 | 1/2015 | Baehner et al. |
| 2015/0239981 A1 | 8/2015 | Baehner et al. |
| 2016/0068613 A1 | 3/2016 | Regula et al. |
| 2016/0215045 A1 | 7/2016 | Leung et al. |
| 2017/0044246 A1 | 2/2017 | Schlothauer et al. |

FOREIGN PATENT DOCUMENTS

| | | |
|---|---|---|
| CN | 1565622 A | 1/2005 |
| CN | 101098890 | 1/2008 |
| CN | 102191209 A | 9/2011 |
| CN | 102250247 A | 11/2011 |
| CN | 102250248 A | 11/2011 |
| CN | 102453577 A | 5/2012 |
| CN | 102753577 A | 10/2012 |
| CN | 103533950 A | 1/2014 |
| CN | 104066448 A | 9/2014 |
| CN | 104582728 A | 4/2015 |
| CN | 106999511 A | 8/2017 |
| CN | 107080843 A | 8/2017 |
| CN | 107428826 A | 12/2017 |
| EC | SP992970 A1 | 1/2000 |
| EP | 0404097 B1 | 9/1996 |
| EP | 0425235 B1 | 9/1996 |
| EP | 0359096 B1 | 11/1997 |
| EP | 1176195 A1 | 1/2002 |
| EP | 0666868 B2 | 6/2002 |
| EP | 1331266 A1 | 7/2003 |
| EP | 1331266 A4 | 7/2003 |
| EP | 0904107 B1 | 10/2004 |
| EP | 0811691 B1 | 12/2004 |
| EP | 1498491 A1 | 1/2005 |
| EP | 1498491 A4 | 1/2005 |
| EP | 1068241 B1 | 10/2007 |
| EP | 1870459 A1 | 12/2007 |
| EP | 1270595 B1 | 7/2008 |
| EP | 1692182 B1 | 4/2010 |
| EP | 2248829 A1 | 11/2010 |
| EP | 2252632 B1 | 1/2014 |
| EP | 2691417 B1 | 8/2018 |
| JP | 2006-255668 | 9/2006 |
| JP | 2012-502622 A | 2/2012 |
| JP | 2018-517773 A | 7/2018 |
| WO | 88/07089 A1 | 9/1988 |
| WO | 92/016562 A1 | 10/1992 |
| WO | 93/01161 A1 | 1/1993 |
| WO | 1993/006217 A1 | 4/1993 |
| WO | 93/08829 A1 | 5/1993 |
| WO | 93/16185 A2 | 8/1993 |
| WO | 93/16185 A3 | 8/1993 |
| WO | 93/22332 A2 | 11/1993 |
| WO | 93/22332 A3 | 11/1993 |
| WO | 94/08027 A1 | 4/1994 |

(56) References Cited

FOREIGN PATENT DOCUMENTS

| | | | |
|---|---|---|---|
| WO | 94/10202 | A1 | 5/1994 |
| WO | 94/11026 | A2 | 5/1994 |
| WO | 94/11026 | A3 | 5/1994 |
| WO | 94/29350 | | 12/1994 |
| WO | 94/29351 | A2 | 12/1994 |
| WO | 95/009917 | A1 | 4/1995 |
| WO | 96/027011 | A1 | 9/1996 |
| WO | 1996/27011 | A1 | 9/1996 |
| WO | 96/30046 | A1 | 10/1996 |
| WO | 96/32478 | A1 | 10/1996 |
| WO | 97/01580 | A1 | 1/1997 |
| WO | 97/28267 | A1 | 8/1997 |
| WO | 97/30087 | A1 | 8/1997 |
| WO | 97/34631 | A1 | 9/1997 |
| WO | 97/43316 | A1 | 11/1997 |
| WO | 97/44362 | A1 | 11/1997 |
| WO | 98/23289 | A1 | 6/1998 |
| WO | 98/33924 | A1 | 8/1998 |
| WO | 98/45331 | A2 | 10/1998 |
| WO | 98/45331 | A3 | 10/1998 |
| WO | 98/045332 | A2 | 10/1998 |
| WO | 98/48032 | A2 | 10/1998 |
| WO | 98/48032 | A3 | 10/1998 |
| WO | 98/050431 | A2 | 11/1998 |
| WO | 98/050431 | A3 | 11/1998 |
| WO | 98/52975 | A1 | 11/1998 |
| WO | 98/58964 | A1 | 12/1998 |
| WO | 99/22764 | A1 | 5/1999 |
| WO | 99/043713 | A1 | 9/1999 |
| WO | 99/051642 | A1 | 10/1999 |
| WO | 99/54342 | A1 | 10/1999 |
| WO | 99/58572 | A1 | 11/1999 |
| WO | 00/09560 | A2 | 2/2000 |
| WO | 00/09560 | A3 | 2/2000 |
| WO | 2000/035956 | A1 | 6/2000 |
| WO | 00/42072 | A2 | 7/2000 |
| WO | 2000/42072 | A2 | 7/2000 |
| WO | 00/61739 | A1 | 10/2000 |
| WO | 2000/075348 | A1 | 12/2000 |
| WO | 2000/075348 | A9 | 12/2000 |
| WO | 01/40309 | A2 | 6/2001 |
| WO | 01/64754 | A1 | 7/2001 |
| WO | 01/58957 | A2 | 8/2001 |
| WO | 01/58957 | A3 | 8/2001 |
| WO | 01/77181 | A2 | 10/2001 |
| WO | 01/077342 | A1 | 10/2001 |
| WO | 02/031140 | A1 | 4/2002 |
| WO | 02/060919 | A2 | 8/2002 |
| WO | 02/083854 | A2 | 10/2002 |
| WO | 03/011878 | A2 | 2/2003 |
| WO | 2003/020906 | A2 | 3/2003 |
| WO | 2003/030833 | A2 | 4/2003 |
| WO | 03/035835 | A2 | 5/2003 |
| WO | 03/035835 | A3 | 5/2003 |
| WO | 2003/055993 | A1 | 7/2003 |
| WO | 2003/057134 | A2 | 7/2003 |
| WO | 03/073238 | A2 | 9/2003 |
| WO | 03/073238 | A3 | 9/2003 |
| WO | 2003/074679 | A2 | 9/2003 |
| WO | 2003/106501 | A1 | 12/2003 |
| WO | 2004/004662 | A2 | 1/2004 |
| WO | 2004/004662 | A3 | 1/2004 |
| WO | 2004/004798 | A2 | 1/2004 |
| WO | 2004/011611 | A2 | 2/2004 |
| WO | 2004/029207 | A2 | 4/2004 |
| WO | 2004/029207 | A3 | 4/2004 |
| WO | 2004/035752 | A2 | 4/2004 |
| WO | 2004/035752 | A3 | 4/2004 |
| WO | 2004/063351 | A2 | 7/2004 |
| WO | 2004/092219 | A2 | 10/2004 |
| WO | 2004/092219 | A3 | 10/2004 |
| WO | 2004/099249 | A2 | 11/2004 |
| WO | 2005/000900 | A1 | 1/2005 |
| WO | 2005/012359 | A2 | 2/2005 |
| WO | 2005/018572 | A2 | 4/2005 |
| WO | 2005/035727 | A2 | 4/2005 |
| WO | 2005/035727 | A3 | 4/2005 |
| WO | 2005/037867 | A1 | 4/2005 |
| WO | 2005/040217 | A2 | 5/2005 |
| WO | 2005/040217 | A8 | 5/2005 |
| WO | 2005/044853 | A2 | 5/2005 |
| WO | 2005/047327 | A2 | 5/2005 |
| WO | 2005/047327 | A8 | 5/2005 |
| WO | 2005/054273 | A2 | 6/2005 |
| WO | 2005/068503 | A2 | 7/2005 |
| WO | 2005/074524 | A2 | 8/2005 |
| WO | 2005/074524 | A3 | 8/2005 |
| WO | 2005/100402 | A1 | 10/2005 |
| WO | 2005/123780 | A2 | 12/2005 |
| WO | 2006/002058 | A2 | 1/2006 |
| WO | 2006/019447 | A1 | 2/2006 |
| WO | 2006/020114 | A2 | 2/2006 |
| WO | 2006/020114 | A3 | 2/2006 |
| WO | 2006/020258 | A2 | 2/2006 |
| WO | 2006/029879 | A2 | 3/2006 |
| WO | 2006/029879 | A3 | 3/2006 |
| WO | 2006/031370 | A2 | 3/2006 |
| WO | 2006/044908 | A2 | 4/2006 |
| WO | 2006/045049 | A1 | 4/2006 |
| WO | 2006/047350 | A2 | 4/2006 |
| WO | 2006/047350 | A3 | 5/2006 |
| WO | 2006/053301 | A2 | 5/2006 |
| WO | 2006/053301 | A3 | 5/2006 |
| WO | 2006/053301 | A9 | 5/2006 |
| WO | 2006/068953 | A2 | 6/2006 |
| WO | 2006/076594 | A2 | 7/2006 |
| WO | 2006/076594 | A3 | 7/2006 |
| WO | 2006/093794 | A1 | 9/2006 |
| WO | 2006/116260 | A2 | 11/2006 |
| WO | 2007/024715 | A2 | 3/2007 |
| WO | 2007/024715 | A9 | 3/2007 |
| WO | 2007/033216 | A2 | 3/2007 |
| WO | 2007/044887 | A2 | 4/2007 |
| WO | 2007/068895 | A1 | 6/2007 |
| WO | 2007/068895 | A9 | 6/2007 |
| WO | 2007/089445 | A2 | 8/2007 |
| WO | 2007/109254 | A2 | 9/2007 |
| WO | 2007/110205 | A2 | 10/2007 |
| WO | 2007/147901 | A1 | 12/2007 |
| WO | 2008/073300 | A2 | 6/2008 |
| WO | 2008/077077 | A2 | 6/2008 |
| WO | 2008/132568 | A2 | 11/2008 |
| WO | 2008/149147 | A2 | 12/2008 |
| WO | 2008/149149 | A2 | 12/2008 |
| WO | 2009/006520 | A1 | 1/2009 |
| WO | 2009/023955 | A1 | 2/2009 |
| WO | 2009/032782 | A2 | 3/2009 |
| WO | 2009/058492 | A2 | 5/2009 |
| WO | 2009/058812 | A1 | 5/2009 |
| WO | 2009/068649 | A2 | 6/2009 |
| WO | 2009/073160 | A1 | 6/2009 |
| WO | 2009/073569 | A2 | 6/2009 |
| WO | 2009/080251 | A1 | 7/2009 |
| WO | 2009/080252 | A1 | 7/2009 |
| WO | 2009/080253 | A1 | 7/2009 |
| WO | 2009/080254 | A1 | 7/2009 |
| WO | 2009/086320 | A1 | 7/2009 |
| WO | 2009/089004 | A1 | 7/2009 |
| WO | 2009/100309 | A2 | 8/2009 |
| WO | 2009/100309 | A3 | 8/2009 |
| WO | 2009/105269 | A1 | 8/2009 |
| WO | 2009/134776 | A2 | 11/2009 |
| WO | 2009/136352 | | 11/2009 |
| WO | 2009/142460 | A2 | 11/2009 |
| WO | 2009/155513 | | 12/2009 |
| WO | 2009/155724 | | 12/2009 |
| WO | 2010/027981 | | 3/2010 |
| WO | 2010/040508 | A1 | 4/2010 |
| WO | 2010/045193 | A1 | 4/2010 |
| WO | 2010/069532 | A1 | 6/2010 |
| WO | 2010/077634 | A1 | 7/2010 |
| WO | 2010/129304 | A2 | 11/2010 |
| WO | 2010/129304 | A3 | 11/2010 |
| WO | 2010/148223 | A2 | 12/2010 |

(56) References Cited

FOREIGN PATENT DOCUMENTS

| | | |
|---|---|---|
| WO | 1999/37791 A1 | 2/2011 |
| WO | 2011/014469 | 2/2011 |
| WO | 2011/039370 A1 | 4/2011 |
| WO | 2011/090754 A1 | 7/2011 |
| WO | 2011/090762 A1 | 7/2011 |
| WO | 2011/106300 A2 | 9/2011 |
| WO | 2011/117329 A1 | 9/2011 |
| WO | 2011/117330 A1 | 9/2011 |
| WO | 2011/139718 | 11/2011 |
| WO | 2011/143545 A1 | 11/2011 |
| WO | 2012/058768 A1 | 6/2012 |
| WO | 2012/058768 A8 | 6/2012 |
| WO | 2012/097019 A1 | 7/2012 |
| WO | 2012/130831 A1 | 10/2012 |
| WO | 2012/131078 A1 | 10/2012 |
| WO | 2012/146628 A1 | 11/2012 |
| WO | 2013/056233 A1 | 4/2013 |
| WO | 2013/096291 A2 | 6/2013 |
| WO | 2013/096291 A3 | 6/2013 |
| WO | 2013/132044 | 9/2013 |
| WO | 2013/157953 A1 | 10/2013 |
| WO | 2013/157954 A1 | 10/2013 |
| WO | 2013/181452 A1 | 12/2013 |
| WO | 2014/009465 A1 | 1/2014 |
| WO | 2014/031429 A2 | 2/2014 |
| WO | 2014/177459 A2 | 11/2014 |
| WO | 2015/083978 A1 | 6/2015 |
| WO | 2015/107015 A1 | 7/2015 |
| WO | 2016/073915 A1 | 5/2016 |
| WO | 2016/073918 A1 | 5/2016 |
| WO | 2016/094673 A1 | 6/2016 |
| WO | 2016/109822 A1 | 7/2016 |
| WO | 2016/120413 A1 | 8/2016 |
| WO | 2016/122996 A1 | 8/2016 |
| WO | 2016/208989 A1 | 12/2016 |
| WO | 2017/075259 A1 | 5/2017 |
| WO | 2017/085253 A1 | 5/2017 |
| WO | 2017/106770 A1 | 6/2017 |
| WO | 2017/129685 A1 | 8/2017 |
| WO | 2017/197199 A1 | 11/2017 |
| WO | 2017/218977 A2 | 12/2017 |
| WO | 2018/122053 A1 | 7/2018 |
| WO | 2018/175752 A1 | 9/2018 |
| WO | 2019/217927 A1 | 11/2019 |

OTHER PUBLICATIONS

Atwell et al., "Stable heterodimers from remodeling the domain interface of a homodimer using a phage display library" J Mol Biol 270(1):26-35 ( 1997).

Berkman, R. A. et al., "Expression of the vascular permeability factor/vascular endothelial growth factor gene in central nervous system neoplasms" J Clin Invest 91:153-159 (Jan. 1993).

Boerner et al., "Production of Antigen-Specific Human Monoclonal Antibodies From In Vitro-Primed Human Splenocytes" J Immunol 147(1):86-95 (Jul. 1991).

Brown, L. F. et al., "Expression of vascular permeability factor (vascular endothelial growth factor) and its receptors in adenocarcinomas of the gastrointestinal tract" Cancer Res 53:4727-4735 (Oct. 1, 1993).

Brown, L. F. et al., "Expression of vascular permeability factor (vascular endothelial growth factor) and its receptors in breast cancer" Hum Pathol 26(1):86-91 ( 1995).

Bruggemann et al., "Designer mice: the production of human antibody repertoires in transgenic animals" Year in Immunology 7:33-40 ( 1993).

Chakravarthy, U., et al., "Phase I Trial of Anti-Vascular Endothelial Growth Factor/Anti-angiopoietin 2 Bispecific Antibody RG7716 for Neovascular Age-Related Macular Degeneration" Ophthalmol Retina 1(6):474-485 (Nov. 30, 2017).

Chakravarthy, U., et al., "The novel bispecific monoclonal anti-VEGF/anti-Ang2 antibody RG7716 shows promise in wet age-related macular degeneration patients with suboptimal response to prior anti-VEGF monotherapy" ARVO Annual Meeting Abstract 57 (Sep. 2016).

Cheung et al., "Endothelial Tie2/Tek Ligands Angiopoietin-1 (ANGPT1) and Angiopoietin-2 (ANGPT2): Regional Localization of the Human Genes to 8q22.3-q23 and 8p23" Genomics 48:389-391 ( 1998).

Cole et al. Monoclonal Antibodies and Cancer Therapy "The EBV-hybridoma technique and its application to human lung cancer" New York:Alan R. Liss, Inc.,:77-96 ( 1985).

Connolly et al., "Human vascular permeability factor. Isolation from U937 cells" J Biol Chem. 264(33):20017-24 ( 1989).

Daugherty et al., "Chapter 8: Formulation and Delivery Issues for Monoclonal Antibody Therapeutics" Current Trends in Monoclonal Antibody Development and Manufacturing, Springer:103-129 ( 2006).

Davis et al. et al., "Isolation of angiopoietin-1, a ligand for the TIE2 receptor, by secretion-trap expression cloning" Cell 87(7):1161-1169 (Dec. 27, 1996).

Dvorak et al., "Vascular permeability factor/vascular endothelial growth factor, microvascular hyperpermeability, and angiogenesis" Am J Pathol 146(5):1029-1039 (May 1995).

Ferrara and Davis-Smyth, "The Biology of Vascular Endothelial Growth Factor" Endocr Rev 18(1):4-25 ( 1997).

Folkman and Shing, "Angiogenesis" J Biol Chem 267(16):10931-10934 (Jun. 5, 1992).

Garner et al. Pathobiology of Ocular Disease. A Dynamic Approach "Vascular Diseases" Garner, A., Klintworth GK Eds., 2nd edition, NY:Marcel Dekker,:1625-1710 ( 1994).

Hamilton LM, et al., "The role of the epidermal growth factor receptor in sustaining neutrophil inflammation in severe asthma (abstract)" Clin Exp Allergy 33(2):233-40 (Feb. 2003).

Hoogenboom et al., "By-passing immunisation. Human antibodies from synthetic repertoires of germline VH gene segments rearranged in vitro" J Mol Biol 227(2):381-388 (Sep. 20, 1992).

Houck et al., "The Vascular Endothelial Growth Factor Family: Identification of a Fourth Molecular Species and Characterization of Alternative Splicing of RNA" Mol Endocrinol 5(12):1806-14 ( 1991).

Hsu et al., "Poorer outcomes in real-world studies of anti-vascular endothelial growth factor therapy for neovascular age-related macular degeneration" Ophthalmology 127(9):1189-1190 (2020).

Jacobovits et al., "Analysis of homozygous mutant chimeric mice: Deletion of the immunoglobulin heavy-chain joining region blocks B-cell development and antibody production" PNAS USA 90:2551-2555 ( 1993).

Jacobovits et al., "Germ-line Transmission and Expression of a Human-derived Yeast Artificial Chromosome" Nature 362:255-258 ( 1993).

Johnson, G., et al., "Kabat Database and its applications: 30 years after the first variability plot" Nucleic Acids Res 28(1):214-218 (Jan. 1, 2000).

Kabat et al., "Evolutionary and structural influences on light chain constant (CL) region of human and mouse immunoglobulins" PNAS USA 72(7):2785-2788 (Jul. 1, 1975).

Keck et al., "Vascular Permeability Factor, An Endothelial Cell Mitogen Related to PDGF" Science 246:1309-1312 ( 1989).

Kim et al., "Angiopoietin-2 at high concentration can enhance endothelial cell survival through the phosphatidylinositol 3'-kinase/Akt signal transduction pathway" Oncogene 19:4549-4552 (2000).

Kim et al., "Molecular cloning and characterization of a novel angiopoietin family protein, angiopoietin-3" FEBS Lett 443(3):353-356 ( 1999).

Kim et al., "Molecular cloning, expression and characterization of angiopoietin-related protein" J Biol Chem 274(37):26523-26528 ( 1999).

Klagsbrun and D'Amore, "Regulators of angiogenesis" Ann Rev Physiol 53:217-239 (1991).

Leung et al., "Vascular Endothelial Growth Factor is a Secreted Angiogenic Mitogen" Science 246:1306-1309 (Dec. 8, 1989).

Maisonpierre et al. et al., "Angiopoietin-2, a Natural Antagonist for Tie2 that Disrupts in vivo Angiogenesis" Science 277:55-60 (Jul. 4, 1997).

(56) References Cited

OTHER PUBLICATIONS

Manning et al., "Stability of Protein Pharmaceuticals" Pharm. Res. 6(11):903-918 ( 1989).

Marks, J.D., et al., "By-passing immunization, human antibodies from V-gene libraries displayed on phage" J Mol Biol 222(3):581-597 (Dec. 5, 1991).

Mattern, J. et al., "Association of vascular endothelial growth factor expression with intratumoral microvessel density and tumour cell proliferation in human epidermoid lung carcinoma" Brit J Cancer 73:931-934 ( 1996).

Merchant et al., "An efficient route to human bispecific IgG" Nat Biotechnol 16(7):677-681 ( 1998).

Meyer et al., "Bevacizumab immune complexes activate platelets and induce thrombosis in FCGR2A transgenic mice" J. of Thrombosis and Haemostasis 7:171-181 ( 2008).

Morrison et al., "Chimeric human antibody molecules: Mouse antigen-binding domains with human constant region domains" PNAS USA 81:6851-6855 (Nov. 1984).

Neuberger, M.S., et al., "A hapten-specific chimaeric IgE antibody with human physiological effector function" Nature 314(6008):268-270 (Mar. 21, 1985).

Other Database, NCT02484690 (retrieved Aug. 4, 2022) https//clinicaltrials.gov.ct2/history/, Jun. 24, 2015.

Other Database, NCT03038880 (retrieved Aug. 4, 2022), Jan. 31, 2017.

Regula, J., et al., "Targeting key angiogenic pathways with a bispecific CrossMAb optimized for neovascular eye diseases" EMBO Mol Med 8(11):1265-1288 (Nov. 1, 2016).

Ridgway et al., "'Knobs-into-holes' Engineering of Antibody CH3 Domains for Heavy Chain Heterodimerization" Protein Eng 9(7):617-621 ( 1996).

Riechmann et al., "Reshaping human antibodies for therapy" Nature 332:323-327 (Mar. 24, 1988).

Ritter et al., "Myeloid progenitors differentiate into microglia and promote vascular repair in a model of ischemic retinopathy" J. of Clinical Investigation 116(12):3266-3276 ( 2006).

Russelakis-Carneiro et al., "Inflammatory response and retinal ganglion cell degeneration following intraocular injection of ME7" Neuropathology and Applied Neurobiology 25:196-206 ( 1999).

US Clinical TRIALS.gov et al., "A Study of Faricimab (RO6867461) in Participants With Center-Involving Diabetic Macular Edema (Boulevard)" (ClinicalTrials.gov Identifier: NCT02699450; History of Changes; Submitted Date: Dec. 21, 2017 (v9); Retrieved: Aug. 2, 2021),:1-13 (Dec. 21, 2017).

Van Dijk and Van De Winkel et al., "Human antibodies as next generation therapeutics" Curr Opin Chem Biol 5(4):368-374 (Aug. 2001).

Wang et al., "Antibody structure, instability, and formulation" Journal of Pharmaceutical Sciences 96(1):1-26 ( 2007).

Wray et al., "Experimental allergic encephalomyelitis" Arch. Neurol. 33:183-185 ( 1976).

Yancopoulos et al., "Vascular-specific growth factors and blood vessel formation" Nature 407:242-248 (2000).

Zheng et al., "Influence of pH, buffer species, and storage temperature on physicochemical stability of a humanized monoclonal antibody LA298" Int. J. Pharm. 308:46-51 ( 2006).

"International Preliminary Report on Patentability—PCT/EP2019/052704" Issued by the International Searching Authority on: Aug. 11, 2020; Chapter I,:pp. 1-8 (Aug. 20, 2020).

International Search Report—PCT/EP2019/052704, (w/Written Opinion),:pp. 1-14 Issued by the International Searching Authority on May 7, 2019.

Rohades et al., "Management of macular edema due to central retinal vein occlusion—The role of aflibercept" Taiwan J Ophthalmol 7:70-76.

US Clinical TRIALS.gov et al., "A Proof-of-Concept Study of Faricimab (RO6867461) in Participants with Choroidal Neovascularization (CNV) Secondary to Age-Related Macular Degeneration (AMD) (Avenue)" (ClinicalTrials. gov ID: NCT02484690; History of Changes;

Version 15; First Posted: Jun. 30, 2015; Last Update Submitted: Feb. 2, 2018; Retrieved: Feb. 12, 2018), 1-6 (Feb. 2, 2018).

Rohades et al., "Management of macular edema due to central retinal vein occlusion—The role of aflibercept" Taiwan J Ophthalmol 7:70-76 (2017).

The Merck Index, An encyclopedia of Chemicals, Drugs, and Biologicals), Maryadale J. O'Neil, 14th Edition edition, Whitehouse Station, NJ USA:Merck Research Laboratories, Division of Merck & Co, Inc.,: 26-27 ( 2006).

Abes, R., et al., "Activating and inhibitory Fcγ receptors in immunotherapy: being the actor or being the target" Expert Rev Clin Immunol 5(6):735-747 (Nov. 1, 2009).

Adamis, A., et al., "Inhibition of Vascular Endothelial Growth Factor Prevents Retinal Ischemia-Associated Iris Neovascularization in a Nonhuman Primate" Arch Ophthalmol—Chic 114(1):66-71 (Jan. 1, 1996).

Adler, M. et al., "Challenges in the Development of Pre-filled Syringes for Biologics from a Formulation Scientist's Point of View" Amer Pharma REV:1-8 (Feb. 1, 2012).

Ahmad, S., et al., "Differential Expression of Angiopoietin-1 and Angiopoietin-2 in Colon Carcinoma" Cancer 92(5):1138-1143 (Sep. 1, 2001).

Allan, R. et al., "Studies on the complement-binding site of rabbit immunoglobulin G-II. The reaction of rabbit IgG and its fragments with C1q" Immunochemistry 11(5):243-248 (May 1, 1974).

Allan, R., et al., "Studies on the complement-binding site of rabbit immunoglobulin G-I. Modification of tryptophan residues and their role in anticomplementary activity of rabbit IgG" Immunochemistry 11(4):175-180 (Apr. 1, 1974).

Almagro and Fransson, "Humanization of antibodies" Front Biosci 13:1619-1633 (Jan. 1, 2008).

Anderson, D., et al., "Targeted anti-cancer therapy using rituximab, a chimaeric anti-CD20 antibody (IDEC-C2B8) in the treatment of non-Hodgkin's B-cell lymphoma" Biochem Soc Trans 25(2):705-708 (May 1, 1997).

Angal, S., et al., "A single amino acid substitution abolishes the heterogeneity of chimeric mouse/human (IgG4) antibody" Molec Immunol 30(1):105-108 (Jan. 1, 1993).

Angata, K., et al., "Differential and Cooperative Polysialylation of the Neural Cell Adhesion Molecule by Two Polysialyltransferases, PST and STX" J Biol Chem 273(43):28524-28532 (Oct. 23, 1998).

Armour, K., et al., "Recombinant Human IgG Molecules Lacking Fcγ Receptor I Binding and Monocyte Triggering Activities" Eur J Immunol 29(8):2613-2624 (Aug. 1, 1999).

Artandi, S et al., "Monoclonal IgM rheumatoid factors bind IgG at a discontinuous epitope comprised of amino acid loops from heavy-chain constant-region domains 2 and 3" PNAS 89(1):94-98 (Jan. 1, 1992).

Baca, M., et al., "Antibody humanization using monovalent phage display" J Biol Chem 272(16):10678-10684 (Apr. 18, 1997).

Bacac, M., et al., "A Novel Carcinoembryonic Antigen T-Cell Bispecific Antibody (CEA TCB) for the Treatment of Solid Tumors" Clin Cancer Res 22(13):3286-3297 (Jul. 1, 2016).

Bacac, M., et al., "CEA TCB: A novel head-to-tail 2:1 T cell bispecific antibody for treatment of CEA-positive solid tumors" Oncoimmunology 5(8 Suppl e1203498):1-3 (Jun. 24, 2016).

Bacac, M., et al., "ITOC2-037. CEA TCB, A novel T-cell bispecific antibody with potent in vitro and in vivo antitumour activity against solid tumours" Eur J Cancer 51( Suppl 1):S13 (Mar. 1, 2015).

Barnes, L., et al., "Advances in animal cell recombinant protein production: GS-NS0 expression system" Cytotechnology 32(2):109-123 (Feb. 1, 2000).

Barnes, L.M. et al., "Characterization of the Stability of Recombinant Protein Production in the GS-NS0 Expression System" Biotechnol Bioeng (Epub: Mar. 14, 2001), 73(4):261-270 (May 20, 2001).

Beckman, R., et al., "Antibody Constructs in Cancer Therapy" Cancer 109(2):170-179 (Jan. 15, 2007).

Bhisitkul, R., et al., "Predictive Value in Retinal Vein Occlusions of Early Versus Late or Incomplete Ranibizumab Response Defined by Optical Coherence Tomography" Ophthalmology 120(5):1057-1063 (May 1, 2013).

Bloom, J., et al., "Intrachain disulfide bond in the core hinge region of human IgG4" Protein Sci 6(2):407-415 (Feb. 1, 1997).

(56) References Cited

OTHER PUBLICATIONS

Bolland, S., et al., "SHIP modulates immune receptor responses by regulating membrane association of Btk" Immunity 8(4):509-516 (Apr. 1, 1998).

Borgstrom, P., et al., "Complete Inhibition of Angiogenesis and Growth of Microtumors by Anti-Vascular Endothelial Growth Factor Neutralizing Antibody: Novel Concerts of Angiostatic Therapy from Intravital Videomicrocopy" Cancer Res 56(17):4032-4039 (Sep. 1, 1996).

Boyd, F., et al., "The Effect of the Removal of Sialic Acid, Galactose and Total Carbohydrate on the Functional Activity of Campath-1H." Mol Immunol 32(17-18):1311-1318 (Dec. 1, 1995).

Brambell, F.,, "The Transmission of Immunity from Mother to Young and the Catabolism of Immunoglobulins" Lancet 2(7473):1087-1093 (Nov. 19, 1966).

Bredius, R., et al., "Role of neutrophil FcγRIIa (CD32) and FcγRIIIb (CD16) polymorphic forms in phagocytosis of human IgG1- and IgG3-opsonized bacteria and erythrocytes" Immunology 83(4):624-630 (Dec. 1, 1994).

Brekke, O., et al., "Human IgG Isotype-Specific Amino Acid Residues Affecting Complement-Mediated Cell Lysis and Phagocytosis." Eur J Immunol 24(10):2542-2547 (Oct. 1, 1994).

Brekke, O., et al., "Structure-Function Relationships of Human IgG" Immunologist 2:125-130 ( 1994).

Brekke, O., et al., "Therapeutic antibodies for human diseases at the dawn of the twenty-first century" Nat Rev Drug Discov 2(1):52-62 (Jan. 1, 2003).

Brennan, M., et al., "Preparation of Bispecific Antibodies by Chemical Recombination of Monoclonal Immunoglobulin G1 Fragments" Science 229(4708):81-83 (Jul. 5, 1985).

Brodeur, B., et al. Monoclonal Antibody Production Techniques and Applications "Chapter 4: Mouse-Human Myeloma Partners for the Production of Heterohybridomas" Schook, L., ed., New York, N.Y.—USA:Marcel Dekker, Inc.,:51-63 (Jan. 1, 1987).

Brorson, K.,, "Mutational analysis of avidity and fine specificity of anti-levan antibodies" J Immunol 163(12):6694-6701 (Dec. 15, 1999).

Brown, J., et al., "A Human Monoclonal Anti-ANG2 Antibody Leads to Broad Antitumor Activity in Combination with VEGF Inhibitors and Chemotherapy Agents in Preclinical Models" Mole Cancer Ther 9(1):145-156 (Jan. 1, 2010).

Bruggemann, M., et al., "Comparison of the effector functions of human immunoglobulins using a matched set of chimeric antibodies" J Exp Med 166(5):1351-1361 (Nov. 1, 1987).

Brummell, D., et al., "Probing the combining site of an anti-carbohydrate antibody by saturation-mutagenesis: role of the heavy-chain CDR3 residues" ACS Biochemistry 32(4):1180-1187 (Feb. 2, 1993).

Brunker, P., et al., "RG7386, a novel tetravalent FAP-DR5 antibody, effectively triggers FAP-dependent, avidity-driven DR5 hyperclustering and tumor cell apoptosis" Mol Cancer Ther 15(5):946-957 ( 2016).

Burks, E., et al., "In vitro scanning saturation mutagenesis of an antibody binding pocket" PNAS 94(2):412-417 (Jan. 21, 1997).

Burnmeister, W., et al., "Crystal Structure of the Complex of Rat Neonatal Fc Receptor with Fc." Nature 372(6504):379-383 (Nov. 24, 1994).

Burton, D., et al., "Human Antibody Effector Function" Adv Immunol 51:1-84 (Jan. 1, 1992).

Burton, D., et al., "Molecular recognition of antibody (IgG) by cellular Fc receptor (FcRI)" Mol Immunol 25(11):1175-1181 (Nov. 1, 1988).

Burton, D., et al., "The Clq receptor site on immunoglobulin G" Nature 288(5789):338-344 (Nov. 27, 1980).

Burton, D., "Immunoglobulin G: Functional sites" Mol Immunol 22(3):161-206 (Mar. 1, 1985).

Burvenich, I., et al., "Homology modeling based site-directed mutagenesis of anti-Leγ antibody hu3S193 Fc:FcRn interactions" Abstract (1240) AACR Annual Meeting, Denver, CO, pp. 1 ( Apr. 18-22, 2009).

Byrn, R., et al., "Biological Properties of a CD4 Immunoadhesin" Nature 344(6267):667-670 (Apr. 12, 1990).

Cameron, D.,, "Specificity of Macrophage-Mediated Cytotoxicity: Role of Target and Effector Cell Fucose." Immunol Lett 11(1):39-44 (Jan. 1, 1985).

Campa, C., et al., "Anti-VEGF Therapy for Retinal Vein Occlusions" Curr Drug Targets 17(3):328-336 (Mar. 1, 2016).

Canfield, S., et al., "The binding affinity of human IgG for its high affinity Fc receptor is determined by multiple amino acids in the CH2 domain and is modulated by the hinge region" J Exp Med 173(6):1483-1491 (Jun. 1, 1991).

Capel, P., et al., "Heterogeneity of human IgG Fc receptors" Immunomethods 4(1):25-34 (Feb. 1, 1994).

Capon, D., et al., "Designing CD4 Immunoadhesins for AIDS Therapy" Nature 337(6207):525-531 (Feb. 9, 1989).

Carroll, R., et al., "Extensive C1q-Complement Initiated Lysis of Human Platelets by IgG Subclass Murine Monoclonal Antibodies to the CD9 Antigen" Thromb Res 59(5):831-839 (Sep. 1, 1990).

Carter, P. et al., "Improved oligonucleotide site-directed mutagenesis Using M13 vectors" Nucleic Acid Res 13(12):4431-4443 (Jun. 25, 1985).

Carter, P., et al., "Bispecific human IgG by design" J Immunol Methods 248(1-2):7-15 (Feb. 1, 2001).

Carter, P., et al., "Humanization of an anti-p185HER2 antibody for human cancer therapy" PNAS USA 89(10):4285-4289 (May 15, 1992).

Casset, F., et al., "A peptide mimetic of an anti-CD4 monoclonal antibody by rational design" Biochem Biophys Res Commun 307(1):198-205 (Jul. 18, 2003).

Cespedes, M., "Mouse Models in Oncogenesis and Cancer Therapy" Clin Transl Oncol 8(5):318-329 (May 1, 2006).

Chan, A.C., et al., "Therapeutic antibodies for autoimmunity and inflammation" Nat Rev Immunol 10(5):301-316 (May 1, 2010).

Chan, L. et al., "Variable Region Domain Exchange in Human IgGs Promotes Antibody Complex Formation with Accompanying Structural Changes and Altered Affector Functions" Mol Immunol 41(5):527-538 (Jul. 1, 2004).

Chappel, M., et al., "Identification of Secondary FcγRI Binding Site within a Genetically Engineered Human IgG Antibody" J Biol Chem 268(33):25124-25131 (Nov. 25, 1993).

Chappel, M., et al., "Identification of the Fcγ Receptor Class I Binding Site in Human IgG Through the use of Recombinant IgG1/IgG2 Hybrid and Point-Mutated Antibodies." PNAS USA 88(20):9036-9040 (Oct. 15, 1991).

Chari, R., et al., "Immunoconjugates containing novel maytansinoids: Promising anticancer drugs" Cancer Res 52(1):127-131 (Jan. 1, 1992).

Charlton, K.A., "Expression and isolation of recombinant antibody fragments in E. coli" Methods Mol Biol 248:245-254 ( 2003).

Chen, F., et al., "New Horizons in Tumor Microenvironment Biology: Challenges and Opportunities" BMC Med 13:Article 45 (1-13) (Mar. 5, 2015).

Chen, Y., et al., "Selection and analysis of an optimized anti-VEGF antibody: crystal structure of an affinity-matured Fab in complex with antigen" J Mol Biol 293(4):865-881 (Sep. 13, 1999).

Chennamsetty, N., et al., "Aggregation-Prone Motifs in Human Immunoglobulin G" J Mol Biol 391(2):404-413 (Aug. 14, 2009).

Chennamsetty, N., et al., "Design of therapeutic proteins with enhanced stability" PNAS 106(29):11937-11942 (Jul. 1, 2009).

Cheung, G., et al., "Dual inhibition of angiopoietin-2 and vascular endothelial growth factor-A with Crossmab RG7716 suppressed laser-induced choroidal neovascularization in a non-human primate model" IOVS—Invest Opthalmol Vis Sci (Abstract :1174), 55(13):1 (Apr. 1, 2014).

Chin, J., et al., "Addition of a photocrosslinking amino acid to the genetic code of Escherichia coli" PNAS 99(17):11020-11024 (Aug. 1, 2002).

Chin, J., et al., "Addition of p-Azido-L-phenylalanine to the genetic code of Escherichia coli" ACS J Am Chem Soc 124(31):9026-9027 (Jul. 11, 2002).

Chin, J.,, "In vivo photocrosslinking with unnatural amino acid mutagenesis" Chembiochem 3(11):1135-1137 (Oct. 28, 2002).

(56)         References Cited

OTHER PUBLICATIONS

Chothia, C., et al., "Canonical structures for the hypervariable regions of immunoglobulins" J Mol Biol 196(4):901-917 (Aug. 20, 1987).

Chowdhury, P., "Engineering hot spots for affinity enhancement of antibodies" Methods Mol Biol 207:179-196 ( 2003).

Clackson, T., et al., "Making antibody fragments using phage display libraries" Nature 352(6336):624-628 (Aug. 15, 1991).

Clark, M., et al., "Molecular basis for a polymorphism involving Fc receptor II on human monocytes" J Immunol 143(5):1731-1734 (Sep. 1, 1989).

Clark, M.,, "IgG effector mechanisms" Chem Immunol 65:88-110 (Jan. 1, 1997).

Clynes, R. et al., "Modulation of immune complex-induced inflammation in vivo by the coordinate expression of activation and inhibitory Fc receptors" J Exp Med 189(1):179-185 (Jan. 4, 1999).

Clynes, R., et al., "Cytotoxic antibodies trigger inflammation through Fc receptors" Immunity 3(1):21-26 (Jul. 1, 1995).

Clynes, R., et al., "Fc receptors are required in passive and active immunity to melanoma" PNAS 95(2):652-656 (Jan. 20, 1998).

Clynes, R., et al., "Inhibitory Fc Receptors Modulate In Vivo Cytoxicity Against Tumor Targets" Nat Med 6(4):443-446 (Apr. 1, 2000).

Clynes, R., et al., "Uncoupling of immune complex formation and kidney damage in autoimmune glomerulonephritis" Science 279(5353):1052-1054 (Feb. 13, 1998).

Cohen, S., et al., "Changes in visual acuity in patients with wet age-related macular degeneration treated with intravitreal ranibizumab in daily clinical practice: the LUMIERE study" Retina 33(3):474-481 (Mar. 1, 2013).

Cohen, S., et al., "Nonchromosomal Antibiotic Resistance in Bacteria: Genetic Transformation of Escherichia coli by R-Factor DNA" PNAS 69(8):2110-2114 (Aug. 1, 1972).

Colman, P.M., "Effects of amino acid sequence changes on antibody-antigen interactions" Res Immunol 145(1):33-36 (Jan. 1, 1994).

Coloma, M., et al., "Design and Production of Novel Tetravalent Bispecific Antibodies" Nat Biotechnol 15(2):159-163 (Feb. 1, 1997).

Cook, J., et al., "Identification of Contact Residues in the IgE Binding Site of Human FceRIα" ACS Biochemistry 36(50):15579-15588 (Dec. 16, 1997).

Cosimi, A.,, "Clinical Development of Orthoclone OKT3" Transplant P 19(2 Suppl Suppl 1):7-16 (Apr. 1, 1987).

Coxon, A., et al., "Combined Treatment of Angiopoietin and VEGF Pathway Antagonists Enhances Antitumor Activity in Preclinical Models of Colon Carcinoma" Abstract (1113) 99th AACR Annual Meeting, San Diego, California, pp. 1-2 ( Apr. 12-16, 2008).

Cragg, M., et al., "Antibody specificity controls in vivo effector mechanisms of anti-CD20 reagents" Blood 103(7):2738-2743 (Apr. 1, 2004).

Cragg, M., et al., "Complement-mediated lysis by anti-CD20 mAb correlates with segregation into lipid rafts" Blood 101(3):1045-1052 (Feb. 1, 2003).

Cunningham, B., et al., "High-resolution epitope mapping of hGH-receptor interactions by alanine-scanning mutagenesis" Science 244(4908):1081-1085 (Jun. 2, 1989).

Daëron, M. et al., "Fc receptor biology" Annu Rev Immunol 15:203-234 ( 1997).

Dall'Acqua, W., et al., "Antibody humanization by framework shuffling" Methods 36(1):43-60 (Jan. 17, 2005).

Dall'Acqua, W., et al., "Increasing the affinity of a human IgG1 for the neonatal Fc receptor: biological consequences" J Immunol 169(9):5171-5180 (Nov. 1, 2002).

Dall'Acqua, W., et al., "Modulation of the effector functions of a human IgG1 through engineering of its hinge region" J Immunol 177(2):1129-1138 (Jul. 15, 2006).

Dall'Acqua, W., et al., "Properties of human IgG1s engineered for enhanced binding to the neonatal Fc receptor (FcRn)" J Biol Chem 281(33):23514-23524 (Aug. 18, 2006).

Dard, P. et al., "DNA Sequence Variability of IGHG3 Alleles Associated to the Main G3m Haplotypes in Human Populations" Eur J Human Genet 9(10):765-772 (Oct. 1, 2001).

Datta-Mannan, A., et al., "Humanized IgG1 variants with differential binding properties to the neonatal Fc receptor: relationship to pharmacokinetics in mice and primates" Drug Metab Dispos 35(1):86-94 (Jan. 1, 2007).

Datta-Mannan, A., et al., "Monoclonal antibody clearance. Impact of modulating the interaction of IgG with the neonatal Fc receptor" J Biol Chem 282(3):1709-1717 (Jan. 19, 2007).

Daugherty, A., et al., "Formulation and delivery issues for monoclonal antibody therapeutics" Adv Drug Deliv Rev (Epub: May 22, 2006), 58(5-6):686-706 (Aug. 7, 2006).

Davies, J. et al., "Expression of GnTIII in a Recombinant Anti-CD20 CHO Production Cell Line: Expression of Antibodies with Altered Glycoforms Leads to an Increase in ADCC Through Higher Affinity for FcγRIII" Biotechnol Bioeng 74(4):288-294 (Aug. 20, 2001).

Davis, R., et al., "Fc receptor homologs: newest members of a remarkably diverse Fc receptor gene family" Immunol Rev 190(1):123-136 (Dec. 1, 2002).

De Haas, M., et al., "Fcγ receptors of phagocytes" J Lab Clin Med 126(4):330-341 (Oct. 1, 1995).

De Pascalis, R., et al., "Grafting of 'Abbreviated' Complementarity-Determining Regions Containing Specificity-Determining Residues Essential for Ligand Contact to Engineer a Less Immunogenic Humanized Monoclonal Antibody" J Immunol 169(6):3076-3084 (Sep. 15, 2002).

De Reys, S., et al., "Human platelet aggregation by murine monoclonal antiplatelet antibodies is subtype-dependent" Blood 81(7):1792-1800 (Apr. 1, 1993).

De Vita, S., et al., "Efficacy of Selective B Cell Blockade in the Treatment of Rheumatoid Althritis" Arthritis Rheum 46(8):2029-2033 (Aug. 1, 2002).

Deisenhofer, J ., "Crystallographic Refinement and Atomic Models of a Human Fc Fragment and Its Complex with Fragment B of Protein A from Staphylococcus aureus at 2.9- and 2.8-A Resolution" ACS Biochemistry 20(9):2361-2370 (Apr. 28, 1981).

Deissler, H., et al., "Actions of Bevacizumab and Ranibizumab on Microvascular Retinal Endothelil Cells: Similarities and Differences" BR J Opthamol 96(7):1023-1028 (Apr. 26, 2012).

Deng, R., et al., "Pharrnacokinetics of Humanized Monoclonal Anti-Tumor Necrosis Factor-α Antibody and Its Neonatal Fc Receptor Variants in Mice and Cynomolgus Monkeys" Drug Metab Dispos 38(4):600-605 (Apr. 1, 2010).

Dennis, C.,, "Off By a Whisker" Nature 442:739-741 (Aug. 17, 2006).

Diabetic Retinopathy Clinical Res Network et al., "Randomized trial evaluating ranibizumab plus prompt or deferred laser or triamcinolone plus prompt laser for diabetic macular edema" Ophthalmology 117(6):1064-1077 (Jun. 1, 2010).

Dingchang, M. et al., "Current Status and Future Perspective of Research on Anti-VEGF/VEGFR Anti-cancer Drugs" Chin J Cancer Biother 22(5):637-645 (Oct. 1, 2015).

Dorai, H., et al., "Aglycosylated Chimeric Mouse/Human IgG1 Antibody Retains Some Effector Function." Hybridoma 10(2):211-217 (Apr. 1, 1991).

Dubowchik, G., et al., "Doxorubicin immunoconjugates containing bivalent, lysosomally-cleavable dipeptide linkages" Bioorg Med Chem Lett 12(11):1529-1532 (Jun. 3, 2002).

Dufner, P. et al., "Harnessing phage and ribosome display for antibody optimisation" Trends Biotechnol 24(11):523-529 (Nov. 1, 2006).

Duncan, A., et al., "Localization of the Binding Site for the Human High-Affinity Fc Receptor on IgG." Nature 332(6164):563-564 (Apr. 7, 1988).

Duncan, A., et al., "The Binding Site for Clq on IgG" Nature 332(6166):738-740 (Apr. 21, 1988).

Durocher, Y., et al., "High-level and high-throughput recombinant protein production by transient transfection of suspension-growing human 293-EBNA1 cells" Nucleic Acids Res 30(2):E9 (Jan. 15, 2002).

(56)  References Cited

OTHER PUBLICATIONS

Eccles, S., et al., "Monoclonal antibodies targeting cancer: 'magic bullets' or just the trigger?" Breast Cancer Res 3(2):86-90 (Dec. 20, 2001).

Edelman, G., et al., "The covalent structure of an entire γG immune globulin molecule" PNAS 63(1):78-85 (May 1, 1969).

El-Amine, M., et al., "In vivo induction of tolerance by an Ig peptide is not affected by the deletion of FcR or a mutated IgG Fc fragment" Int Immunol 14(7):761-766 (Jul. 1, 2002).

Elbein, A.,, "Glycosidase Inhibitors: Inhibitors of N-Linked Oligosaccharide Processing" FASEB J 5(15):3055-3063 (Dec. 1, 1991).

Ellman, J. et al. Methods in Enzymology: Molecular Design and Modeling: Concepts and Applications Part A: Proteins, Peptides, and Enzymes "Chapter 15: Biosynthetic method for introducing unnatural amino acids site-specifically into proteins" Langone, J, ed., First edition, Cambridge, MA—USA:Academic Press, vol. 202:301-336 (Oct. 9, 1991).

Ellsion, J., et al., "Linkage and sequence homology of two human immunoglobulin gamma heavy chain constant region genes" PNAS USA 79(6):1984-1988 (Mar. 1, 1982).

Elman, M., et al., "Intravitreal Ranibizumab for diabetic macular edema with prompt versus deferred laser treatment: 5-year randomized trial results" Ophthalmology 122(2):375-381 (Feb. 1, 2015).

European Patent Office, "European Patent Application No. 11160251. 2" (Certified Copy—Priority Document),:1-128 (Mar. 29, 2011).

European Patent Office, "European Patent Application No. 11164237. 7" (Certified Copy—Priority Document),:1-170 (Apr. 29, 2011).

European Patent Office, "Extended European Search Report—EP Application No. 11160251.2":1-10 (Sep. 14, 2011) Fellows, E.

Fellouse, F., et al., "Synthetic antibodies from a four-amino-acid code: A dominant role for tyrosine in antigen recognition" PNAS USA 101(34):12467-12472 (Aug. 24, 2004).

Ferrara, C., et al., "Modulation of therapeutic antibody effector functions by glycosylation engineering: influence of Golgi enzyme localization domain and co-expression of heterologous beta1, 4-N-acetylglucosaminyltransferase III and Golgi alpha-mannosidase II" Biotechnol Bioeng 93(5):851-861 (Jan. 24, 2006).

Ferrara, N., et al., "Clinical applications of angiogenic growth factors and their inhibitors" Nat Med 5(12):1359-1364 (Dec. 1, 1999).

Finger, R., et al., "Treatment patterns, visual acuity and quality-of-life outcomes of the WAVE study—A noninterventional study of ranibizumab treatment for neovascular age-related macular degeneration in Germany" Acta Ophthalmol 91(6):540-546 (Sep. 1, 2013).

Fischer, N., et al., "Bispecific antibodies: Molecules that enable novel therapeutic strategies" Pathobiology 74(1):3-14 (May 21, 2007).

Flatman, S., et al., "Process analytics for purification of monoclonal antibodies" J Chromatogr 848(1):79-87 (Mar. 15, 2007).

Fridman, W., "Fc receptors and immunoglobulin binding factors" FASEB J 5(12):2684-2690 (Sep. 1, 1991).

Fuhrmann, U., et al., "Inhibitors of Oligosaccharide Processing" Biochim Biophys Acta 825(2):95-110 (Jun. 24, 1985).

Fujimori, K., et al., "A Modeling Analysis of Monoclonal Antibody Percolation Through Tumors: A Binding Site Barrier" J Nuc Med 31(7):1191-1198 (Jul. 1, 1990).

Gavin, A., et al. The Immunoglobulin Receptors and their Physiological and Pathological Roles in Immunity "Chapter 2: Molecular basis for the interaction of Fc receptors with immunoglobulins" Winkel , J and Hogarth, P., eds., First edition, Dordrecht, NL:Springer Dordrecht,:11-35 (Aug. 31, 1998).

Gazzano-Santoro, H., et al., "A non-radioactive complement-dependent cytotoxicity assay for anti-CD20 monoclonal antibody" J Immunol Methods 202(2):163-171 (Mar. 28, 1997).

Geisse, S. et al., "Eukaryotic Expression Systems: A Comparison" Protein Expres Purif 8(3):271-282 (Nov. 1, 1996).

Gergly, J., et al., "Fc Receptors on Lymphocytes and K Cells" Biochem Soc Trans 12(5):739-743 (Oct. 1, 1984).

Gerngross, T.,, "Advances in the production of human therapeutic proteins in yeasts and filamentous fungi" Nat Biotechnol 22(11):1409-1414 (Nov. 4, 2004).

Gessner, J., et al., "The IgG Fc Receptor Family" Ann Hematol 76(6):231-248 (Jun. 1, 1998).

Ghebrehiwet, B., et al., "Isolation, cDNA cloning, and overexpression of a 33-kD cell surface glycoprotein that binds to the globular 'heads' of Clq" J Exp Med 179(6):1809-1821 (Jun. 1, 1994).

Ghetie, V. et al., "FcRn: the MHC class I-related receptor that is more than an IgG transporter" Immunol Today 18(12):592-598 (Dec. 1, 1997).

Ghetie, V. et al., "Increasing the serum persistence of an IgG fragment by random mutagenesis" Nat Biotechnol 15(7):637-640 (Jul. 1, 1997).

Ghetie, V., et al., "Abnormally short serum half-lives of IgG in β2-microglobulin-deficient mice" Eur J Immunol 26(3):690-696 (Mar. 1, 1996).

Ghetie, V.,, "Multiple roles for the major histocompatibility complex class I- related receptor FcRn" Ann Rev Immunol 18:739-766 (Apr. 1, 2000).

Gilles, R., et al., "MRI of the tumor microenvironment" J Magn Reson Imaging 16(4):430-450 (Sep. 25, 2002).

Glennie, M., et al., "Clinical Trials of Antibody Therapy" Immunol Today—Cell Press 21(8):403-410 (Aug. 1, 2000).

Goding, J. Monoclonal Antibodies: Principles and Practice "Chapter 2: Production and Application of Monoclonal Antibodies in Cell Biology, Biochemistry and Immunology" Second edition, London, GB:Academic Press,:56-103 (Jan. 1, 1986).

Gohil, R., et al., "Caregiver Burden in Patients Receiving Ranibizumab Therapy for Neovascular Age Related Macular Degeneration" PLOS One 10(6):e0129361 (1-13) (Jun. 9, 2015).

Gorman, C., et al., "Transient Production of Proteins Using an Adenovirus Transformed Cell Line" DNA Prot Eng Tech 2(1):3-10 (Jan. 1, 1990).

Graham, F., et al., "A new technique for the assay of infectivity of human adenovirus 5 DNA" Virology 52(2):456-467 (Apr. 1, 1973).

Graham, F., et al., "Characteristics of a Human Cell Line Transformed by DNA from Human Adenovirus Type 5" J Gen Virol 36(1):59-72 (Jul. 1, 1977).

Greenwood, J., et al., "Engineering multiple-domain forms of the therapeutic antibody CAMPATH-1H: effects on complement lysis" Therapeutic Immunology 1(5):247-255 (Oct. 1, 1994).

Greenwood, J., et al., "Structural motifs involved in human IgG antibody effector functions" Eur J Immunol 23(5):1098-1104 (May 1, 1993).

Griffiths, A., et al., "Human anti-self antibodies with high specificity from phage display libraries" EMBO J 12(2):725-734 (Feb. 1, 1993).

Groenink, J., et al., "On the interaction between agalactosyl IgG and Fcγ receptors" Eur J Immunol 26(6):1404-1407 (Jun. 1, 1996).

Gruber, M. et al., "Efficient tumor cell lysis mediated by a bispecific single chain antibody expressed in *Escherichia coli*" J Immunol 152(11):5368-5374 (Jun. 1, 1994).

Guddat, L., et al., "Three-dimensional structure of a human immunoglobulin with a hinge deletion" PNAS USA 90(9):4271-4275 (May 1, 1993).

Gurbaxni, B., et al., "Development of new models for the analysis of Fc-FcRn interactions" Mol Immunol 43(p):1379-1389 (Mar. 1, 2006).

Guyer, R., et al., "Immunoglobulin binding by mouse intestinal epithelial cell receptors" J Immunol 117(2):587-593 (Aug. 1, 1976).

Haagen, I., et al., "Interaction of Human Monocyte Fcγ Receptors with Rat IgG2b: A New Indicator for the FcγRIIa (R-H131) Polymorphism" J Immunol 154(4):1852-1860 (Feb. 15, 1995).

Hadley, A., et al., "The functional activity of FcγRII and FcγRIII on subsets of human lymphocytes" Immunology 76(3):446-451 (Jul. 1, 1992).

Hammes, H., et al., "Angiopoietin-2 causes pericyte dropout in the normal retina—Evidence for involvement in diabetic retinopathy" Diabetes 53(4):1104-1110 (Apr. 1, 2004).

(56)          References Cited

OTHER PUBLICATIONS

Hand, P., et al., "Comparative Biological Properties of a Recombinant Chimeric Anti-Carcinoma mAb and a Recombinant Aglycosylated Variant" Cancer Immunol Immunother 35(3):165-174 (May 1, 1992).

Harlow, E., et al. Antibodies. A Laboratory Manual "Chapter 14: Immunoassay" First edition, New York, USA:Cold Spring Harbor Laboratory,:553-612 (Jan. 1, 1988).

Harris, L., et al., "Crystallographic Structure of an Intact IgG1 Monoclonal Antibody" J Mol Biol 275(5):861-872 (Feb. 6, 1998).

Harris, L., et al., "Refined Structure of an Intact IgG2a Monoclonal Antibody" ACS Biochemistry 36(7):1581-1597 (Feb. 18, 1997).

Hashim, O., et al., "Role of Processing of N-Linked Oligosaccharides in Control of Immunoglobulin Secretion from Rat Hybridomas" Mol Immunol 24(10):1087-1096 (Oct. 1, 1987).

Hashim, O., et al., "Simultaneous Inhibition of Multiple Steps in the Processing of N-Linked Oligosaccharides Does Not Impair Immunoglobulin Secretion From Rat Hybridoma Cells." Immunology 63(3):383-388 (Mar. 1, 1988).

Hatta, Y., et al., "Association of Fcγ Receptor IIIB, But Not of Fcγ Receptor IIA and IIIA, Polymorphisms with Systemic Lupus Erythematosus in Japanese." Genes Immun 1(1):53-60 (Sep. 29, 1999).

He, F., et al., "High-throughput dynamic light scattering methods for measuring visosity of concentrated protein solutions" Anal Biochem 399(1):141-143 (Apr. 1, 2010).

Heier, J., et al., "Intravitreal Aflibercept (VEGF Trap-Eye) in Wet Age-related Macular Degeneration" Ophthalmology 119(12):2537-2548 (Dec. 1, 2012).

Heiken, H et al., "T lymphocyte development in the absence of Fcε receptor Iγ subunit: analysis of thymic-dependent and independent αβ and γδ pathways" Eur J Immunol 26(8):1935-1943 (Aug. 1, 1996).

Hellstrom, I., et al., "Antitumor effects of L6, an IgG2a antibody that reacts with most human carcinomas" PNAS USA 83(18):7059-7063 (Sep. 1, 1986).

Hellstrom, I., et al., "Strong antitumor activities of IgG3 antibodies to a human melanoma-associated ganglioside" PNAS USA 82(5):1499-1502 (Mar. 1, 1985).

Henry, A., et al., "Participation of the N-terminal region of Cε3 in the binding of human IgE to its high-affinity receptor FεRI" ACS Biochemistry 36(50):15568-15578 (Dec. 16, 1997).

Herter, G., et al., "GA101 P329GLALA, a variant of obinutuzumab with abolished ADCC, ADCP and CDC function but retained cell death induction, is as efficient as rituximab in B-cell depletion and antitumor activity" Haematologica 103(2):e78-e81 (Feb. 1, 2018).

Hessell, A. et al., "Fc receptor but not complement binding is important in antibody protection against HIV" Nature 446:101-105 ( 2007).

Hezareh, M. et al., "Effector function activities of a panel of mutants of a broadly neutralizing antibody against human immunodeficiency virus type 1" J Virol 75(24):12161-12168 (Dec. 15, 2001).

Hills, A., et al., "Metabolic control of recombinant monoclonal antibody N-glycosylation in GS-NS0 cells" Biotechnol Bioeng 75(2):239-251 (Oct. 20, 2001).

Hinman, L. et al., "Preparation and characterization of monoclonal antibody conjugates of the calicheamicins: A novel and potent family of antitumor antibiotics" Cancer Res 53(14):3336-3342 (Jul. 15, 1993).

Hinton, P. et al., "Engineered human IgG antibodies with longer serum half-lives in primates" J Biol Chem 279(8):6213-6216 (Feb. 20, 2004).

Hinton, P., et al., "An Engineered Human IgG1 Antibody with Longer Serum Half-life" J Immunol 176(1):346-356 (Jan. 1, 2006).

Hobbs, S., et al., "Interaction of Aglycosyl Immunoglobulins with the IgG Fc Transport Receptor From Neonatal Rat Gut: Comparison of Deglycosylation by Tunicamycin Treatment and Genetic Engineering." Mol Immunol 29(7-8):949-956 (Jul. 31, 1992).

Hogarth, P., et al., "Characterization of FcR Ig-binding sites and epitope mapping" Immunomethods 4(1):17-24 (Feb. 1, 1994).

Holliger, P., et al., "Diabodies': Small bivalent and bispecific antibody fragments" PNAS USA 90(14):6444-6448 (Jul. 15, 1993).

Holliger, P., et al., "Engineered antibody fragments and the rise of single domains" Nat Biotechnol 23(9):1126-1136 (Sep. 7, 2005).

Holz, F., et al., "Multi-country real-life experience of anti-vascular endothelial growth factor therapy for wet age-related macular degeneration" Br J Ophthalmol 99(2):220-226 (Feb. 1, 2015).

Hoogenboom, H., et al., "Overview of antibody phage-display technology and its applications" Methods Mol Biol 178:1-37 (Jan. 1, 2002).

Hudson, P., et al., "Engineered antibodies" Nat Med 9(1):129-134 (Jan. 1, 2003).

Hudziak, R., et al., "p185HER2 monoclonal antibody has antiproliferative effects in vitro and sensitizes human breast tumor cells to tumor necrosis factor" Mol Cell Biol 9(3):1165-1172 (Mar. 1, 1989).

Huizinga, T., et al., "Binding Characteristics of Dimeric IgG Subclass Complexes to Human Neutrophils" J Immunol 142(7):2359-2364 (Apr. 1, 1989).

Hutchins, J. et al., "Improved biodistribution, tumor targeting, and reduced immunogenicity in mice with a immunogenicity in mice with a γ4 variant of Campath-1H4 variant of Campath-1H" PNAS USA 92(26):11980-11984 (Dec. 19, 1995).

Idusogie, E.E. et al., "Engineered Antibodies with Increased Activity to Recruit Complement" J Immunol 166(4):2571-2575 (Feb. 15, 2001).

Idusogie, E.E. et al., "Mapping of the C1q Binding Site on Rituxan, A Chimeric Antibody with a Human IgG1 Fc" J Immunol 164(8):4178-4184 (Apr. 15, 2000).

International Preliminary Report on Patentability for PCT/EP2019/079137 issued Apr. 27, 2021, Wagner.

International Search Report for PCT/EP2019/079137 mailed on Jan. 16, 2020, Wagner.

"International Search Report—PCT/EP2012/055393" (w/Written Opinion),:pp. 1-15 (May 15, 2012), Fellows , E.

"International Search Report—PCT/EP2020/072088" (w/Written Opinion),:1-21 (Nov. 10, 2020), Wittzmann-Regis.

"International Search Report—PCT/US2002/033739":pp. 1-2 (Jun. 16, 2003), Huynn.

Israel, E., et al., "Increased clearance of IgG in mice that lack β2-microglobulin: possible protective role of FcRn" Immunology 89(4):573-578 (Dec. 1, 1996).

Jaakola, K., et al., "In vivo detection of vascular adhesion protein-1 in experimental inflammation" Am J Pathol 157(2):463-471 (Aug. 1, 2000).

Jackson, T., et al., "Human Retinal Molecular Weight Exclusion Limit and Estimate of Species Variation" Invest Ophthalmol Vis Sci 44(5):2141-2146 (May 1, 2003).

Janeway, C.A. et al., "Structural Variation in Immunoglobulin Constant Regions: Immunobiology: The Immune System in Health and Disease" Current Biology Ltd/Garland Publishing Inc. (.),:1-4 ( 1994).

Jang, Y., et al., "The structural basis for DNA binding by an anti-DNA autoantibody" Mol Immunol 35(18):1207-1217 (Dec. 15, 1998).

Jarvis, D., et al., "Biochemical Analysis of the N-Glycosylation Pathway in Baculovirus-Infected Lepidopteran Insect Cells" Virology 212(2):500-511 (Oct. 1, 1995).

Jassal, R.,, "Sialylation of Human IgG-Fc Carbohydrate by Transfected Rat α2,6-Sialyltransferase" Biochem Biophys Res Commun 286(2):243-249 (Aug. 17, 2001).

Jaumdally, R., et al., "Systemic and intracardiac vascular endothelial growth factor and angiopoietin-1 and -2 levels in coronary artery disease: Effects of angioplasty" Ann Med 39(4):298-305 (Feb. 9, 2007).

Jefferis, R., et al., "A Comparative Study of the N-Linked Oligosaccharide Structures of Human IgG Subclass Proteins" Biochem J 268(3):529-537 (Jun. 15, 1990).

Jefferis, R., et al., "IgG-Fc-Mediated Effector Functions: Molecular Definition of Interaction Sites for Effector Ligands and the Role of Glycosylation." Immunol Rev 163(1):59-76 (Jun. 1, 1998).

Jefferis, R., et al., "Molecular Definition of Interaction Sites on Human IgG for Fc Receptors (huFcγR)" Mol Immunol 27(12):1237-1240 (Dec. 1, 1990).

(56) References Cited

OTHER PUBLICATIONS

Jefferis, R., et al., "Recognition sites on human IgG for Fcγ receptors: the role of glycosylation" Immunol Lett 44(2-3):111-117 (Jan. 2, 1995).

Jefferis, R.,, "Interaction sites on human IgG-Fc for FcγR: current models" Immunol Lett 82(1-2):57-65 (Jun. 1, 2002).

Jeffrey, C., et al., "Dipeptide-based highly potent doxorubicin antibody conjugates" Bioorganic Med Chem Letters 16(2):358-362 (Jan. 15, 2006).

Jendreyko, N. et al., "Phenotypic Knockout of VEGF-R2 and Tie-2 with an Intradiabody Reduces Tumor Growth and Angiogenesis in Vivo" PNAS 102(23):8293-8298 (May 31, 2005).

Jendreyko, N. et al., "Simultaneous, Phenotypic Knockout of VEGF-R2 and Tie-2 with an Intradiabody Enhances Antiangiogenic Effects in Vivo" Klin Padiatr 218(3):143-151 (May 31, 2006).

Jensen, M., et al., "Rapid tumor lysis in a patient with B-cell chronic lymphocytic leukemia and lymphocytosis treated with an anti-CD20 monoclonal antibody (IDEC-C2B8, rituximab)" Ann Hematol 77(1-2):89-91 (Aug. 1, 1998).

Jones, E., et al., "The mechanism of intestinal uptake and transcellular transport of IgG in the neonatal rat" J Clin Invest 51(11):2916-2927 (Nov. 1, 1972).

Jorgensen, L., et al., "Recent trends in stabilising peptides and proteins in pharmaceutical formulation—considerations in the choice of excipients" Expert Opin Drug Deliv 6(11):1219-1230 (Nov. 1, 2009).

Jumper, J.M., et al., "Anti-VEGF treatment of macular edema associated with retinal vein occlusion: patterns of use and effectiveness in clinical practice (ECHO study report 2)" Clin Ophthalmol 12:621-629 (Apr. 3, 2018).

Kabat, EA et al. Sequences of Proteins of Immunological Interest (Table of Contents, Introduction and Constant Region Sequences sections), 5th edition, Bethesda, MD:NIH, vol. 1:647-723 ( 1991), 11 pgs.

Kabat, EA et al. Sequences of Proteins of Immunological Interest Fifth edition,NIH Publication, 647-723 (1991).

Kam, N. et al., "Carbon nanotubes as multifunctional biological transporters and near-infrared agents for selective cancer cell destruction" PNAS USA 102(33):11600-11605 (Aug. 16, 2005).

Kamei, D., et al., "Quantitative methods for developing Fc mutants with extended half-lives" Biotechnol Bioeng 92(6):748-760 (Dec. 20, 2005).

Kaneko, E., et al., "Optimizing therapeutic antibody function progress with Fc domain engineering" Biodrugs 25(1):1-11 (Sep. 15, 2011).

Kaneko, Y., et al., "Anti-inflammatory activity of immunoglobulin G resulting from Fc sialylation" Science 313(5787):670-673 (Aug. 4, 2006).

Kashmiri, S., et al., "SDR grafting—a new approach to antibody humanization" Methods 36:25-34 (Jan. 1, 2005).

Kaufman R.J., "Overview of Vector Design for Mammalian Gene Expression" Mol Biotechnol 16(2):151-160 (Oct. 1, 2000).

Kaushal, G., Methods in Enzymology—Guide to Techniques in Glycobiology "Chapter 19: Glycosidase inhibitors in study of glycoconjugates" Lennarz, W. & Hart, G., eds., First edition, Cambridge, MA—USA:Academic Press, vol. 230:316-329 (Jan. 17, 1994).

Kienast, Y., et al., "Ang-2-VEGF-A CrossMab, a Novel Bispecific Human IgG1 Antibody Blocking VEGF-A and Ang-2 Functions Simultaneously, Mediates Potent Antitumor, Antiangiogenic, and Antimetastatic Efficacy" Clin Cancer Res 19(24):6730-6740 (Dec. 15, 2013).

Kilmartin, J., et al., "Rat Monoclonal Antitubulin Antibodies Derived by Using a New Nonsecreting Rat Cell Line" J Cell Biol 93(3):576-582 (Jun. 1, 1982).

Kim, H et al., "FcRn receptor-mediated pharmacokinetics of therapeutic IgG in the eye" Mole Vision 15:2803-2812 (Dec. 16, 2009).

Kim, J., et al., "Catabolismof the Murine IgG1 Molecule: Evidence That Both CH2-CH3 Domain Interfaces are Required for Persistence of IgG1 in the Circulation of Mice" Scand J Immunol 40(4):457-465 (Oct. 1, 1994).

Kim, J., et al., "Identifying amino acid residues that influence plasma clearance of murine IgG1 fragments by site-directed mutagenesis" Eur J Immunol 24(3):542-548 (Mar. 1, 1994).

Kim, J., et al., "Localization of the site of the murine IgG1 molecule that is involved in binding to the murine intestinal Fc receptor" Eur J Immunol 24(10):2429-2434 (Oct. 1, 1994).

Kim, J., et al., "Mapping the site on human IgG for binding of the MHC class I-related receptor, FcRn" Eur J Immunol 29(9):2819-2825 (Sep. 1, 1999).

Kim, J., et al., "The Vascular Endothelial Growth Factor Proteins: Identification of Biologically Relevant Regions by Neutralizing Monoclonal Antibodies" Growth Factors 7(1):53-64 (Jan. 1, 1992).

Kim, K., et al., "Inhibition of vascular endothelial growth factor-induced angiogenesis suppresses tumour growth in vivo" Nature 362(6423):841-844 (Apr. 29, 1993).

Kindt, T., et al. Kuby Immunology "Part II: Generation of B-Cell and T-Cell Response, Chapter 4: Antigen and Antibodies" Kindt, T., Goldsby, R., eds, Sixth edition, New York, N.Y.—USA:W. H. Freeman and Company,:91 ( 2007).

King, D., et al., "Recombinant Antibodies for the Diagnosis and Therapy of Human Disease." Curr Opin Drug Discovery Develop 2(2):110-117 (Mar. 1, 1999).

King, H., et al., "Monoclonal antibody conjugates of doxorubicin prepared with branched peptide linkers: Inhibition of aggregation by methoxytriethyleneglycol chains" ACS J Med Chem 45(19):4336-4343 (Aug. 14, 2002).

Klein, C., et al., "Abstract PR8: Novel tumor-targeted, engineered IL-2 variant (IL-2v)-based immunocytokines for immunotherapy of cancer" Cancer Res 73( Suppl 1):1-2 (Jan. 1, 2013).

Klein, C., et al., "Cergutuzumab amunaleukin (CEA-IL2v), a CEA targeted IL-2 variant-based immunocytokine for combination cancer immunotherapy: Overcoming limitations of aldesleukin and conventional IL-2- based immunocytokines" Oncoimmunology 6(3):e1277306 (1-15) (Jan. 11, 2017).

Klein, C., et al., "Novel Tumor-Targeted, Engineered IL-2 Variant (IL2v)-Based Immunocytokines for Immunotherapy of Cancer" Blood 122(21):2278-2278 (Nov. 15, 2013).

Klimka, A. et al., "Human anti-CD30 recombinant antibodies by guided phage antibody selection using cell panning" Brit J Cancer 83(2):252-260 (Jun. 15, 2000).

Kobayashi, H., et al., "Similarities in the biodistribution of iodine-labeled anti-tac single-chain disulfide-stabilized Fv fragment and anti-tac disulfide-stabilized Fv fragment" Nucl Med Biol 25(4):387-393 (May 1, 1998).

Kobayashi, H., et al., "Tryptophan H33 plays an important role in pyrimidin (6-4) pyrimidone photoproduct binding by a high-affinity antibody" Protein Eng 12(10):879-884 (Oct. 1, 1999).

Koene, H., et al., "FcγRIIIa-158V/F Polymorphism Influences the Binding of the IgG by Natural Killer Cell FcγRIIIa, Independently of the FcγRIIIa-48L/R/H Phenotype" Blood 90(3):1109-1114 (Aug. 1, 1997).

Kohler, C., et al., "Continuous cultures of fused cells secreting antibody of predefined specificity" Nature 256(5517):495-497 (Aug. 7, 1975).

Kojima, N., et al., "Alpha 1,6-linked fucose affects the expression and stability of polysialic acid-carrying glycoproteins in chinese hamster ovary cells" J Biochem 124(4):726-737 (Oct. 1, 1998).

Kojima, N., et al., "Characterization of Mouse ST8Sia II (STX) as a Neural Cell Adhesion Molecule-specific Polysialic Acid Synthase" J Biol Chem 271(32):19457-19463 (Aug. 1, 1996).

Kostelny, S., et al., "Formation of a bispecific antibody by the use of leucine zippers" J Immunol 148(5):1547-1553 (Mar. 1, 1992).

Kozbor, D., et al., "A human hybrid myeloma for production of human monoclonal antibodies" J Immunol 133(6):3001-3005 (Dec. 1, 1984).

Kratz, F., et al., "Prodrugs of anthracyclines in cancer chemotherapy" Curr Med Chem 13(5):477-523 (Mar. 1, 2006).

Krummen et al., "Executive Summary Engineering CHO Cells to Maximize Sialic Acid Content of Recombinant Glycoproteins"

(56) References Cited

OTHER PUBLICATIONS

Other Cambridge Healthtech Institute's Fourth Annual Protein Expression Meeting, Hilton McLean, Tysons' Corner, McLean Virginia, ( Apr. 5-6, 2001).

Kumpel, B., et al., "Galactosylation of human IgG monoclonl anti-D produced by EBV-transformed B-lymphoblastoid cell lines is dependent on culture method and affects Fc receptor-mediated functional activity" Hum Antibodies Hybridomas 5(3):143-151 (Jan. 1, 1994).

Kunkel, T.,, "Rapid and Efficient Site-Specific Mutagenesis Without Phenotypic Selection" PNAS 82(2):488-492 (Jan. 1, 1985).

Kuo, T., et al., "Neonatal Fc Receptor: From Immunity to Therapeutics" J Clin Immunol 30(6):777-789 (Oct. 1, 2010).

Laurak, V., et al., "Identification and Characterisation of C1q-Binding Phage Displayed Peptides" Biochemistry—US 378(12):1509-1519 (Dec. 1, 1997).

LAZAR, G. et al., "Engineered antibody Fc variants with enhanced effector function" PNAS 103(11):4005-4010 (Mar. 14, 2006).

Leatherbarrow, R., et al., "Effector Functions of a Monoclonal Aglycosylated Mouse IgGZa: Binding and Activation of Complement Component C1 and Interaction with Human Monocyte Fc Receptor." Mol Immunol 22(4):407-415 (Apr. 1, 1985).

Lee, C. et al., "High-affinity human antibodies from phage-displayed synthetic Fab libraries with a single framework scaffold" J Mol Biol 340(5):1073-1093 ( 2004).

Lee, C., et al., "Bivalent antibody phage display mimics natural immune globulin" J Immunol Methods 284(1-2):119-132 (Jan. 1, 2004).

Lehrnbecher, T., et al., "Variant genotypes of FcγRIIIA influence the development of Kaposi's sarcoma in HIV-infected men" Blood 95(7):2386-2390 (Apr. 1, 2000).

Lehrnbecher, T., et al., "Variant Genotypes of the Low-Affinity Fcγ Receptors in Two Control Populations and a Review of Low-Affinity Fcγ Receptor Polymorphisms in Control and Disease Populations" Blood 94(12):4220-4232 (Dec. 15, 1999).

Levy, J., et al., "Human Lymphoblastoid Lines From Lymph Node and Spleen" Cancer 22(3):517-524 (Sep. 1, 1968).

Li et al., "Safety and Efficacy of Conbercept in Neovascular Age-Related Macular Degeneration" Ophthalmology 121:1740-1747 ( 2014).

Li, H., et al., "Optimization of humanized IgGs in glycoengineered Pichia pastoris" Nat Biotechnol 24(2):210-215 (Feb. 1, 2006).

Li, J., et al., "Human antibodies for immunotherapy development generated via a human B cell hybridoma technology" PNAS USA 103(10):3557-3562 (Mar. 7, 2006).

Li, M., et al., "Reconstitution of human FcγRIII cell type specificity in transgenic mice" J Exp Med 183(3):1259-1263 (Mar. 1, 1996).

Liang, W., et al., "Cross-Species Vascular Endothelial Growth Factor (VEGF)-Blocking Antibodies Completely Inhaibit the Growth of Human Turnor Xenografts and Measure the Contribution of Stromal VEGF" J Biol Chem 28(2):951-961 (Jan. 13, 2006).

Lieu, C., et al., "Safety and Efficacy of MPDL3280A (Anti-PDL1) in Combination with Bevacizumab (BEV) and/or Chemotherapy (Chemo) in Patients (PTS) with Locally Advanced or Metastatic Solid Tumors" Ann Oncol 25( SUPPL 4):iv361 (Sep. 1, 2014).

Lifely, M. et al., "Glycosylation and Biological Activity of CAMPATH-1H Expressed in Different Cell Lines and Grown Under Different Culture Conditions." Glycobiology 5(8):813-822 (Dec. 1995).

Lin, P., et al., "Inhibition of tumor angiogenesis using a soluble receptor establishes a role for Tie2 in pathologic vascular growth" J Clin Invest 100(8):2072-2078 (Oct. 15, 1997).

Liu, J., et al., "Characterization of Complex Formation by Humanized Anti-IgE Monoclonal Antibody and Monoclonal Human IgE" ACS Biochemistry 34(33):10474-10482 (Aug. 22, 1995).

Liu, J., et al., "Reversible Self-Association Increases the Viscosity of a Concentrated Monoclonal Antibody in Aqueous Solution" J Pharm Sci 94(9):1928-1940 (Sep. 1, 2005).

Liu, L., et al., "The BRAF and MEK Inhibitors Dabrafenib and Trametinib: Effects on Immune Function and in Combination with Immunomodulatory Antibodies Targeting PD-1, PD-L1, and CTLA-4" Clin Cancer Res 21(7):1639-1651 (Apr. 1, 2015).

Lo, M., et al., "Effector-attenuating Substitutions That Maintain Antibody Stability and Reduce Toxicity in Mice" J Biol Chem 292(9):3900-3908 (Mar. 3, 2017).

Lode, H., et al., "Targeted therapy with a novel enediyene antibiotic calicheamicin θ_1 effectively suppresses growth and dissemination of liver metastases in a syngeneic model of murine neuroblastoma" Cancer Res 58(14):2925-2928 (Jul. 15, 1998).

Lonberg, N., et al., "Fully human antibodies from transgenic mouse and phage display platforms" Curr Opin Immunol 20(4):450-459 (Aug. 1, 2008).

Lonberg, N.,, "Human antibodies from transgenic animals" Nat Biotechnol 23(9):1117-1125 (Sep. 7, 2005).

Lorenz, A., et al., "Strong Association Between the Responder Status of the FCγII Receptor and Recurrent Spontaneous Abortion." Eur J Immunogenet 22(5):397-401 (Oct. 1, 1995).

Loyet, K., et al., "Technology comparisons for anti-therapeutic antibody and neutralizing antibody assays in the context of an anti-TNF pharmacokinetic study" J Immunol Methods 345(1-2):17-28 (Jun. 30, 2009).

Lu, D., et al., "A fully human recombinant IgG-like bispecific antibody to both the epidermal growth factor receptor and the insulin-like growth factor receptor for enhanced antitumor activity" J Biol Chem 280(20):19665-19672 (May 20, 2005).

Lu, D., et al., "Simultaneous blockade of both the epidermal growth factor receptor and the insulin-like growth factor receptor signaling pathways in cancer cells with a fully human recombinant bispecific antibody" J Biol Chem 279(4):2856-2865 (Jan. 23, 2004).

Lucas, B. et al., "High-level production of recombinant proteins in CHO cells using a dicistronic DHFR intron expression vector" Nucleic Acids Res 24(9):1774-1779 (May 1, 1996).

Lund, J. et al., "Human FcγRI and Fcγ RII interact with distinct but overlapping sites on human IgG" J Immunol 147(8):2657-2662 (Oct. 15, 1991).

Lund, J. et al., "Multiple binding sites on the CH2 domain of IgG for mouse FcγR11" Mol Immunol 29(1):53-59 (Jan. 1, 1992).

Lund, J., et al., "Multiple Interactions of the IgG with Its Core Oligosaccharide Can Modulate Recognition by Complement and Human Fcγ Receptor I and Influence the Synthesis of Its Oligosaccharide Chains" J Immunol 157:4963-4969 (Dec. 1, 1996).

Lund, J., et al., "Oligosaccharide-protein interactions in IgG can modulate recognition by Fcγ receptors" FASEB J 9(1):115-119 (Jan. 1, 1995).

Mabry, R., et al., "Engineering of stable bispecific antibodies targeting IL-17A and IL-23" Preotein Eng Des Select 23(3):115-127 (Mar. 1, 2010).

Mac Callum, R., et al., "Antibody-antigen Interactions: Contact Analysis and Binding Site Topography" J Mol Biol 262(5):732-745 (Oct. 11, 1996).

Macher, B., et al., "Proteins at membrane surfaces—a review of approaches" Mol Biosyst 3(10):705-713 (Aug. 21, 2007).

Maguire, M., et al., "Five-Year Outcomes with Anti-Vascular Endothelial Growth Factor Treatment of Neovascular Age-Related Macular Degeneration: The Comparison of Age-Related Macular Degeneration Treatments Trials" Ophthalmology 123(8):1751-1761 (May 1, 2016).

Makrides, S., et al., "Components of Vectors for Gene Transfer and Expression in mammalian cells" Protein Exp Purif 17(2):183-202 (Nov. 1, 1999).

Male, D. Immunology, An Illustrated Outline London:Gower Medical Publishing Ltd.,:21-24 ( 1986).

Malhotra, R., et al., "Glycosylation Changes of IgG Associated with Rheumatoid Arthritis Can Activate Complement Via the Mannose-Binding Protein" Nat Med 1(3):237-243 (Mar. 1, 1995).

Marionneau, S., et al., "Susceptibility of Rat Colon Carcinoma Cells to Lymphokine Activated Killer-Mediated Cytotoxicity is Decreased by α1,2-Fucosylation" Int J Cancer 86(5):713-717 (Jun. 1, 2000).

Marks, J. et al., "By-passing immunization: building high affinity human antibodies by chain shuffling" Bio/Technology 10(7):779-783 (Jul. 1, 1992).

(56) References Cited

OTHER PUBLICATIONS

Marks, J., et al. Methods Mol Biol "Chapter 8: Selection of Human Antibodies from Phage Display Libraries" Lo B.K.C. (eds), Totowa, New Jersey—US:Humana Press Inc., vol. 248:161-176 (Jan. 1, 2004).

Martin, "Ranibizumab and Bevacizumab for Treatment of Neovascular Age-Related Macular Degeneration: 2-Year Results:" Ophthalmology 119(7):1388-1398 ( 2012).

Martin, W., et al., "Crystal structure at 2.8 A of an FcRn/heterodimeric Fc complex: mechanism of pH-dependent binding" Mol Cell 7(4):867-877 (Apr. 1, 2001).

Masuda, K et al., "Enhanced binding affinity for FcγRIIIa of fucose-negative antibody is sufficient to induce maximal antibody-dependent cellular cytotoxicity" Molec Immunol 44(12):3122-3131 (May 1, 2007).

Mather, J., "Establishment and characterization of two distinct mouse testicular epithelial cell lines" Biol Reprod 23(1):243-252 (Aug. 1, 1980).

Mather, J., et al., "Culture of Testicular Cells in Hormone-Supplemented Serum-Free Medium" Ann NY Acad Sci 383:44-68 (Jan. 1, 1982).

Maxwell, K., et al., "Crystal structure of the human leukocyte Fc receptor, FcγRIIa" Nat Struct Biol 6(5):437-442 (May 1, 1999).

Mayo Clinic Staff, "Goiter" http://www.mayoclinic.com/health/goiter/DS00217/method (Sep. 9, 2011), 7 pgs.

Mc Cafferty, J., et al., "Phage antibodies: filamentous phage displaying antibody variable domains" Nature 348(6301):552-554 (Dec. 6, 1990).

McCarthy, K., et al., "Bidirectional transcytosis of IgG by the rat neonatal Fc receptor expressed in a rat kidney cell line: a system to study protein transport across epithelia" J Cell Sci 113(Pt. 7):1277-1285 (Apr. 1, 2000).

Medesan, C. et al., "Delineation of the amino acid residues involved in transcytosis and catabolism of mouse IgG1" J Immunol 158(5):2211-2217 (Mar. 1, 1997).

Medesan, C., et al., "Comparative studies of rat IgG to further delineate the Fc:FcRN interaction site" Eur J Immunol 28(7):2092-2100 (Jul. 1, 1998).

Medesan, C., et al., "Localization of the site of the IgG molecule that regulates maternofetal transmission in mice" Eur J Immunol 26(10):2533-2536 (Oct. 1, 1996).

Mellis, S., et al., "Structures of the Oligosaccharides Present at the Three Asparagine-Linked Glyosylation Sites of Human IgD" J Biol Chem 258(19):11546-11556 (Oct. 10, 1983).

Melnyk, O., et al., "Vascular endothelial growth factor promotes tumor dissemination by a mechanism distinct from its effect on primary tumor growth" Cancer Res 56(4):921-924 (Feb. 15, 1996).

Meng, Y., et al., "Green fluorescent protein as a second selectable marker for selection of high producing clones from transfected CHO cells" Gene 242(1-2):201-207 (Jan. 25, 2000).

Michaeli, Y. et al., "Optimised Fc variants with enhanced effector function" Expert Opinion Ther. Patents 16(10):1449-1452 (Oct. 4, 2006).

Mikayama, T., et al., "Molecular cloning and functional expression of a cDNA encoding glycosylation-inhibiting factor" PNAS USA 90(21):10056-10060 (Nov. 1, 1993).

Miller, K., et al., "A Novel Role for the Fc Receptor γ Subunit: Enhancement of the FcγR Ligand Affinity" J Exp Med 183(5):2227-2233 (May 1, 1996).

Miller, K., et al., "Design, Construction, and in Vitro Analyses of Multivalent Antibodies" J Immunol 170(9):4854-4861 (May 1, 2003).

Milstein, C., et al., "Hybrid hybridomas and their use in immunohistochemistry" Nature 305(5934):537-540 (Oct. 6, 1983).

Mimura, Y., et al., "The influence of glycosylation on the thermal stability and effector function expression of human IgG1-Fc: properties of a series of truncated glycoforms" Mol Immunol 37(12-13):697-706 (Aug. 31, 2000).

Mizushima et al., "Structural Basis for Improved Efficacy of Therapeutic Antibodies on Defucosylation of Their Fc Glycans" Genes to Cells 16:1071-1080 ( 2011).

Mojumder, N., et al., "The Mechanism of the Bispecific Antibody Faricimab Targeting VEGF-A and Ang2 has effect greater than targeting either alone" Retinal Physician 16:32-35 (Mar. 1, 2019).

Monkos, K.,, "Concentration and temperature dependence of viscosity in lysozyme aqueous solutions" Biochim Biophys Acta 1339(2):304-310 (May 23, 1997).

Mooney, M., "The viscosity of a concentrated suspension of spherical particles" J Colloid Sci 6(2):162-170 (Apr. 1, 1951).

Moore, G., et al., "Engineered Fc variant antibodies with enhanced ability to recruit complement and mediate effector functions" MABS 2(2):181-189 (Mar. 31, 2010).

Morgan, A, et al., "The N-terminal end of the CH2 domain of chimeric human IgG1 anti-HLA-DR is necessary for C1q, Fc gamma RI and Fc gamma RIII binding" Immunology 86(2):319-324 (Oct. 1, 1995).

Morris, I. Antigen Absorption by the Gut "Chapter 1: The receptor hypothesis of protein ingestion" Hemmings, W., ed., First edition, Baltimore, MD—USA: University Park Press,:3-22 (Jan. 1, 1978).

Morrison, S., et al., "Structural Determinants of Human IgG Function" The Immunologist 2/4:119-124 (Jan. 1, 1994).

Morrison, S., et al., "Variable Region Domain Exchange Influences the Functional Properties of IgG" J Immunol 160(6):2802-2808 (Mar. 15, 1998).

Morrison, S.,, "Two Heads are Better Than One—A new Design for Bispecific Antibodies Enables Efficient Production of Stable Molecules with Good Pharmacodynamic Properties." Nat Biotechnol 25(11):1233-1234 (Nov. 1, 2007).

Murray, R., et al. Harper's Biochemistry "Section I: Structures and Functions of Proteins and Enzymes—4-Amino Acids" Murray, R, Granner, D., eds., Twenty-third edition, Norwalk, Conn. USA:Appleton & Lange Publishers, Inc.,:23-28 (Jan. 1, 1993).

Murray, R., Human Biochemistry "Physiological Consequences of Changing of the Primary Structure" (Russian—Eng. Translation only), Moscow, RU:Mir, vol. 1:34 (Jan. 1, 1993).

Nagarajan, S., et al., "Ligand binding and phagocytosis by CD16 (Fc γ receptor III) isoforms. Phagocytic signaling by associated ( and γ subunits in Chinese hamster ovary cells" J Biol Chem 270(43):25762-25770 (Oct. 27, 1995).

Nagy, A., et al., "Stability of cytotoxic luteinizing hormone-releasing hormone conjugate (AN-152) containing doxorubicin 14-O-hemiglutarate in mouse and human serum in vitro: implications for the design of preclinical studies" PNAS USA 97(2):829-834 (Jan. 18, 2000).

Natsume, A., et al., "Improving Effector Functions of Antibodies for Cancer Treatement: Enhancing ADCC and CDC" Drug Des Devel Ther 3:7-16 (Sep. 21, 2009).

NCBI BLAST, NCBI Database, RID B6YPW2WD114—Protein Sequence, (Seq. ID No. 909; WO2006/076594; Amino Acid), pp. 1-3Release Date Apr. 14, 2019.

NCI BLAST, NCBI Database, RID-B1PVHH83114—Protein Sequence, (Seq ID No. 193; Amino Acid), pp. 1-2Release Date Apr. 12, 2019.

Newkirk, N., et al., "Rheumatoid factor avidity in patients with rheumatoid arthritis: identification of pathogenic RFs which correlate with disease parameters and with the gal(0) glycoform of IgG" J Clin Immunol 15(5):250-257 (Sep. 1, 1995).

Newman, R., et al., "Modification of the Fc region of a primatized IgG antibody to human CD4 retains its ability to modulate CD4 receptors but does not deplete CD4(+) T cells in chimpanzees" Clin Immunol 98(2):164-174 (Feb. 1, 2001).

Ngo, J. et al. The Protein Folding Problem and Tertiary Structure Prediction "Chapter 14: Computational Complexity and the Levinthal Paradox" Merz, K, & Grand, S., eds., First edition, Boston, MA—US:Birkhauser Publishers,:491-506 (Jan. 1, 1994).

Ni, J. et al., "Research progress and future perspectives in antibodomics and antibodomic drugs" Xiandai Mianyixue 26(4):265-268 ( 2006), abstract—translation.

Nieto, A., et al., "Involvement of the Fcγ receptor IIIA genotypes in susceptibility to rheumatoid arthritis" Arthritis Rheum 43(4):735-739 (Apr. 1, 2000).

(56)          References Cited

OTHER PUBLICATIONS

Niu, C.,, "FDA perspective on peptide formulation and stability issues" J Pharm Sci 87(11):1331-1334 (Nov. 1, 1998).

Niu, G., et al., "Human epidermal growth factor receptor 2 regulates angiopoietin-2 expression in breast cancer via AKT and mitogen-activated protein kinase pathways" Cancer Res 67(4):1487-1493 (Feb. 15, 2007).

Norderhaug, L., et al., "Versatile vectors for transient and stable expression of recombinant antibody molecules in mammalian cells" J Immunol Methods 204(1):77-87 (May 12, 1997).

Noren, C., et al., "A general method for site-specific incorporation of unnatural amino acids into proteins" Science 244(4901):182-188 (Apr. 14, 1989).

Nose, M., et al., "Biological Significance of Carbohydrate Chains on Monoclonal Antibodies" PNAS USA 80(21):6632-6636 (Nov. 1, 1983).

Notice of Opposition for Ecuadorian Application No. SP-2013-DIV-11-11139-D1 with English translation. (Mar. 6, 2015).

Ober, R., et al., "Differences in promiscuity for antibody—FcRn interactions across species: implications for therapeutic antibodies" Int Immunol 13(12):1551-1559 (Dec. 1, 2001).

Ober, R., et al., "Exocytosis of IgG as mediated by the receptor, FcRn: An analysis at the single-molecule level" PNAS USA 101(30):11076-11081 (Jul. 27, 2004).

Ober, R., et al., "Visualizing the site and dynamics of IgG salvage by the MHC class I-related receptor, FcRn" J Immunol 172(4):2021-2029 (Feb. 15, 2004).

Oganesyan, V. et al., "Structural characterization of a human Fc fragment engineered for extended serum half-life" Mol Immunol 46(8-9):1750-1755 (May 1, 2009).

Oganesyan, V., et al., "Structural characterization of a human Fc fragment engineered for lack of effector functions" Acta Crystallogr D Biol Crystallogr 64(Pt 6):700704 (May 14, 2008).

Ohyama, C., et al., "Molecular Cloning and Expression of GDP-d-mannose-4,6-dehydratase, a Key Enzyme for Fucose Metabolism Defective in Lec13 Cells" J Biol Chem 273(23):14582-14587 (Jun. 5, 1998).

Okada, H., et al., "Cutting Edge: Role of the Inositol Phosphatase SHIP in B Cell Receptor-Induced Ca2+ Oscillatory Response" J Immunol 161(10):5129-5132 (Nov. 15, 1998).

Okafo, G., et al., "Simple Differentiation Between Core-Fucosylated and Nonfucosylated Glycans by Capillary Electrophoresis" Anal Biochem 240(1):68-74 (Aug. 15, 1996).

Okazaki, A., et al., "Fucose depletion from human IgG1 Oligosaccharide enhances binding enthalpy and association rate between IgG1 and FcgammaRIIIa" J Mol Biol 336(5):1239-1249 (Mar. 5, 2004).

Olafsen, T., et al., "Tunable pharmacokinetics: modifying the in vivo half-life of antibodies by directed mutagenesis of the Fc fragment" Nat Protoc 1(4):2048-2060 (Nov. 30, 2006).

Oliner, J., et al., "Suppression of Angiogenesis and Tumor Growth by Selective Inhibition of Angiopoietin-2" Cancer Cell 6(5):507-516 (Nov. 1, 2004).

Ong, F., et al., "Personalized Medicine in Ophthalmology: From Pharmacogenetic Biomarkers to Therapeutic and Dosage Optimization" J Pers Med 3(1):40-69 (Mar. 5, 2013).

Ono, M., et al., "Deletion of SHIP or SHP-1 reveals two distinct pathways for inhibitory signaling" Cell 90(2):293-301 (Jul. 25, 1997).

Ono, M., et al., "Role of the inositol phosphatase SHIP in negative regulation of the immune system by the receptor FcγRIIIB" Nature 383(6597):263-266 (Sep. 19, 1996).

Orlandi, R., et al., "Cloning Immunoglobulin Variable Domains for Expression by the Polymerase Chain Reaction" PNAS USA 86(10):3833-3837 (May 1, 1989).

Osbourn, J. et al., "From rodent reagents to human therapeutics using antibody guided selection" Methods 36(1):61-68 (May 1, 2005).

O'Sullivan, M., et al., "Methods for the preparation of enzyme-antibody conjugates for use in enzyme immunoassay" Method Enzymol 73(Pt. B):147-166 (Jan. 1, 1981).

Padlan, E. et al., "A possible procedure for reducing the immunogenicity of antibody variable domains while preserving their ligand-binding properties" Mol Immunol 28(4-5):489-498 (Apr. 30, 1991).

Padlan, E., "Anatomy of the antibody molecule" Mol Immunol 31(3):169-217 (Feb. 1, 1994).

Pakula, A., et al., "Genetic analysis of protein stability and function" Annu Rev Genet 23:289-310 (Dec. 1, 1989).

Papac, D., et al., "Analysis of Acidic Oligosaccharides and Glycopeptides by Matrix-Assisted Laser Desorption/Ionization Time-of-Flight Mass Spectrometry" ACS Anal Chem 68(18):3215-3223 (Sep. 15, 1996).

Parekh, R., et al., "Association of rheumatoid arthritis and primary osteoarthritis with changes in the glycosylation pattern of total serum IgG" Nature 316(6027):452-457 (Aug. 1, 1985).

Paul, W., Fundamental Immunology "Chapter 9: Structure and Function of Immunoglobins" Paul, W., ed., Third edition, New York, N.Y.—US:Raven Press,:292-295 (Jan. 1, 1993).

Penichet, M., et al., "Antibody-Cytokine Fusion Proteins for the Therapy of Cancer" J Immunol Methods 248(1-2):91-101 (Feb. 1, 2001).

Petkoova, S., et al., "Enhanced half-life of genetically engineered human IgG1 antibodies in a humanized FcRn mouse model: potential application in humorally mediated autoimmune disease" Int Immunol 18(12):1759-1769 (Dec. 1, 2006).

Petrukhin, K.,, "New Therapeutic Targets in Atrophic Age-Related Macular Degeneration" Expert Opin Ther Targets 11(5):625-639 (May 1, 2007).

Pluckthun, A. et al. The Pharmacology of Monoclonal Antibodies "Antibodies from *Escherichia coli*" Rosenberg & Moore, vol. 113:269-315 ( 1994).

Popkov, M., et al., "Human/mouse cross-reactive anti-VEGF receptor 2 recombinant antibodies selected from an immune b9 allotype rabbit antibody library" J Immunol Methods 288(1-2):149-164 (May 1, 2004).

Popov, S., et al., "The stoichiometry and affinity of the interaction of murine Fc fragments with the MHC class I-related receptor, FcRn" Mol Immunol 33(6):521-530 (Apr. 1, 1996).

Porges, A., et al., "Novel Fcγ Receptor I Family Gene Products in Human Mononuclear Cells" J Clin Invest 90(5):2102-2109 (Nov. 1, 1992).

Portolano, S., et al., "Lack of promiscuity in autoantigen-specific H and L chain combinations as revealed by human H and L chain 'Roulette'" J Immunol 150(3):880-887 (Feb. 1, 1993).

Prabhat, P., et al., "Elucidation of intracellular recycling pathways leading to exocytosis of the Fc receptor, FcRn, by using multifocal plane microscopy" PNAS USA 104(14):5889-5894 (Mar. 23, 2007).

Praetor, A., et al., "Intracelluarl traffic of the MHC Class I-Like IgG Fc receptor, FcRn, expressed in epithelial MdCK Cells" J Cell Sci 112(Pt. 15):2291-2299 (Jul. 1, 1999).

Presta, L. et al., "Humanization of an antibody directed against IgE" J Immunol 151(5):2623-2632 (Sep. 1, 1993).

Presta, L., et al., "Engineering therapeutic antibodies for improved function" Biochem Soc Trans 30(4):487-490 (Aug. 1, 2002).

Presta, L., et al., "Humanization of An Anti-vascular Endothelial Growth Factor Monoclonal Antibody for the Therapy of Solid Tumors and Other Disorder" Cancer Res 57(20):4593-4599 (Oct. 15, 1997).

Presta, L., et al., "Molecular engineering and design of therapeutic antibodies" Curr Opin Immunol 20(4):460-470 (Aug. 1, 2008).

Presta, L.,, "Antibody engineering for therapeutics" Curr Opin Struc Biol 13(4):519-525 (Aug. 1, 2003).

Presta, L.,, "Engineering of therapeutic antibodies to minimize immunogenicity and optimize function" Adv Drug Deliver Rev 58(5-6):640-656 (Aug. 7, 2006).

Presta, L.,, "Selection, design, and engineering of therapeutic antibodies" J Allergy Clin Immun 116(4):731-736 (Oct. 1, 2005).

Qiao, S., et al., "Dependence of antibody-mediated presentation of antigen on FcRn" PNAS 105(27):9337-9342 (Jul. 1, 2008).

Queen, C., et al., "A humanized antibody that binds to the interleukin 2 receptor" PNAS USA 86(24):10029-10033 (Dec. 1, 1989).

(56) References Cited

OTHER PUBLICATIONS

Radaev, S., et al., "The Structure of a Human Type III Fcγ Receptor in Complex with Fc" J Bio Chem 276(19):16469-16477 (May 11, 2001).

Raghavan, M. et al., "Analysis of the pH dependence of the neonatal Fc receptor/immunoglobulin G interaction using antibody and receptor variants" ACS Biochemistry 34(45):14649-14657 (Nov. 14, 1995).

Raghavan, M.,, "Fc receptors and their interactions with immunoglobulins" Annu Rev Cell Dev Biol 12:181-220 (Nov. 1, 1996).

Rajagopal, V.,, "A Form of Anti-Tac(Fv) Which is Both Single-chain and Disulfide Stabilized: Comparison with its Single-chain and Disulfide-stabilized Homologs" Protein Eng 10(12):1453-1459 (Dec. 1, 1997).

Raju, T et al., "Species-Specific Variation in Glycosylation of IgG: Evidence for the Species-Specific Sialylation and Branch-Specific Galactosylation and Importance for Engineering Recombinant Glycoprotein Therapeutics." Glycobiology 10(5):477-486 (May 1, 2000).

Rao, P., et al., "Real-World Vision in Age-Related Macular Degeneration Patients Treated with Single Anti-VEGF Drug Type for 1 Year in the IRIS Registry" Ophthalmology 125(4):522-528 (Apr. 1, 2018).

Ravetch, J. et al., "IgG Fc receptors" Ann Rev Immunol 19:275-290 (Apr. 1, 2001).

Ravetch, J., et al., "Divergent roles for Fc receptors and complement in vivo" Annu Rev Immunol 16:421-432 (Apr. 1, 1998).

Ravetch, J., et al., "Fc receptors" Annu Rev Immunol 9:457-492 (Apr. 1, 1991).

Ravetch, J., "Fc receptors" Curr Opin Immunol 9(1):121-125 (Feb. 1, 1997).

Ravetch, J., "Fc receptors: rubor redux" Cell 78(4):553-560 (Aug. 26, 1994).

Reff, M.E. et al., "Depletion of B cells in vivo by a chimeric mouse human monoclonal antibody to CD20" Blood 83(2):435-445 (Jan. 15, 1994).

Repp et al., "Combined Fc-Protein- and Fc-Glyco-Engineering of scFv-Fc Fusion Proteins Synergistically Enhances CD16a Binding but Does Not Further Enhance NK-Cell Mediated ADCC" J Immunol Methods 373(1-2):67-78 (Oct. 28, 2011).

Ridgway et al., "'Knobs-into-holes' engineering of antibody C\\\subscript: H\\\3 domains for heavy chain heterodimerization" Protein Eng 9(7):617-621 ( 1996).

Ripka, J., et al., "Lectin-Resistant CHO Cells: Selection of Four New Pea Lectin-Resistant Phenotypes" Somat Cell Molec Gen 12(1):51-62 (Jan. 1, 1986).

Ripka, J., et al., "Two chinese hamster ovary glycosylation mutants affected in the conversion of GDP-mannose to GDP-fucose" Arch Biochem Biophys 249(2):533-545 (Sep. 1, 1986).

Rodewald, R.,, "pH-dependent binding of immunoglobulins to intestinal cells of the neonatal rat" J Cell Biol 71(2):666-669 (Nov. 1, 1976).

Rogers, M., et al., "The mouse cornea micropocket angiogenesis assay" Nat Protoc 2(10):2545-2550 (Oct. 11, 2007).

Roopenian, D., et al., "The MHC class I-like IgG receptor controls perinatal IgG transport, IgG homeostasis, and fate of IgG-Fc-coupled drugs" J Immunol 170(7):3528-3533 (Apr. 1, 2003).

Roopenian, D.,, "FcRn: the neonatal Fc receptor comes of age" Nat Rev Immunol 7(9):715-725 (Aug. 17, 2007).

Rosok, M., et al., "A combinatorial library strategy for the rapid humanization of anticarcinoma BR96 Fab" J Biol Chem 271(37):22611-22618 (Sep. 13, 1996).

Rossi., E., et al., "Multivalent Anti-CD20/Anti-CD22 Bispecific Antibody Fusion Proteins Made by the DNL Method Show Potent Lymphoma Cytotoxicity" Abstract (2495) ASH Annual Meeting, Baltimore, MD—USA, pp. 1 (Nov. 16-19, 2006).

Rothman, J., et al., "Antibody-Dependent Cytotoxicity Mediated by Natural Killer Cells is Enhanced by Castanospermine-Induced Alterations of IgG Glycosylation" Mol Immunol 26(12):1113-1123 (Dec. 1, 1989).

Routier, F., et al., "The glycosylation pattern of a humanized IgGI antibody (D1.3) expressed in CHO cells" Glycoconjugate J 14(2):201-207 (Feb. 1, 1997).

Rubinstein, E., et al., "Anti-Platelet Antibody Interactions with Fcγ Receptor" Semi Thromb Hemost 21(1):10-22 ( 1995).

Rudd, P., et al., "Glycosylation and the Immune System" Science 291(5512):2370-2376 (Mar. 23, 2001).

Rudikoff et al., "Single amino acid substitution altering antigen-binding specificity" Proc. Natl. Acad. Sci. USA, 79(6):1979-1983 (Mar. 1982).

Rudnick, S., et al., "Affinity and Avidity in Antibody-Based Tumor Targeting" Cancer Biother Radiopharm 24(2):155-162 (Apr. 1, 2009).

Sahni, J., et al., "Safety and Efficacy of Different Doses and Regimens of Faricimab vs Ranibizumab in Neovascular Age-Related Macular Degeneration: The AVENUE Phase 2 Randomized Clinical Trial" JAMA Ophthalmol 138(9):955-963 (Sep. 1, 2020).

Sahni, J., et al., "Simultaneous Inhibition of Angiopoietin-2 and Vascular Endothelial Growth Factor-A with Faricimab in Diabetic Macular Edema—BOULEVARD Phase 2 Randomized Trial" Ophthalmology 126(8):1155-1170 (Aug. 1, 2019).

Sampson, J., et al., "Unarmed, Tumor-Specific Monoclonal Antibody Effectively Treats Brain Tumors" PNAS USA 97(13):7503-7508 (Jun. 20, 2000).

Sarmay, G., et al., "Ligand Inhibition Studies on the Role of Fc Receptors in Antibody-Dependent Cell-Mediated Cytotoxicity." Mol Immunol 21(1):43-51 (Jan. 1, 1984).

Sarmay, G., et al., "Mapping and comparison of the interaction sites on the Fc region of IgG responsible for triggering antibody dependent cellular cytotoxicity (ADCC) through different types of human Fcγ receptor" Mol Immunol 29(5):633-639 (May 1, 1992).

Sato, Y.,, "Molecular diagnosis of tumor angiogenesis and anti-angiogenic cancer therapy" Int J Clin Oncol 8(4):200-206 (Aug. 1, 2003).

Sautes, C., Cell-Mediated Effects of Immunoglobulins "Chapter 2: Structure and Expression of Fc Receptors (FcR)" Fridman, W., & Sautes, C., eds., First edition, Austin, Texas—US:R.G. Landes Company,:29-66 ( 1997).

Schaefer, W., et al., "Immunoglobulin domain crossover as a generic approach for the production of bispecific IgG antibodies" PNAS USA 108(27):11187-11192 (Jul. 5, 2011).

Schlaeger, E., et al., "The protein hydrolysate, Primatone RL, is a cost-effective multiple growth promoter of mammalian cell culture in serum-containing and serum-free media and displays anti-apoptosis properties" J Immunol Methods 194(2):191-199 (Aug. 14, 1996).

Schlaeger, E., et al., "Transient gene expression in mammalian cells grown in serum-free suspension culture" Cytotechnology 30(1-3):71-83 (Jul. 1, 1999).

Schlaeth, M., et al., "Fc-engineered EGF-R antibodies mediate improved antibody-dependent cellular cytotoxicity (ADCC) against KRAS-mutated tumor cells" Cancer Sci 101(5):1080-1088 (Jan. 20, 2010).

Schlothauer, T., et al., "Novel human IgG1 and IgG4 Fc-engineered antibodies with completely abolished immune effector functions" Protein Eng Des Sel (w/Supplementary Figures), 29(10):457-466 (Oct. 1, 2016).

Schmidt, M. et al., "Suppression of Metastasis Formation by a Recombinant Single Chain Antibody-Toxin Targeted to Full-length and Oncogenic Variant EGF Receptors" Oncogene 18(9):1711-1721 (Mar. 15, 1999).

Schmidt-Erfurth, U., et al., "Intravitreal aflibercept injection for neovascular age-related macular degeneration: ninety-six-week results of the VIEW studies" Ophthalmology 121(1):193-201 (Jan. 1, 2014).

Schoojans, R. et al., "Fab Chains as an Efficient Heterodimerization Scaffold for the Production of Recombinant Bispecific and Trispecific Antibody Derivatives" J Immunol 165(12):7050-7057 (Dec. 15, 2000).

Scott, I.U., et al., "Month 24 Outcomes After Treatment Initiation With Anti-Vascular Endothelial Growth Factor Therapy for Macular Edema Due to Central Retinal or Hemiretinal Vein Occlusion:

(56) References Cited

OTHER PUBLICATIONS

SCORE2 Report 10: A Secondary Analysis of the SCORE2 Randomized Clinical Trial" JAMA Ophthalmol 137(12):1389-1398 (Dec. 1, 2019).

Scott, I.U., et al., "Patient-Reported Visual Function Outcomes After Anti-Vascular Endothelial Growth Factor Therapy for Macular Edema Due to Central Retinal or Hemiretinal Vein Occlusion: Preplanned Secondary Analysis of a Randomized Clinical Trial" JAMA Ophthalmol 137(8):932-938 (Aug. 1, 2019).

Schrama, D., et al., "Antibody Targeted Drugs as Cancer Therapeutics" Nat Rev Drug Discov 5:147-159 (Jan. 20, 2006).

Segal, D.,, "Introduction: Bispecific Antibodies" J Immunol Methods 248(1-2):1-6 (Feb. 1, 2001).

Sensel, M., et al., "Amino acid differences in the N-terminus of C(H)2 influence the relative abilities of IgG2 and IgG3 to activate complement" Mol Immunol 34(14):1019-1029 (Oct. 1, 1997).

Shen, J., et al., "Single Variable Domain Antibody as a Versatile Building Block for the Construction of IgG-like Bispecific Antibodies" J Immunol Methods 318(1-2):65-74 (Oct. 26, 2006).

Shields, R., et al., "High resolution mapping of the binding site on human IgG1 for Fc gamma RI, Fc gamma RII, Fc gamma RIII, and FcRn and design of IgG1 variants with improved binding to the Fc gamma R" J Biol Chem 276(9):6591-6604 (Mar. 2, 2001).

Shields, R.L., et al., "Lack of Fucose on Human IgG1 N-Linked Oligosaccharide Improves Binding to Human FcγRIII and Antibody-dependent Cellular Toxicity" J Biol Chem 277(30):26733-26740 (Jul. 26, 2002).

Shim, H.,, "One Target, different effects: a comparison of distinct therapeutic antibodies against the same targets" Exp Mol Med 43(10):539-549 (Oct. 31, 2011).

Shindo, Y., et al., "Combination Immunotherapy with 4-1BB Activation and PD-1 Blockade Enhances Antitumor Efficacy in a Mouse Model of Subcutaneous Tumor" Anticancer Res 35(1):129-136 (Jan. 1, 2015).

Shinkawa, T., et al., "The Absence of Fucose but Not the Presence of Galactose or Bisecting N-Acetyclucosamine of Human IgG1 Complex-type Oligosaccharides Shows the Critical Role of Enhancing Antibody-dependent Cellular Cytotoxicity" J Biol Chem 278(5):3466-3473 (Jan. 31, 2003).

Shitara, K., et al., "A New Vector for the High Level Expression of Chimeric Antibodies in Myeloma Cells" J Immunol Methods 167(1-2):271-278 (Jan. 3, 1994).

Shores, E., et al., "T cell development in mice lacking all T cell receptor ζ family members (ζ, η, and FcεRIγ)" J Exp Med 187(7):1093-1101 (Apr. 6, 1998).

Sidhu, S., et al., "Phage-displayed antibody libraries of synthetic heavy chain complementarity determining regions" J Mol Biol 338(2):299-310 (Apr. 23, 2004).

Simon, T., et al., "Antibody Domain Mutants Demonstrate Autonomy of the Antigen Binding Site" EMBO Journal 9(4):1051-1056 (Apr. 1, 1990).

Simon, T., et al., "Consolidation Treatment With Chimeric Anti-GD2-Antibody ch14.18 in Children Older Than 1 Year With Metastatic Neuroblastoma" J Clin Oncol 22(17):3549-3557 (Sep. 1, 2004).

Sims, M., et al., "A Humanized CD18 Antibody Can Block Function Without Cell Destruction" J Immunol 151(4):2296-2308 (Aug. 15, 1993).

Sinapis, C., et al., "Pharmacokinetics of intravitreal bevacizumab (Avastin®) in rabbits" Clin Ophthamol 5:697-704 (May 24, 2011).

Sinapis, C., et al., "Pharmacokinetics of Intravitreal Bevacizumab (Avastin) in Rabbits" IOVS—Invest Opthalmol Vis Sci (Abstract), 51(13):2440 (Apr. 1, 2010).

Sondermann, P., et al., "Crystal structure of the soluble form of the human Fcγ-receptor IIb: a new member of the immunoglobulin superfamily at 1.7 A resolution" EMBO J 18(5):1095-1103 (Mar. 1, 1999).

Sondermann, P., et al., "The 3.2-A crystal structure of the human IgG1 Fc fragment-Fc gammaRIII complex" Nature 406(6793):267-273 (Jul. 20, 2000).

Song, C., Cancer Drug Resistance "Chapter 2: Influence of Tumor pH on Therapeutic Response" Teicher, B., ed., First edition, Humana Totowa, N.J.—USA:Humana Press,:21-42 (Mar. 9, 2006).

Stankova, J., et al., "Fucose-Activated Killer (FAK) Cells: Anomalous Killers with Augmented Cytotoxic Activity" J Immunol 135(6):3719-3728 (Dec. 1, 1985).

Steeg, P., et al., "Brain Metastases as Preventive and Theraputic Targets" Nat Rev Cancer 11(5):352-363 (Apr. 7, 2011).

Steplewski, Z., et al., "Biological activity of human-mouse IgG1, IgG2, IgG3, and IgG4 chimeric monoclonal antibodies with anti-tumor specificity" PNAS USA 85(13):4852-4856 (Jul. 1, 1988).

Streit, M., et al., "Angiogenesis, lymphangiogenesis, and melanoma metastasis" Oncogene 22(20):3172-3179 (May 19, 2003).

Strohmeier, G., et al., "Neutrophil functional responses depend on immune complex valency" J Leukocyte Biol 58(4):403-414 (Oct. 1, 1995).

Strohmeier, G., et al., "Role of the FcγR subclasses FcγRII and FcγRIII in the activation of human neutrophils by low and high valency immune complexes" J Leukocyte Biol 58(4):415-422 (Oct. 1, 1995).

Stubenrauch, K., et al., "Impact of molecular processing in the hinge region of therapeutic IgG4 antibodies on disposition profiles in *Cynomolgus* monkeys" Drug Metab Dispos 38(1):84-91 (Jan. 1, 2010).

Suzuki, Y., et al., "Distinct contribution of Fc receptors and angiotensin II-dependent pathways in anti-GBM glomerulonephritis" Kidney Int 54(4):1166-1174 (Oct. 1, 1998).

Sylvestre, D et al., "Fc receptors initiate the Arthus reaction: redefining the inflammatory cascade" Science 265(5175):1095-1098 (Aug. 19, 1994).

Sylvestre, D, "A dominant role for mast cell Fc receptors in the Arthus reaction" Immunity 5(4):387-390 (Oct. 1, 1996).

Sylvestre, D., et al., "Immunoglobulin G-mediated inflammatory responses develop normally in complement-deficient mice" J Exp Med 184(6):2385-2392 (Dec. 1, 1996).

Takahashi, N., et al., "Comparative Structural Study of the N-Linked Oligosaccharides of Human Normal and Pathological Immunoglobulin G" ACS Biochemistry 26(4):1137-1144 (Feb. 24, 1987).

Takai, T., et al., "Augmented humoral and anaphylactic responses in FcγRII-deficient mice" Nature 379(6563):346-349 (Jan. 25, 1996).

Takai, T., et al., "FcR γ chain deletion results in pleiotrophic effector cell defects" Cell 76(3):519-529 (Feb. 11, 1994).

Talmadge, J., et al., "Murine Models to Evaluate Novel and Conventional Therapeutic Strategies for Cancer" Am J Pathol 170(3):793-804 (Mar. 1, 2007).

Tam, S., et al., "Functional, Biophysical, and Structural Characterization of Human IgG1 and IgG4 Fc Variants with Ablated Immune Functionality" Antibodies 6(3):1-34 (Sep. 1, 2017).

Tamm, A., et al., "The IgG binding site of human FcγRIIIB receptor involves CC' and FG loops of the membrane-proximal domain" J Biol Chem 271(7):3659-3666 (Feb. 16, 1996).

Tamura, K.,, "Human Immunoadhesin A New Ligand Antagonist (English Translation)" Pharma Soc Japan 33(1):46-50 (Jan. 1, 1997).

Tao, H., et al., "Structural Features of Human Immunoglobulin G That Determine Isotype-Specific Differences in Complement Activation." J Exp Med 178(2):661-667 (Aug. 1, 1993).

Tao, M., et al., "Studies of Aglycosylated Chimeric Mouse-Human IgG: Role of Carbohydrate in the Structure and Effector Functions Mediated by the Human IgG Constant Region." J Immunol 143(8):2595-2601 (Oct. 15, 1989).

Tao, M., et al., "The differential ability of human IgG1 and IgG4 to activate complement is determined by the COOH-terminal sequence of the CH2 domain" J Exp Med 173(4):1025-1028 (Apr. 1, 1991).

Tax, W., et al., "Fc receptors for mouse IgG1 on human monocytes: polymorphism and role in antibody-induced T cell proliferation" J Immunol 133(3):1185-1189 (Sep. 1, 1984).

Taylor, L. et al., "In vitro and in vivo activities of OX40 (CD134)-IgG fusion protein isoforms with different levels of immune-effector functions" J Leukoc Biol 72(3):522-529 (Sep. 1, 2002).

(56) References Cited

OTHER PUBLICATIONS

Taylor, S., et al., "Thrombosis and shock induced by activating antiplatelet antibodies in human FcγRIIA transgenic mice: the interplay among antibody, spleen, and Fc receptor" Blood 96(13):4254-4260 (Dec. 15, 2000).

Teillaud, J.,, "Antibody-dependent Cellular Cytotoxicity (ADCC)" ELS—Encyclopedia of Life Sciences—Wiley:1-8 (Jul. 16, 2012).

Tejada, T., et al., "Tumor-driven paracrine platelet-derived growth factor receptor alpha signaling is a key determinant of stromal cell recruitment in a model of human lung carcinoma" Clin Cancer Res 12(9):2676-2688 (May 1, 2006).

Tesar, D., et al., "Ligand valency affects transcytosis, recycling and intracellular trafficking mediated by the neonatal Fc receptor" Traffic-Copehagen 7(9):1127-1142 (Jun. 29, 2006).

Thomas, M. et al., "A novel angiopoietin-2 selective fully human antibody with potent anti-tumoral and anti-angiogenic efficacy and superior side effect profile compared to pan-angiopoietin-1-2 inhibitors" PLOS One 8(2):e54923 (1-11) (Feb. 6, 2013).

Thomas, M., et al., "LC06, a novel angiopoietin-2 selective human antibody with potent anti-tumoral and anti-angiogenic efficacy in different xenograft models" Eur J Cancer 8(7 Suppl 1):156-157 (Nov. 1, 2010).

Thommesen, J., et al., "Lysine 322 in the human IgG3 C(H)2 domain is crucial for antibody dependent complement activation" Mol Immunol 37(16):995-1004 (Nov. 1, 2000).

Thurber, G., et al., "Antibody tumor penetration: transport opposed by systemic and antigen-mediated clearance" Adv Drug Deliv Rev 60(12):1421-1434 (Sep. 1, 2008).

Ting, A., et al., "Fcγ receptor activation induces the tyrosine phosphorylation of both phospholipase C (PLC)-γl and PLC-γ2 in natural killer cells" J Exp Med 176(6):1751-1755 (Dec. 1, 1992).

Tomiyama, Y., et al., "Response of human platelets to activating monoclonal antibodies: Importance of FcγRII (CD32) phenotype and level of expression" Blood 80(9):2261-2268 (Nov. 1, 1992).

Tonini, T. et al., "Molecular basis of angiogenesis and cancer" Oncogene 22(42):6549-6556 (Sep. 29, 2003).

Torgov, M., et al., "Generation of an intensely potent anthracycline by a monoclonal antibody—β-galactosidase conjugate" Bioconjugate Chem 16(3):717-21 (May 1, 2005).

Traunecker, A., et al., "Bispecific single chain molecules (Janusins) target cytotoxic lymphocytes on HIV infected cells" EMBO J 10(12):3655-3659 (Dec. 10, 1991).

Tsuchiya, N., et al., "Effects of Galactose Depletion from Oligosaccharide Chains on Immunological Activities of Human IgG" J Rheumatol 16(3):285-290 (Mar. 1, 1989).

Tutt, A., et al., "Monoclonal antibody therapy of B cell lymphoma: signaling activity on tumor cells appears more important than recruitment of effectors" J Immunol 161(6):3176-3185 (Sep. 15, 1998).

Tutt, A., et al., "Trispecific F(ab')3 derivatives that use cooperative signaling via the TCR/CD3 complex and CD2 to activate and redirect resting cytotoxic T cells" J Immunol 147(1):60-69 (Jul. 1, 1991).

Umaña, P., et al., "Engineered Glycoforms of an Antineuroblastoma IgG1 with Optimized Antibody-Dependent Cellular Cytotoxic Activity" Nat Biotechnol 17(2):176-180 (Feb. 1, 1999).

Urfer, R., et al., "High resolution mapping of the binding site of TrkA for nerve growth factor and TrkC for neurotrophin-3 on the second immunoglobulin-like domain of the Trk receptors" J Biol Chem 273(10):5829-5840 (Mar. 6, 1998).

Urlaub, G., et al., "Isolation of chinese hamster cell mutants deficient in dihydrofolate reductase activity" PNAS US 77(7):4216-4220 (Jul. 1, 1980).

Clinical TRIALS.gov, "A Study of (RO6867461) in Participants With Center-Involving Diabetic Macular Edema (BOULEVARD)" (ClinicalTrials.gov ID: NCT02699450; History of Changes, Version 9; First Posted: Mar. 4, 2016; Last Updated Posted: Dec. 26, 2017; Retrieved: Aug. 28, 2023),:1-8 (Dec. 21, 2007).

Vajdos, F., et al., "Comprehensive functional maps of the antigen-binding site of an anti-ErbB2 antibody obtained with shotgun scanning mutagenesis" J Mol Biol 320(2):415-428 (Jul. 5, 2002).

Vallette, F., et al., "Construction of mutant and chimeric genes using the polymerase chain reaction" Nucl Acids Res 17(2):723-733 (Jan. 25, 1989).

Van De Winkel, J.G., et al., "Biology of human immunoglobulin G Fc receptors" J Leukocyte Biol 49(5):511-524 (May 1, 1991).

Vance, B., et al., "Binding of monomeric human IgG defines an expression polymorphism of FcγRIII on large granular lymphocyte/natural killer cells" J Immunol 151(11):6429-6439 (Dec. 1, 1993).

Varano, M., et al., "Current barriers to treatment for wet age-related macular degeneration (wAMD): findings from the wAMD patient and caregiver survey" Clin Ophthalmol 9:2243-2250 (Dec. 1, 2015).

Vaswani, S.,, "Humanized Antibodies as Potential Therapeutic Drugs" Ann Allergy Asthma Immunol 81(2):105-119 (Aug. 1, 1998).

Vaz-Pereira, S., et al., "Real-World Outcomes of Anti-VEGF Treatment for Retinal Vein Occlusion in Portugal" Eur J Ophthalmol 27(6):756-761 (Nov. 8, 2017).

Vijayalkakshmi, M., "Antibody Purification Methods" Appl Biochem Biotech 75(1):93-102 (Oct. 1, 1998).

Vitetta, E., et al., "Considering Therapeutic Antibodies" Science 313(5785):308-309 (Jul. 21, 2006).

Vitetta, E., et al., "Redesigning nature's poisons to create anti-tumor reagents" Science 238(4830):1098-1104 (Nov. 20, 1987).

Vollmers, H., et al., "The 'early birds': Natural IgM antibodies and immune surveillance" Histol Histopathol 20(3):927-937 (Jul. 1, 2005).

Vollmers, H.,, "Death by stress: natural IgM-induced apoptosis" Methods Find Exp Clin Pharmacol 27(3):185-191 (Apr. 1, 2005).

Voskoglou-Nomikos, T. et al., "Clinical Predictive Value of the in Vitro Cell Line, Human Xenograft, and Mouse Allograft Preclinical Cancer Models" Clin Can Res 9(11):4227-4239 (Sep. 15, 2003).

Vukicevic, M., et al., "Caregiver perceptions about the impact of caring for patients with wet age-related macular degeneration" Eye (London) 30(3):413-421 (Mar. 1, 2016).

Walker, M., et al., "Aglycosylation of Human IgG1 and IgG3 Monoclonal Antibodies Can Eliminate Recognition by Human Cells Expressing FcγRI and/or FcγRII Receptors." Biochem J 259(2):347-353 (Apr. 15, 1989).

Wang, L.,, "Expanding the genetic code" Chem Commun—Cambridge 1:1-10 (Jan. 7, 2002).

Ward, S., et al., "The Effector Functions of Immunoglobulins: Implications for Therapy." Ther Immunology 2(2):77-94 (Apr. 1, 1995).

Warmderdam, P., et al., "A Single Amino Acid in the Second Ig-Like Domain of the Human Fcγ Receptor II is Critical for Human IgG2 Binding" J Immunol 147(4):1338-1343 (Aug. 15, 1991).

Warren, R., et al., "Regulation by Vascular Endothelial Growth Factor of Human Colon Cancer Tumorigenesis in a Mouse Model of Experimental Liver Metastasis" J Clin Invest 95(4):1789-1797 (Apr. 1, 1995).

Wartha, K. et al., "A novel bispecific Fap-Dr5 antibody inducing potent and tumor-specific death receptor 5 (Dr5) activation by fibroblast activation protein (Fap)-dependent crosslinking" Cancer Res 74( Suppl 19):1 (Oct. 1, 2014).

Waterhouse, P., et al., "Combinatorial infection and in vivo recombination: a strategy for making large phage antibody repertoires" Nucleic Acids Res 21(9):2265-2266 (May 11, 1993).

Watt, G., et al., "Site-specific glycosylation of an aglycosylated human IgG1-Fc antibody protein generated neoglycoproteins with enhanced function" Chem Biol 10(9):807-814 (Sep. 1, 2003).

Wawrzynczak, E., et al., "Blood Clearance in the Mouse of an Aglycosyl Recombinant Monoclonal Antibody" Biochem Soc Trans 17(6):1061-1062 (Dec. 1, 1989).

Wawrzynczak, E., et al., "Blood clearance in the rat of a recombinant mouse monoclonal antibody lacking the N-linked oligosaccharide side chains of the CH2 domains" Mol Immunol 29(2):213-220 (Feb. 1, 1992).

Wawrzynczak, E., et al., "Recombinant Mouse Monoclonal Antibodies with single Amino Acid Substitutions Affecting Clq and

(56) References Cited

OTHER PUBLICATIONS

High Affinity Fc Receptor Binding Have Identical Serum Half-lives in the BALB/c Mouse" Mol Immunol 29(2):221-227 (Feb. 1, 1992).

Wecker, T., et al., "Five-year visual acuity outcomes and injection patterns in patients with pro-re-nata treatments for AMD, DME, RVO and myopic CNV" Br J Ophthal 101(3):353-359 (Mar. 1, 2017).

Weidner, K., et al., "Anti-Angiogenic Activity of a Tetravalent Bispecific Antibody (TAvi6) Targeting VEGF and Angiopoietin-2." Blood 116(21):4304 (Nov. 19, 2010).

Weis, W., et al., "The C-Type Lectin Superfamily in the Immune System" Immunol Rev 163(1):19-34 (Apr. 26, 1998).

Wells, J., et al., "Cassette mutagenesis: An efficient method for generation of multiple mutations at defined sites" Gene 34(2-3):315-323 (Jan. 1, 1985).

Werner, R., et al., "Appropriate mammalian expression systems for biopharmaceuticals" Arznei-Forschung/Drug Res 48(8):870-880 (Aug. 1, 1998).

Werther, W., et al., "Humanization of an Anti-Lymphocyte Function-Associated Antigen (LFA)-1 Monoclonal Antibody and Reengineering of the Humanized Antibody for Binding to Rhesus LFA-1" J Immunol 157(11):4986-4995 (Dec. 1, 1996).

White, C., et al., "Antibody-targeted immunotherapy for treatment of malignancy" Ann Rev Med 52:125-145 (Feb. 1, 2001).

Williams, R., et al., "Heteroclitic polyclonal and monoclonal anti-Gm(a) and anti-Gm(g) human rheumatoid factors react with epitopes induced in Gm(a-), Gm(g-) IgG by interaction with antigen or by nonspecific aggregation" J Immunol 149(5):1817-1824 (Sep. 1, 1992).

Wines, B., et al., "The IgG Fc contains distinct Fc receptor (FcR) binding sites: the leukocyte receptors FcγRI and FcγRIIa bind to a region in the Fc distinct from that recognized by neonatal FcR and protein A" J Immunol 164(10):5313-5318 (May 15, 2000).

Winter, G., et al., "Making antibodies by phage display technology" Annu Rev Immunol 12(1):433-455 (Apr. 1, 1994).

Woof, J., et al., "Localisation of the Monocyte-Binding Region on Human Immunoglobulin G." Mol Immunol 23(3):319-330 (Mar. 1, 1986).

Wright, A., et al., "Effect of altered CH2-associated carbohydrate structure on the functional properties and in vivo fate of chimeric mouse-human immunoglobulin G1" J Exp Med 180(3):1087-1096 (Sep. 1, 1994).

Wright, A., et al., "Effect of glycosylation on antibody function: Implications for genetic engineering" Trends Biotechnol 15(1):26-32 (Jan. 1, 1997).

Wright, A.,, "Effect of C2-associated carbohydrate structure on Ig effector function: Studies with chimeric mouse-human IgG1 antibodies in glycosylation mutants of Chinese Hamster Ovary cells" J Immunol 160(7):3393-3402 (Apr. 1, 1998).

Wu, C., et al., "Simultaneous Targeting of Multiple Disease Mediators by a Dual-Variable-Domain Immunoglobulin" Nat Biotechnol 25(11):1290-1297 (Oct. 14, 2007).

Wu, J., et al., "A Novel Polymorphism of FcγRIIIa (CD16) Alters Receptor Function and Predisposes to Autoimmune Disease." J Clin Invest 100(5):1059-1070 (Sep. 1, 1997).

Xie, M., et al., "Direct demonstration of MuSK involvement in acetylcholine receptor clustering through identification of agonist scFv." Nat Biotechnol 15(8):768-771 (Aug. 1, 1997).

Xie, Z., et al., "A new format of Bispecific Antibody: Highly Efficient Heterodimerization, Expression and Tumor Cell Lysis" J Immunol Methods 296(1-2):95-101 (Nov. 19, 2004).

Xu, D., et al., "In vitro characterization of five humanized OKT3 effector function variant antibodies" Cell Immunol 200(1):16-26 (Feb. 25, 2000).

Xu, Y., et al., "Residue at position 331 in the IgG1 and IgG4 CH2 domains contributes to their differential ability to bind and activate complement" J Biol Chem 269(5):3469-3474 (Feb. 4, 1994).

Xu, Y., et al., "The N-Terminal Sequence of the CH2 Domain Controls the Differential Ability of Human IgG1 and IgG2 to Activate Complement." J Immunol (Abstract: 862), 150(8):152A (Apr. 15, 1993).

Yadav, S. et al., "Establishing a Link Between Amino Acid Sequences and Self-Associating and Viscoelastic Behavior of Two Closely Related Monoclonal Antibodies" Pharma Res 28(7):1750-1764 (Apr. 6, 2011).

Yadav, S., et al., "The Influence of Charge Distribution on Self-Association and Viscosity Behavior of Monoclonal Antibody Solutions" ACS Mol Pharmaceutics 9(4):791-802 (Feb. 21, 2012).

Yap, N., et al., "Human Fc Gamma Receptor IIA (FcγRIIA) Genotyping and Association with Systemic Lupus Erythematosus (SLE) in Chinese and Malays in Malaysia." Lupus 8(4):305-310 (May 1, 1999).

Yasuda, S., et al., "Simultaneous Blockade of Programmed Death 1 and Vascular Endothelial Growth Factor Receptor 2 (VEGFR2) Induces Synergistic Anti-Tumour Effect In Vivo" Clin Exp Immunol 172(3):500-506 (Jun. 1, 2013).

Yazaki, P. et al., "Expression of recombinant antibodies in mammalian cell lines" Methods Molec Biol 248:255-268 ( 2004).

Yeung, Y., et al., "A Therapeutic Anti-VEGF Antibody with Increased Potency Independent of Pharmacokinetic Half-life" Cancer Res 70(8):3269-3277 (Mar. 30, 2010).

Yeung, Y., et al., "Engineering Human IgG1 Affinity to Human Neonatal Fc Receptor: Impact of Affinity Improvement on Pharmacokinetics in Primates" J Immunol 182(12):7663-7671 (Jun. 15, 2009).

Yu, L. et al., "Interaction between Bevacizumab and Murine VEGF-A: a Reassessment" IVOS—Invest Ophthalmol Vis Sci 49(2):522-527 (Feb. 1, 2008).

Yuan, R., et al., "Antibody-mediated modulation of *Cryptococcus neoformans* infection is dependent on distinct Fc receptor functions and IgG subclasses" J Exp Med 187(4):641-648 (Feb. 16, 1998).

Zhang et al., "English translation of the Abstract" Chemistry of Life 27(2):166-169 ( 2007).

Zhang, K., et al., "Ophthalmic drug discovery: novel targets and mechanisms for retinal diseases and glaucoma" Nat Rev Drug Discov 11(7):541-559 (Jul. 15, 2012).

Zheng, X., et al., "Administration of noncytolytic IL-10/Fc in murine models of lipopolysaccharide-induced septic shock and allogeneic islet transplantation" J Immunol 154(10):5590-5600 (May 15, 1995).

Zola, H. et al. Monoclonal Antibodies: A Manual of Techniques "Chapter 6: Using Monoclonal Antibodies: soluble Antigens" First edition, Boca Raton, Florida—USA:CRC Press,:147-158 (Jul. 30, 1987).

Hulett, M., et al., "Chimeric Fc Receptors Identify Functional Domains of the Murine High Affinity Receptors for IgG" J Immunol 147(6):1863-1868 (Sep. 15, 1991).

International Preliminary Report on Patentability for PCT/EP2020/072088, issued by the International Search Authority on Feb. 8, 2022; pp. 1-11 (Feb. 17, 2022).

Jendreyko, N. et al., "Intradiabodies, Bispecific, Tetravalent Antibodies for the Simultaneous Functional Knockout of Two Cell Surface Receptors" J Biol Chem 278(48):47812-47819 (Nov. 28, 2003).

Makrides, S., "Therapeutic Inhibition of the Complement System" Pharmacol Rev 50(1):59-87 (Mar. 1, 1998).

Papac, D., et al., "A high-throughput microscale method to release N-linked oligosaccharide from glycoproteins for matrix-assisted laser desorption/ionization time-of-flight mass spectrometric analysis" Glycobiology 8(5):445-454 (May 1, 1998).

Weng, Z., et al., "Computational determination of the structure of rat Fc bound to the neonatal Fc receptor" J Mol Biol 282(2):217-225 (Sep. 18, 1998).

BCAV Change from Baseline Over Time to Week 24 (Study Eye)
*Primary endpoint in Treatment-naive Patients*

Disclaimer: Conceptual grid based on cross study comparisons and real world data, meant for facilitating discussion

*12 or 16 weekly dosing intervals of VA2 vs 4 weekly ranibizumab*

IVT = intravitreal; Q4W = every 4 Weeks; Q12W = every 12 weeks; Q16W = every 16 weeks; W = week a All patients will be assessed for disease activity at Week 24. Patients in Arm B who are assessed with active disease at Week 24 will switch to RO6867461 Q12W dosing regimen for the remainder of the study.

BCVA = best corrected visual acuity; MMRM = mixed model for repeated measurement. Visits are time windowed. Model includes categorical covariates of treatment group, visit, visit by treatment group interaction and the continuous covariate of baseline BCVA. Unstructured covariance was used.

1

TREATMENT OF AGE-RELATED MACULAR DEGENERATION AND DIABETIC MACULAR EDEMA BY ADMINISTRATION OF A BISPECIFIC ANTIBODY TO VEGF AND ANG-2

CROSS REFERENCE TO RELATED APPLICATIONS

This application is a continuation of U.S. application Ser. No. 16/985,477, filed Aug. 5, 2020, which is a continuation of International Application No. PCT/EP2019/052704, filed Feb. 5, 2019, claiming priority to provisional Application No. 62/627,103 filed Feb. 6, 2018 and provisional Application No. 62/729,333, filed Sep. 10, 2018, which are incorporated herein by reference in their entireties.

SEQUENCE LISTING

This application contains a Sequence Listing which has been submitted electronically in XML format and is hereby incorporated by reference in its entirety. Said XML copy, created on May 16, 2023, is named P34648-US-3_Corrected_SeqListing.xml and is 37,522 bytes in size.

The current invention relates to the use of antibodies which bind to VEGF and ANG2 for the treatment of ophthalmologic diseases.

BACKGROUND OF THE INVENTION

Angiogenesis is implicated in the pathogenesis of a variety of disorders which include solid tumors, intraocular neovascular syndromes such as proliferative retinopathies or age-related macular degeneration (AMD), rheumatoid arthritis, and psoriasis (Folkman, J., et al., J. Biol. Chem. 267 (1992) 10931-10934; Klagsbrun, M., et al., Annu. Rev. Physiol. 53 (1991) 217-239; and Gamer, A., Vascular diseases, in: Pathobiology of ocular disease, A dynamic approach, Garner, A., and Klintworth, G. K. (eds.), 2nd edition, Marcel Dekker, New York (1994), pp. 1625-1710).

Ranibizumab (trade name Lucentis®) is a monoclonal antibody fragment derived from the same parent murine antibody as bevacizumab (Avastin®). However, it has been affinity matured to provide stronger binding to VEGF-A (WO 98/45331). It is known that systemic blockade of VEGF-A is associated with an increased risk of certain adverse events, therefore ranibizumab is missing an Fc part in order to reduce systemic exposure and the risk of systemic toxicities. It is an anti-angiogenic agent that has been approved to treat the "wet" type of age-related macular degeneration (neovascular AMD), a common form of age-related vision loss.

Corneal angiogenesis assays have shown that both ANG-1 and ANG-2 had similar effects, acting synergistically with VEGF to promote growth of new blood vessels. Asahara, T., et al., Circ. Res. 83 (1998) 233-40. The possibility that there was a dose-dependent endothelial response was raised by the observation that in vitro at high concentration, ANG-2 can also be pro-angiogenic (Kim, I., et al., Oncogene 19 (2000) 4549-52). At high concentration, ANG-2 acts as an apoptosis survival factor for endothelial cells during serum deprivation apoptosis through activation of Tie2 via PI-3 Kinase and Akt pathway (Kim, I., et al., Oncogene 19 (2000) 4549-52).

Ocular vascular diseases such as "wet" age related macular degeneration (AMD) and proliferative diabetic retinopathy (PDR), are due to abnormal choroidal or retinal neovascularization respectively. Bleeding and leakage from these vessels can cause retinal dysfunction and loss of vision Other retinal vascular disease, such as diabetic macular edema (DME) and macular edema secondary to retinal vein occlusion (RVO) are due to abnormal retinal leakage leading to retinal swelling and impairing visual function. These conditions are leading causes of visual loss in industrialized nations. Since the retina consists of well-defined layers of neuronal, glial, and vascular elements, relatively small disturbances such as those seen in vascular proliferation or edema can lead to significant loss of visual function. Inherited retinal degenerations, such as Retinitis Pigmentosa (RP), are also associated with vascular abnormalities, such as arteriolar narrowing and vascular atrophy. They affect as many as 1 in 3500 individuals and are characterized by progressive night blindness, visual field loss, optic nerve atrophy, arteriolar attenuation, and central loss of vision often progressing to complete blindness.

Ischemic retinopathies are characterized by loss or dysfunction of the retinal vasculature which results in a reduction of blood flow and hypoxia. The retina responds to hypoxia by generating signals to grow new blood vessels, but these new vessels are usually fragile and disorganized. It is the growth of these abnormal new vessels that creates most of the threat to vision since they can leak, hemorrhage or lead to scarring that may end in retinal detachment. Current treatments for ischemic retinopathies seek to halt the growth of the pathological vessels but do not address the underlying ischemia that drives their growth. Furthermore, standard treatment for diabetic retinopathy, an ischemic retinopathy that affects millions, involves destruction of a portion of the retina with a laser in an attempt destroy ischemic tissue in order to stop new vessel growth and preserve central vision. Strategies have been employed to block the function of vascular endothelial growth factor (VEGF), a major promoter of abnormal vessel growth and leakage. In the short term, anti-VEGF therapy can improve vision, but it does not address the underlying ischemia and in fact may exacerbate this condition as it inhibits all vessel growth, including beneficial collaterals. There is also the serious concern of systemic exposure of these drugs in elderly and/or diabetic patients where new vessel growth may be required in ischemic brains, hearts or limbs.

SUMMARY OF THE INVENTION

According to one aspect of the present invention, methods, uses, bispecific antibodies (for use), medicaments or pharmaceutical formulations are provided for the treatment of patients suffering from an ocular vascular disease the method comprising administering to the patient an effective amount of a bispecific antibody which binds to human vascular endothelial growth factor (VEGF) and to human angiopoietin-2 (ANG-2), wherein the bispecific antibody is administered (is to be administered) intravitreally every 8 weeks or less frequently (in one embodiment every 9 weeks or less frequently; in one embodiment every 10 weeks or less frequently; in one embodiment every 11 weeks or less frequently; in one embodiment every 12 weeks or less frequently; in one embodiment every 13 weeks or less frequently; in one embodiment every 14 weeks or less frequently; in one embodiment every 15 weeks or less frequently in one embodiment every 16 weeks or less frequently).

One aspect of the invention is such method, use, bispecific antibody (for use), medicament or pharmaceutical formulation (for use) of/for treating a patient suffering from an ocular vascular disease the method, use, bispecific antibody (for use), medicament or pharmaceutical formulation (for use) comprising administering (intravitreally) to the patient an effective amount of a bispecific antibody which binds to human vascular endothelial growth factor (VEGF) and to human angiopoietin-2 (ANG-2), wherein the patient gains 12 or more letters (in one embodiment 13 or more letters, in one embodiment 14 or more letters, in one embodiment 15 or more letters) of Best Corrected Visual Acuity (BCVA) measured using Early Treatment Diabetic Retinopathy Study (ETDRS) like charts, compared to the patient's BCVA letter score prior to the dosing of the bispecific VEGF/ANG2 antibody. In one embodiment the bispecific antibody is administered intravitreally every 8 weeks or less frequently. One embodiment of the invention is a method of treating a patient suffering from an ocular vascular disease the method comprising administering (intravitreally) to the patient an effective amount of a bispecific antibody which binds to human vascular endothelial growth factor (VEGF) and to human angiopoietin-2 (ANG-2), wherein the patient experiences an improvement in vision subsequent to the administration of the bispecific VEGF/ANG2 antibody as measured by gaining 12 or more letters (in one embodiment 13 or more letters, in one embodiment 14 or more letters, in one embodiment 15 or more letters) of Best Corrected Visual Acuity (BCVA) measured using Early Treatment Diabetic Retinopathy Study (ETDRS) like charts, compared to the patient's BCVA letter score prior to the dosing of the bispecific VEGF/ANG2 antibody. In one embodiment the bispecific antibody is administered intravitreally every 8 weeks or less frequently.

In one embodiment of the invention the gain of letters in the BCVA/ETDRS letter score is measured at 4 weeks, and/or at 8 weeks, and/or at 12 weeks, and/or at 16 weeks, and/or at 20 weeks, and/or at 24 weeks after treatment start, respectively.

In one embodiment of the invention the gain of letters in the BCVA/ETDRS letter score is measured at 24 weeks, and/or at 25 weeks, and/or at 26 weeks, and/or at 27 weeks, and/or at 28 weeks, and/or at 29 weeks, and/or at 30 weeks, and/or at 31 weeks, and/or at 32 weeks, and/or at 33 weeks, and/or at 34 weeks, and/or at 35 weeks, and/or at 36 weeks, and/or at 37 weeks, and/or at 38 weeks, and/or at 39 weeks, and/or at 40 weeks, and/or at 41 weeks, and/or at 42 weeks, and/or at 43 weeks, and/or at 44 weeks, and/or at 45 weeks, and/or at 46 weeks, and/or at 47 weeks, and/or at 48 weeks, and/or at 49 weeks, and/or at 50 weeks, and/or at 51 weeks, and/or at 52 weeks, and/or at 53 weeks, and/or at 54 weeks, and/or at 55 weeks, and/or at 56 weeks, and/or at 57 weeks, and/or at 58 weeks, and/or at 59 weeks, and/or at 60 weeks after treatment start, respectively. In one embodiment of the invention the ocular vascular disease is selected from the group of: wet age-related macular degeneration (wet AMD), neovascular AMD, diabetic macular edema (DME), cystoid macular edema (CME), non-proliferative diabetic retinopathy (NPDR), proliferative diabetic retinopathy (PDR), macular edema secondary to central retinal vein occlusion, secondary to hemiretinal vein occlusion or secondary to branch vein occlusion, retinitis, conjunctivitis, uveitis, chor-oiditis, choroidal neovascularization (CNV) secondary to ocular inflammation including secondary to ocular histo-plasmosis or presumed histoplasmosis or choroiditis; myo-pic choroidal neovascularization (mCNV). And choroidal neovascularization secondary to trauma, retinopathy of pre-maturity and rubeosis iridis/rubeotic glaucoma.

In one embodiment of the invention the ocular vascular disease is diabetic macular edema (DME).

In one embodiment of the invention the ocular vascular disease is diabetic macular edema (DME) and the gain of letters in the BCVA/ETDRS letter score is measured at about 9 to 15 month (in one embodiment at 9 to 14 month, in one embodiment at 9 to 12 month) after treatment start.

In one embodiment of the invention the ocular vascular disease is diabetic macular edema (DME) and the gain of letters in the BCVA/ETDRS letter score is measured at 36 weeks, and/or at 37 weeks, and/or at 38 weeks, and/or at 39 weeks, and/or at 40 weeks, and/or at 41 weeks, and/or at 42 weeks, and/or at 43 weeks, and/or at 44 weeks, and/or at 45 weeks, and/or at 46 weeks, and/or at 47 weeks, and/or at 48 weeks, and/or at 49 weeks, and/or at 50 weeks, and/or at 51 weeks, and/or at 52 weeks, and/or at 53 weeks, and/or at 54 weeks, and/or at 55 weeks, and/or at 56 weeks, and/or at 57 weeks, and/or at 58 weeks, and/or at 59 weeks, and/or at 60 weeks after treatment start, respectively.

These time points are quite early, typically maximum gains are not reached until about month 6-9 in nAMD and m 9-12 in DME In one embodiment of the invention the ocular vascular disease is wet age-related macular degeneration (wet AMD) (or neovascular age-related macular degeneration (nAMD).

In one embodiment of the invention the ocular vascular disease is wet age-related macular degeneration (wet AMD) (or neovascular age-related macular degeneration (nAMD) and the gain of letters in the BCVA/ETDRS letter score is measured at about 9 to 15 month (in one embodiment at 6 to 9 month, in one embodiment at 6 to 12 month) after treatment start.

In one embodiment of the invention the ocular vascular disease is wet age-related macular degeneration (wet AMD) (or neovascular age-related macular degeneration (nAMD) and the gain of letters in the BCVA/ETDRS letter score is measured at 24 weeks, and/or at 25 weeks, and/or at 26 weeks, and/or at 27 weeks, and/or at 28 weeks, and/or at 29 weeks, and/or at 30 weeks, and/or at 31 weeks, and/or at 32 weeks, and/or at 33 weeks, and/or at 34 weeks, and/or at 35 weeks, and/or at 36 weeks, and/or at 37 weeks, and/or at 38 weeks, and/or at 39 weeks, and/or at 40 weeks, and/or at 41 weeks, and/or at 42 weeks, and/or at 43 weeks, and/or at 44 weeks, and/or at 45 weeks, and/or at 46 weeks, and/or at 47 weeks, and/or at 48 weeks, and/or at 49 weeks, and/or at 50 weeks, and/or at 51 weeks, and/or at 52 weeks, and/or at 53 weeks, after treatment start, respectively.

In one embodiment of the invention the bispecific antibody which binds to human VEGF and to human ANG2 is a bispecific, bivalent anti-VEGF/ANG2 antibody comprising a first antigen-binding site that specifically binds to human VEGF and a second antigen-binding site that specifically binds to human ANG-2, wherein i) said first antigen-binding site specifically binding to VEGF comprises in the heavy chain variable domain a CDR3H region of SEQ ID NO: 1, a CDR2H region of SEQ ID NO: 2, and a CDR1H region of SEQ ID NO:3, and in the light chain variable domain a CDR3L region of SEQ ID NO: 4, a CDR2L region of SEQ ID NO:5, and a CDR1L region of SEQ ID NO: 6; and ii) said second antigen-binding site specifically binding to ANG-2 comprises in the heavy chain variable domain a CDR3H region of SEQ ID NO: 9, a CDR2H region of, SEQ ID NO: 10, and a CDR1H region of SEQ ID NO: 11, and in the light chain variable domain a CDR3L region of SEQ ID NO: 12, a CDR2L region of SEQ ID NO: 13, and a CDR1L region of SEQ ID NO: 14, and wherein iii) the bispecific antibody comprises a constant heavy chain region of human IgG1 subclass comprising the mutations I253A, H310A, and H435A and the mutations L234A, L235A and P329G (numberings according to EU Index of Kabat).

In one embodiment of the invention the patients suffering from an ocular vascular disease have not been previously treated with anti-VEGF treatment (e.g monotherapy) (are treatment naïve).

In one embodiment of the invention the patients suffering from an ocular vascular disease have been previously treated with anti-VEGF treatment (e.g monotherapy).

In one embodiment of the invention the ocular vascular disease is DME and the treatment of patients suffering from DME includes a fixed every $8^{th}$ week (Q8W) dosing schedule following treatment initiation.

In one embodiment of the invention the ocular vascular disease is DME and the treatment of patients suffering from DME includes a fixed Q12W dosing schedule following treatment initiation. In one embodiment of the invention following the treatment initiation, first one dose cycle of Q8W follows before the fixed Q12W dosing schedule.

In one embodiment of the invention the ocular vascular disease is DME and the treatment of patients suffering from DME includes following treatment initiation a dosing schedule that extends the administration interval in stable absence of disease, or shortens the interval if there is disease activity. In one embodiment of the invention such dosing schedule includes that the patient receives Q4W or Q8W or Q12W or Q16W dosing, dependent on their disease state. In one embodiment of the invention the stable absence of disease is determined as Central Subfield Thickness (CST) increased by <50 μm; and/or Best Corrected Visual Acuity (BCVA/ETDRS) decreased by <5 letters and the disease activity is determined as Central Subfield Thickness (CST) increased by ≥50 μm; and/or Best Corrected Visual Acuity (BCVA/ETDRS) decreased by ≥5 letters.

In one embodiment of the invention the ocular vascular disease is AMD and the treatment of patients suffering from AMD includes following treatment initiation a dosing schedule that extends the administration interval in stable absence of disease, or shortens the interval if there is disease activity. In one embodiment of the invention such dosing schedule includes that the patient receives Q4W or Q8W or Q12W or Q16W dosing, dependent on their disease state. In one embodiment of the invention the stable absence of disease is determined as Central Subfield Thickness (CST) increased by <50 μm; and/or Best Corrected Visual Acuity (BCVA/ETDRS) decreased by <5 letters and the disease activity is determined as Central Subfield Thickness (CST) increased by ≥50 μm; and/or Best Corrected Visual Acuity (BCVA/ETDRS) decreased by ≥5 letters.

DETAILED DESCRIPTION OF THE INVENTION

Figure 1:
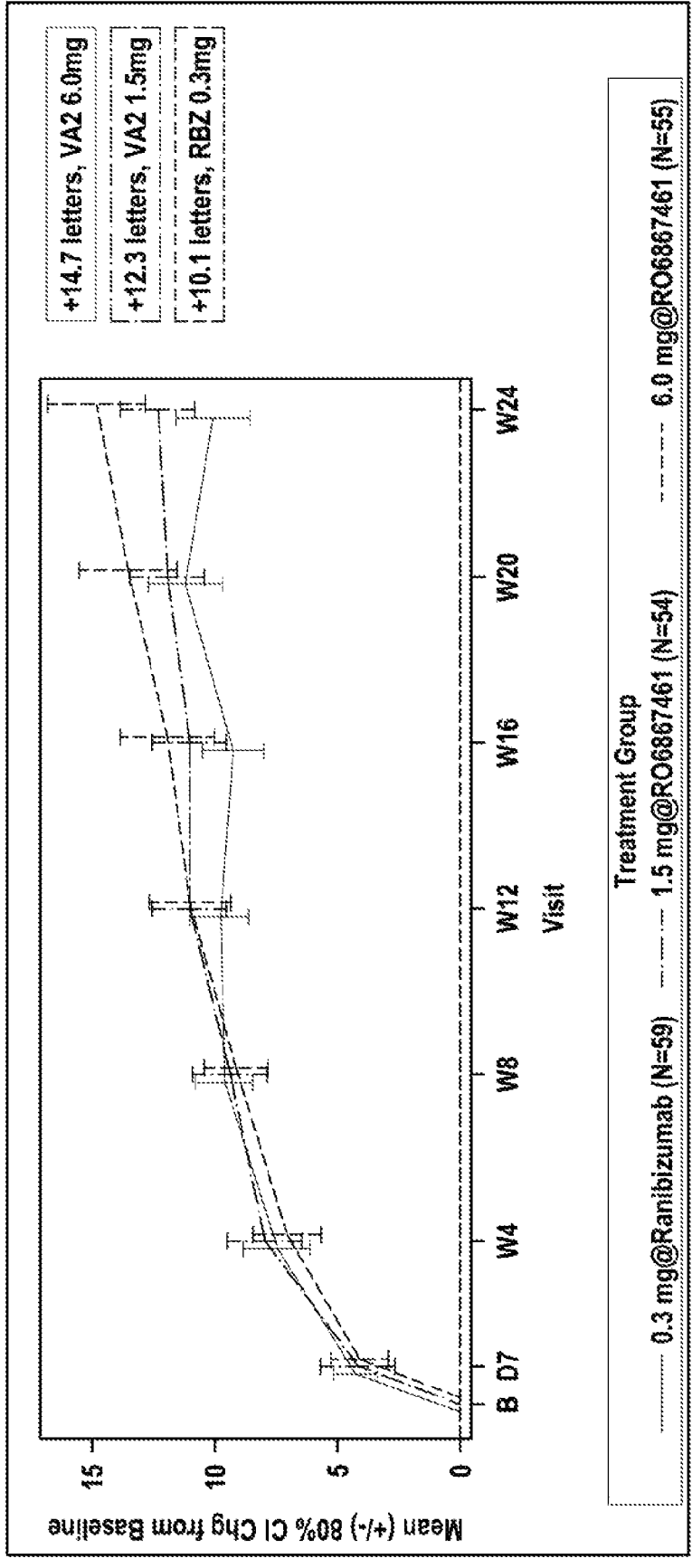
FIG. 1: BCVA change of DME patients treated from Baseline over Time to Week 24 (treatment naive patients). VA2 refers to the bispecific anti-VEGF/ANG2 antibody RO6867461 comprising the amino acid sequences of SEQ ID NO: 17, of SEQ ID NO: 18, of SEQ ID NO: 19, and of SEQ ID NO: 20 (administered intravitreally with a 6.0 mg or 1.5 mg dose), RBZ refers to ranibizumab (Lucentis®) ((administered intravitreally with a 0.3 mg dose))

According to one aspect of the present invention, methods are provided for the treatment of patients suffering from an ocular vascular disease the method comprising administering to the patient an effective amount of a bispecific antibody which binds to human vascular endothelial growth factor (VEGF) and to human angiopoietin-2 (ANG-2), wherein the bispecific antibody is administered (is to be administered) intravitreally every 8 weeks or less frequently (in one embodiment every 9 weeks or less frequently; in one embodiment every 10 weeks or less frequently; in one embodiment every 11 weeks or less frequently; in one embodiment every 12 weeks or less frequently; in one embodiment every 13 weeks or less frequently; in one embodiment every 14 weeks or less frequently; in one embodiment every 15 weeks or less frequently).

One embodiment of the invention is a method of treating a patient suffering from a ocular vascular disease the method comprising administering to the patient an effective amount of a bispecific antibody which binds to human vascular endothelial growth factor (VEGF) and to human angiopoietin-2 (ANG-2), wherein the patient gains 12 or more letters (in one embodiment 13 or more letters, in one embodiment 14 or more letters, in one embodiment 15 or more letters) of Best Corrected Visual Acuity (BCVA) measured using Early Treatment Diabetic Retinopathy Study (ETDRS) like charts, compared to the patient's BCVA letter score prior to the dosing of the bispecific VEGF/ANG2 antibody. In one embodiment the bispecific antibody is administered (is to be administered) intravitreally every 8 weeks or less frequently (in one embodiment every 9 weeks or less frequently; in one embodiment every 10 weeks or less frequently; in one embodiment every 11 weeks or less frequently; in one embodiment every 12 weeks or less frequently; in one embodiment every 13 weeks or less frequently; in one embodiment every 14 weeks or less frequently; in one embodiment every 15 weeks or less frequently).

One embodiment of the invention is a method of treating a patient suffering from a ocular vascular disease the method comprising administering to the patient an effective amount of a bispecific antibody which binds to human vascular endothelial growth factor (VEGF) and to human angiopoietin-2 (ANG-2), wherein the patient experiences an improvement in vision subsequent to the administration of the bispecific VEGF/ANG2 antibody as measured by gaining 12 or more letters (in one embodiment 13 or more letters, in one embodiment 14 or more letters, in one embodiment 15 or more letters) of Best Corrected Visual Acuity (BCVA) measured using Early Treatment Diabetic Retinopathy Study (ETDRS) like charts, compared to the patient's BCVA letter score prior to the dosing of the bispecific VEGF/ANG2 antibody. In one embodiment the bispecific antibody is administered (is to be administered) intravitreally every 8 weeks or less frequently (in one embodiment every 9 weeks or less frequently; in one embodiment every 10 weeks or less frequently; in one embodiment every 11 weeks or less frequently; in one embodiment every 12 weeks or less frequently; in one embodiment every 13 weeks or less frequently; in one embodiment every 14 weeks or less frequently; in one embodiment every 15 weeks or less frequently).

In one embodiment of the invention the gain of letters in the BCVA/ETDRS letter score is measured at 4 weeks, and/or at 8 weeks, and/or at 12 weeks, and/or at 16 weeks, and/or at 20 weeks, and/or at 24 weeks after treatment start, respectively.

In one embodiment of the invention the gain of letters in the BCVA/ETDRS letter score is measured at 24 weeks, and/or at 25 weeks, and/or at 26 weeks, and/or at 27 weeks, and/or at 28 weeks, and/or at 29 weeks, and/or at 30 weeks, and/or at 31 weeks, and/or at 32 weeks, and/or at 33 weeks, and/or at 34 weeks, and/or at 35 weeks, and/or at 36 weeks, and/or at 37 weeks, and/or at 38 weeks, and/or at 39 weeks, and/or at 40 weeks, and/or at 41 weeks, and/or at 42 weeks, and/or at 43 weeks, and/or at 44 weeks, and/or at 45 weeks, and/or at 46 weeks, and/or at 47 weeks, and/or at 48 weeks, and/or at 49 weeks, and/or at 50 weeks, and/or at 51 weeks, and/or at 52 weeks, and/or at 53 weeks, and/or at 54 weeks, and/or at 55 weeks, and/or at 56 weeks, and/or at 57 weeks, and/or at 58 weeks, and/or at 59 weeks, and/or at 60 weeks after treatment start, respectively. In one embodiment of the invention the gain of letters in the BCVA/ETDRS letter score is measured at 45 weeks, and/or at 46 weeks, and/or at 47 weeks, and/or at 48 weeks, and/or at 49 weeks, and/or at 50 weeks, and/or at 51 weeks, and/or at 52 weeks, and/or at 53 weeks, and/or at 54 weeks, and/or at 55 weeks, and/or at 56 weeks, and/or at 57 weeks, and/or at 58 weeks, and/or at 59 weeks, and/or at 60 weeks after treatment start, respectively.

In one embodiment of the invention the method is used to prolong the time to retreatment and/or to prolong the time to loss of visual acuity and, wherein the retreatment with the bispecific antibody is administered in case of a disease activity which is determined as Central Subfield Thickness (CST) increase by ≥50 μm (in one embodiment using spectral domain optical coherence tomography (SD-OCT)); and/or Best Corrected Visual Acuity (BCVA/ETDRS) decrease by ≥5 letters.

One embodiment of the invention is a bispecific antibody which binds to human vascular endothelial growth factor (VEGF) and to human angiopoietin-2 (ANG-2), for use in the treatment of an ocular vascular disease, wherein the bispecific antibody is administered (is to be administered) intravitreally every 8 weeks or less frequently (in one embodiment every 9 weeks or less frequently; in one embodiment every 10 weeks or less frequently; in one embodiment every 11 weeks or less frequently; in one embodiment every 12 weeks or less frequently; in one embodiment every 13 weeks or less frequently; in one embodiment every 14 weeks or less frequently; in one embodiment every 15 weeks or less frequently).

One embodiment of the invention is a bispecific antibody which binds to human vascular endothelial growth factor (VEGF) and to human angiopoietin-2 (ANG-2), for use in the treatment of a patient suffering from an ocular vascular disease, wherein the patient gains 12 or more letters (in one embodiment 13 or more letters, in one embodiment 14 or more letters, in one embodiment 15 or more letters) of Best Corrected Visual Acuity (BCVA) measured using Early Treatment Diabetic Retinopathy Study (ETDRS) like charts, compared to the patient's BCVA letter score prior to the dosing of the bispecific VEGF/ANG2 antibody. In one embodiment the bispecific antibody is administered (is to be administered) intravitreally every 8 weeks or less frequently (in one embodiment every 9 weeks or less frequently; in one embodiment every 10 weeks or less frequently; in one embodiment every 11 weeks or less frequently; in one embodiment every 12 weeks or less frequently; in one embodiment every 13 weeks or less frequently; in one embodiment every 14 weeks or less frequently; in one embodiment every 15 weeks or less frequently).

One embodiment of the invention is a bispecific antibody which binds to human vascular endothelial growth factor (VEGF) and to human angiopoietin-2 (ANG-2), for use in the treatment of a patient suffering from an ocular vascular disease, wherein the patient experiences an improvement in vision subsequent to the (intravitreal) administration of the bispecific VEGF/ANG2 antibody as measured by gaining 12 or more letters (in one embodiment 13 or more letters, in one embodiment 14 or more letters, in one embodiment 15 or more letters) of Best Corrected Visual Acuity (BCVA) measured using Early Treatment Diabetic Retinopathy Study (ETDRS) like charts, compared to the patient's BCVA letter score prior to the dosing of the bispecific VEGF/ANG2 antibody. In one embodiment the bispecific antibody is administered (is to be administered) intravitreally every 8 weeks or less frequently (in one embodiment every 9 weeks or less frequently; in one embodiment every 10 weeks or less frequently; in one embodiment every 11 weeks or less frequently; in one embodiment every 12 weeks or less frequently; in one embodiment every 13 weeks or less frequently; in one embodiment every 14 weeks or less frequently; in one embodiment every 15 weeks or less frequently).

In one embodiment of the invention the gain of letters in the BCVA/ETDRS letter score is measured at 4 weeks, and/or at 8 weeks, and/or at 12 weeks, and/or at 16 weeks, and/or at 20 weeks, and/or at 24 weeks after treatment start, respectively.

In one embodiment of the invention the gain of letters in the BCVA/ETDRS letter score is measured at 45 weeks, and/or at 46 weeks, and/or at 47 weeks, and/or at 48 weeks, and/or at 49 weeks, and/or at 50 weeks, and/or at 51 weeks, and/or at 52 weeks, and/or at 53 weeks, and/or at 54 weeks, and/or at 55 weeks, and/or at 56 weeks, and/or at 57 weeks, and/or at 58 weeks, and/or at 59 weeks, and/or at 60 weeks after treatment start, respectively.

In one embodiment of the invention such bispecific antibody (for use) is used to prolong the time to retreatment and/or to prolong the time to loss of visual acuity and, wherein the retreatment with the bispecific antibody is administered in case of a disease activity which is determined as Central Subfield Thickness (CST) increase by ≥50 µm (in one embodiment using spectral domain optical coherence tomography (SD-OCT)); and/or Best Corrected Visual Acuity (BCVA/ETDRS) decrease by ≥5 letters.

One embodiment of the invention is a medicament or pharmaceutical formulation comprising a bispecific antibody which binds to human vascular endothelial growth factor (VEGF) and to human angiopoietin-2 (ANG-2), for use in the treatment of an ocular vascular disease, wherein the bispecific antibody is administered (is to be administered) intravitreally every 8 weeks or less frequently (in one embodiment every 9 weeks or less frequently; in one embodiment every 10 weeks or less frequently; in one embodiment every 11 weeks or less frequently; in one embodiment every 12 weeks or less frequently; in one embodiment every 13 weeks or less frequently; in one embodiment every 14 weeks or less frequently; in one embodiment every 15 weeks or less frequently).

One embodiment of the invention is a medicament or pharmaceutical formulation comprising a bispecific antibody which binds to human vascular endothelial growth factor (VEGF) and to human angiopoietin-2 (ANG-2), for use in the treatment of a patient suffering from an ocular vascular disease, wherein the patient gains 12 or more letters (in one embodiment 13 or more letters, in one embodiment 14 or more letters, in one embodiment 15 or more letters) of Best Corrected Visual Acuity (BCVA) measured using Early Treatment Diabetic Retinopathy Study (ETDRS) like charts, compared to the patient's BCVA letter score prior to the dosing of the bispecific VEGF/ANG2 antibody. In one embodiment the bispecific antibody is administered (is to be administered) intravitreally every 8 weeks or less frequently (in one embodiment every 9 weeks or less frequently; in one embodiment every 10 weeks or less frequently; in one embodiment every 11 weeks or less frequently; in one embodiment every 12 weeks or less frequently; in one embodiment every 13 weeks or less frequently; in one embodiment every 14 weeks or less frequently; in one embodiment every 15 weeks or less frequently).

One embodiment of the invention is a medicament or pharmaceutical formulation comprising a bispecific antibody which binds to human vascular endothelial growth factor (VEGF) and to human angiopoietin-2 (ANG-2), for use in the treatment of a patient suffering from an ocular vascular disease, wherein the patient experiences an improvement in vision subsequent to the (intravitreal) administration of the bispecific VEGF/ANG2 antibody as measured by gaining 12 or more letters (in one embodiment 13 or more letters, in one embodiment 14 or more letters, in one embodiment 15 or more letters) of Best Corrected Visual Acuity (BCVA) measured using Early Treatment Diabetic Retinopathy Study (ETDRS) like charts, compared to the patient's BCVA letter score prior to the dosing of the bispecific VEGF/ANG2 antibody. In one embodiment the bispecific antibody is administered (is to be administered) intravitreally every 8 weeks or less frequently (in one embodiment every 9 weeks or less frequently; in one embodiment every 10 weeks or less frequently; in one embodiment every 11 weeks or less frequently; in one embodiment every 12 weeks or less frequently; in one embodiment every 13 weeks or less frequently; in one embodiment every 14 weeks or less frequently; in one embodiment every 15 weeks or less frequently).

In one embodiment of the invention the gain of letters in the BCVA/ETDRS letter score is measured at 4 weeks, and/or at 8 weeks, and/or at 12 weeks, and/or at 16 weeks, and/or at 20 weeks, and/or at 24 weeks after treatment start, respectively.

In one embodiment of the invention the gain of letters in the BCVA/ETDRS letter score is measured at 45 weeks, and/or at 46 weeks, and/or at 47 weeks, and/or at 48 weeks, and/or at 49 weeks, and/or at 50 weeks, and/or at 51 weeks, and/or at 52 weeks, and/or at 53 weeks, and/or at 54 weeks, and/or at 55 weeks, and/or at 56 weeks, and/or at 57 weeks, and/or at 58 weeks, and/or at 59 weeks, and/or at 60 weeks after treatment start, respectively.

In one embodiment of the invention such medicament or pharmaceutical formulation is used to prolong the time to retreatment and/or to prolong the time to loss of visual acuity and, wherein the retreatment with the bispecific antibody is administered in case of a disease activity which is determined as Central Subfield Thickness (CST) increase by ≥50 µm (in one embodiment using spectral domain optical coherence tomography (SD-OCT)); and/or Best Corrected Visual Acuity (BCVA/ETDRS) decrease by ≥5 letters.

One embodiment of the invention is the use of a bispecific antibody which binds to human vascular endothelial growth factor (VEGF) and to human angiopoietin-2 (ANG-2), for the manufacture of a medicament for use in the treatment of an ocular vascular disease, wherein the bispecific antibody is administered (is to be administered) intravitreally every 8 weeks or less frequently (in one embodiment every 9 weeks or less frequently; in one embodiment every 10 weeks or less frequently; in one embodiment every 11 weeks or less frequently; in one embodiment every 12 weeks or less frequently; in one embodiment every 13 weeks or less frequently; in one embodiment every 14 weeks or less frequently; in one embodiment every 15 weeks or less frequently).

One embodiment of the invention is the use of a bispecific antibody which binds to human vascular endothelial growth factor (VEGF) and to human angiopoietin-2 (ANG-2), for the manufacture of a medicament for use in the treatment of an ocular vascular disease, wherein the patient gains 12 or more letters (in one embodiment 13 or more letters, in one embodiment 14 or more letters, in one embodiment 15 or more letters) of Best Corrected Visual Acuity (BCVA) measured using Early Treatment Diabetic Retinopathy Study (ETDRS) like charts, compared to the patient's BCVA letter score prior to the dosing of the bispecific VEGF/ANG2 antibody. In one embodiment the bispecific antibody is administered (is to be administered) intravitreally every 8 weeks or less frequently (in one embodiment every 9 weeks or less frequently; in one embodiment every 10 weeks or less frequently; in one embodiment every 11 weeks or less frequently; in one embodiment every 12 weeks or less frequently; in one embodiment every 13 weeks or less frequently; in one embodiment every 14 weeks or less frequently; in one embodiment every 15 weeks or less frequently).

One embodiment of the invention is the use of a bispecific antibody which binds to human vascular endothelial growth factor (VEGF) and to human angiopoietin-2 (ANG-2), for the manufacture of a medicament for use in the treatment of an ocular vascular disease, wherein the patient experiences an improvement in vision subsequent to the (intravitreal) administration of the bispecific VEGF/ANG2 antibody as measured by gaining 12 or more letters (in one embodiment 13 or more letters, in one embodiment 14 or more letters, in one embodiment 15 or more letters) of Best Corrected Visual Acuity (BCVA) measured using Early Treatment Diabetic Retinopathy Study (ETDRS) like charts, compared to the patient's BCVA letter score prior to the dosing of the bispecific VEGF/ANG2 antibody. In one embodiment the bispecific antibody is administered (is to be administered) intravitreally every 8 weeks or less frequently (in one embodiment every 9 weeks or less frequently; in one embodiment every 10 weeks or less frequently; in one embodiment every 11 weeks or less frequently; in one embodiment every 12 weeks or less frequently; in one embodiment every 13 weeks or less frequently; in one embodiment every 14 weeks or less frequently; in one embodiment every 15 weeks or less frequently).

In one embodiment of the invention the gain of letters in the BCVA/ETDRS letter score is measured at 4 weeks, and/or at 8 weeks, and/or at 12 weeks, and/or at 16 weeks, and/or at 20 weeks, and/or at 24 weeks after treatment start, respectively.

In one embodiment of the invention the gain of letters in the BCVA/ETDRS letter score is measured at 45 weeks, and/or at 46 weeks, and/or at 47 weeks, and/or at 48 weeks, and/or at 49 weeks, and/or at 50 weeks, and/or at 51 weeks, and/or at 52 weeks, and/or at 53 weeks, and/or at 54 weeks, and/or at 55 weeks, and/or at 56 weeks, and/or at 57 weeks, and/or at 58 weeks, and/or at 59 weeks, and/or at 60 weeks after treatment start, respectively.

In one embodiment of the invention medicament is used to prolong the time to retreatment and/or to prolong the time to loss of visual acuity and, wherein the retreatment with the bispecific antibody is administered in case of a disease activity which is determined as Central Subfield Thickness (CST) increase by ≥50 μm (in one embodiment using spectral domain optical coherence tomography (SD-OCT)); and/or Best Corrected Visual Acuity (BCVA/ETDRS) decrease by ≥5 letters.

In one embodiment BCVA determination in such method, use, bispecific antibody (for use), medicament or pharmaceutical formulation is based on the Early Treatment of Diabetic Retinopathy Study (ETDRS) Protocol adapted visual acuity charts and is assessed at a starting distance of 4 meters.

Such method, use, bispecific antibody (for use), medicament or pharmaceutical formulation may comprise sequentially administering initial doses ("treatment initiation") (e.g. 3 to 7 monthly administrations; in one embodiment the treatment initiation includes 3 to 4 monthly administrations, in one embodiment the treatment initiation includes 4 to 5 monthly administrations; in one embodiment the treatment initiation includes 4 to 6 monthly administrations; in one embodiment the treatment initiation includes at least 4 monthly administrations; in one embodiment the treatment initiation includes 5 to 7 monthly administrations, in one embodiment the treatment initiation includes 6 monthly administrations) followed by one or more secondary doses of a therapeutically effective amount of the bispecific antibody, medicament or pharmaceutical formulation.

In one embodiment of the invention the bispecific antibody, medicament or pharmaceutical formulation is administered every 10 to 12 weeks (following treatment initiation).

In one embodiment of the invention the bispecific antibody, medicament or pharmaceutical formulation is administered every 11 to 13 weeks (following treatment initiation).

In one embodiment of the invention the bispecific antibody, medicament or pharmaceutical formulation is administered every 12 to 14 weeks (following treatment initiation).

In one embodiment of the invention the bispecific antibody, medicament or pharmaceutical formulation is administered every 13 to 15 weeks (following treatment initiation).

In one embodiment of the invention the bispecific antibody, medicament or pharmaceutical formulation is administered every 14 to 16 weeks (following treatment initiation).

In one embodiment of the invention the bispecific antibody, medicament or pharmaceutical formulation is administered every 10 to 11 weeks, or every 11 to 12 weeks, or every 12 to 13 weeks, or every 13 to 14 weeks, or every 14 to 15 weeks, or every 15 to 16 weeks (following treatment initiation, respectively).

In one embodiment of the invention the bispecific antibody, medicament or pharmaceutical formulation is administered every 10 weeks, or every 11 weeks, or every 12 weeks, or every 13 weeks, or every 14 weeks, or every 16 weeks (following treatment initiation, respectively).

In one embodiment of the invention the bispecific antibody, medicament or pharmaceutical formulation is administered in a dose of about 5 to 7 mg (at each treatment). In one embodiment the bispecific antibody is administered in a dose of 6 mg+/−10% (at each treatment). In one embodiment the bispecific antibody is administered in a dose of about 6 mg (at each treatment). (in one embodiment in a dose of 6 mg (at each treatment))

In one embodiment of the invention the bispecific antibody, medicament or pharmaceutical formulation is administered in a concentration of about 30 mg/ml of the bispecific antibody. In one embodiment of the invention the bispecific antibody, medicament or pharmaceutical formulation is administered in a concentration of about 120 mg/ml of the bispecific antibody.

The terms "ocular vascular disease" and "vascular eye disease" are used interchangeably herein and include, but are not limited to intraocular neovascular syndromes such as diabetic retinopathy, diabetic macular edema, retinopathy of prematurity, neovascular glaucoma, (branch) retinal vein occlusions, central retinal vein occlusions, macular degeneration, age-related macular degeneration, retinitis pigmentosa, retinal angiomatous proliferation, macular telangectasia, ischemic retinopathy, iris neovascularization, intraocular neovascularization, corneal neovascularization, retinal neovascularization, choroidal neovascularization, and retinal degeneration. (Garner, A., Vascular diseases, In: Pathobiology of ocular disease, A dynamic approach, Gamer, A., and Klintworth, G. K., (eds.), 2nd edition, Marcel Dekker, New York (1994), pp. 1625-1710). As used herein, ocular vascular disorder refers to any pathological conditions characterized by altered or unregulated proliferation and invasion of new blood vessels into the structures of ocular tissues such as the retina or cornea. In one embodiment the ocular vascular disease is selected from the group consisting of: wet age-related macular degeneration (wet AMD), neovascular AMD (nAMD), diabetic macular edema (DME), cystoid macular edema (CME), non-proliferative diabetic retinopathy (NPDR), proliferative diabetic retinopathy (PDR), macular edema secondary to central retinal vein occlusion, secondary to hemiretinal vein occlusion or secondary to branch vein 30 occlusion, retinitis, conjunctivitis, uveitis, choroiditis, choroidal neovascularization (CNV) secondary to ocular inflammation including secondary to ocular histoplasmosis or presumed histoplasmosis or choroiditis; myopic choroidal neovascularization (mCNV). And choroidal neovascularization secondary to trauma, retinopathy of prematurity and rubeosis iridis/rubeotic glaucoma, and other ophthalmic diseases wherein the eye disease or disorder is associated with ocular neovascularization, vascular leakage, and/or retinal edema. So the anti-VEGF/ANG2 bispecific antibodies for use and the methods described herein are useful in the prevention and treatment of wet AMD, nAMD CME, DME, NPDR, PDR, and uveitis, also preferably wet AMD, nAMD, also preferably DME, CME, NPDR and PDR, and also particularly wet AMD. In some embodiments, the ocular vascular disease is selected from the group consisting of wet age-related macular degeneration (wet AMD), neovascular age-related macular degeneration (nAMD), (diabetic) macular edema, retinal vein occlusions, retinopathy of prematurity, and diabetic retinopathy.

Other diseases/conditions associated with corneal neovascularization (or which may be the cause of corneal neovascularization) include, but are not limited to, epidemic keratoconjunctivitis, Vitamin A deficiency, contact lens overwear, atopic keratitis, superior limbic keratitis, pterygium keratitis sicca, sjogrens syndrome, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, rheumatoid arthritis, systemic lupus, polyarteritis, trauma, Wegeners sarcoidosis, Scleritis, Steven's Johnson disease, periphigoid radial keratotomy, and corneal graph rejection.

Diseases/conditions associated with retinal/choroidal neovascularization (or which may be the cause of retinal/choroidal neovascularization) include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, retinitis pigmentosa, retina edema (including macular edema), Eales disease, Bechets disease, infections causing a retinitis or choroiditis, presumed ocular histoplasmosis, Bests disease, myopia, optic (disc) pits, Stargardts disease, pars planitis, chronic retinal detachment, hyperviscosity syndromes, toxoplasmosis, trauma and post-laser complications. Other diseases include, but are not limited to, diseases associated with rubeosis (neovascularization of the angle) and diseases caused by the abnormal proliferation of fibrovascular or fibrous tissue including all forms of proliferative vitreoretinopathy.

Retinopathy of prematurity (ROP) is a disease of the eye that affects prematurely born babies. It is thought to be caused by disorganized growth of retinal blood vessels which may result in scarring and retinal detachment. ROP can be mild and may resolve spontaneously, but may lead to (total) blindness in serious cases. As such, all preterm babies are at risk for ROP, and very low birth weight is an additional risk factor. Both oxygen toxicity and relative hypoxia can contribute to the development of ROP.

Macular degeneration is a medical condition predominantly found in elderly adults in which the center of the inner lining of the eye, known as the macula area of the retina, suffers thinning, atrophy, and in some cases, bleeding. This can result in loss of central vision, which entails inability to see fine details, to read, or to recognize faces. According to the American Academy of Ophthalmology, it is the leading cause of central vision loss (blindness) in the United States today for those over the age of fifty years. Although some macular dystrophies that affect younger individuals are sometimes referred to as macular degeneration, the term generally refers to age-related macular degeneration (AMD or ARMD).

"Age-related macular degeneration (AMD)", as used herein, refers to a serious eye condition when the small central portion of the retina, known as the macula, deteriorates. AMD includes wet AMD and neovascular AMD. The wet form of AMD (wet AMD, wAMD or also called neovascular AMD, nAMD) is characterized by the growth of abnormal blood vessels from the choroid underneath the macula. This is called choroidal neovascularization. These blood vessels leak blood and fluid (below and) into the retina, causing (elevation of the retina and) distortion of vision that makes straight lines look wavy, as well as blind spots and loss of central vision. These abnormal blood vessels eventually scar, leading to permanent loss of central vision. The symptoms of AMD include dark, blurry areas in the center of vision; and diminished or changed color perception. AMD can be detected in a routine eye exam. One of the most common early signs of macular degeneration is the presence of drusen which are tiny yellow deposits under the retina and pigment clumping.

Advanced AMD, which is responsible for profound vision loss, has two forms: dry and wet. Central geographic atrophy, the dry form of advanced AMD, results from atrophy to the retinal pigment epithelial layer below the retina, which causes vision loss through loss of photoreceptors (rods and cones) in the central part of the eye. While no treatment is available for this condition, vitamin supplements with high doses of antioxidants, lutein and zeaxanthin, have been demonstrated by the National Eye Institute and others to slow the progression of dry macular degeneration and in some patients, improve visual acuity.

Retinitis pigmentosa (RP) is a group of genetic eye conditions. In the progression of symptoms for RP, night blindness generally precedes tunnel vision by years or even decades. Many people with RP do not become legally blind until their 40s or 50s and retain some sight all their life. Others go completely blind from RP, in some cases as early as childhood. Progression of RP is different in each case. RP is a type of hereditary retinal dystrophy, a group of inherited disorders in which abnormalities of the photoreceptors (rods and cones) or the retinal pigment epithelium (RPE) of the retina lead to progressive visual loss. Affected individuals first experience defective dark adaptation or nyctalopia (night blindness), followed by reduction of the peripheral visual field (known as tunnel vision) and, sometimes, loss of central vision late in the course of the disease.

Macular edema occurs when fluid and protein deposits collect on or under the macula of the eye, the central area of the retina responsible for fine vision, causing it to thicken and swell. The swelling may distort a person's central vision, as the macula is near the center of the retina at the back of the eyeball. This area holds tightly packed cones that provide sharp, clear central vision to enable a person to see form, color, and detail that is directly in the line of sight. Cystoid macular edema is a type of macular edema that includes cyst formation.

"Diabetic Macular Edema" (DME), as used herein, refers to a serious eye condition that affects people with diabetes (type 1 or 2). Macular edema occurs when blood vessels in the retina leak into the macula and fluid and protein deposits collect on or under the macula of the eye and causes it to thicken and swell (edema). The swelling may distort a person's central vision, as the macula is near the center of the retina at the back of the eyeball. The primary symptoms of DME include, but are not limited to, blurry vision, floaters, loss of contrast, double vision, and eventual loss of vision. The pathology of DME is characterized by breakdown of inner the blood-retinal barrier, normally preventing fluid movement in the retina, thus allowing fluid to accumulate in the retinal tissue, and presence of retinal thickening. DME is presently diagnosed during an eye examination consisting of a visual acuity test, which determines the smallest letters a person can read on a standardized chart, a dilated eye exam to check for signs of the disease, imaging tests such as optical coherence tomography (OCT) or fluorescein angiography (FA) and tonometry, an instrument that measures pressure inside the eye. The following studies are also performed to determine treatment: optical coherence tomography (OCT), fluorescein angiography, and color stereo fundus photography. DME can be broadly characterized into two main categories—Focal and Diffuse. Focal DME is characterized by specific areas of separate and distinct leakage in the macula with sufficient macular blood flow. Diffuse DME results from leakage of the entire capillary bed surrounding the macula, resulting from a breakdown of the inner blood-retina barrier of the eye. In addition to Focal and Diffuse, DME is also categorized based on clinical exam findings into clinically significant macular edema (CSME), non-CSME and CSME with central involvement (CSME-CI), which involves the fovea. The present invention includes methods to treat the above-mentioned categories of DME.

Best Corrected Visual Acuity (BCVA) is determined using methodology adapted from the 4-meter Early Treatment Diabetic Retinopathy Study [ETDRS] protocol (using Early Treatment Diabetic Retinopathy Study (ETDRS) like charts) and resulting in the respective letter score.

Disease activity is determined e.g. via reduction of the BCVA/ETDRs letter score and/or e.g. via the macular thickening by spectral domain optical coherence tomography (SD-OCT) involving the center of the macula as central subfield thickness (CST) (also known as center subfoveal thickness). In one preferred embodiment Central Subfield Thickness (CST) is determined using spectral domain optical coherence tomography (SD-OCT): In one preferred embodiment CST is measured by spectral domain optical coherence tomography (SD-OCT) with a Spectralis™ device; in one preferred embodiment CST is measured by spectral domain optical coherence tomography (SD-OCT) with a Cirrus™ device; in one embodiment CST is measured by spectral domain optical coherence tomography (SD-OCT) with a Topcon™ device; in one embodiment CST is measured by spectral domain optical coherence tomography (SD-OCT) with a Optovue™ device). As used herein, the term "a patient suffering from" refers to a human that exhibits one or more symptoms or indications of, and/or who has been diagnosed with an ocular vascular disease as described herein. The term "a patient suffering from" may also include, e.g., subjects who, prior to treatment, exhibit (or have exhibited) one or more indications of a vascular eye disease such as, e.g., retinal angiogenesis, neovascularization, vascular leak, retinal thickening of the center of the fovea, hard, yellow exudates of the center of the fovea with adjacent retinal thickening, and at least 1 disc area of retinal thickening, any part of which is within 1 disc diameter of the center of the fovea, blurry vision, floaters, loss of contrast, double vision, and eventual loss of vision.

As used herein, the term "a patient suffering from" may include a subset of population which is more susceptible to DME or AMD or may show an elevated level of a DME-associated or an AMD-associated biomarker. For example, "a subject in need thereof" may include a subject suffering from diabetes for more than 10 years, have frequent high blood sugar levels or high fasting blood glucose levels. In certain embodiments, the term "a patient suffering from" includes a subject who, prior to or at the time of administration of the bispecific anti-VEGF/ANG2 antibody, has or is diagnosed with diabetes. In certain embodiments, the term "a patient suffering from" includes a subject who, prior to or at the time of administration of the anti-VEGF/ANG2 antibody, is more than 50 years old. In some embodiments, the term "a patient suffering from" includes subjects who are smokers, or subjects with high blood pressure or high cholesterol.

The present invention includes methods or bispecific antibodies (for use), medicaments or pharmaceutical formulations for treating, preventing or reducing the severity of an ocular vascular disease comprising administering a therapeutically effective amount of a bispecific anti-VEGF/ANG2 antibody (or a medicament or pharmaceutical formulation comprising the bispecific anti-VEGF/ANG2 antibody) to a subject in need thereof, wherein the bispecific antibody, medicament or pharmaceutical formulation comprising such bispecific anti-VEGF/ANG2 antibody is administered (intravitreally) to the subject in multiple doses, e.g., as part of a specific therapeutic dosing regimen.

One embodiment of the invention is the method of treatment, use, bispecific antibody (for use), medicament or pharmaceutical formulation as described herein wherein patients suffering from an ocular vascular disease have not been previously treated with anti-VEGF treatment (e.g monotherapy) (are treatment naïve).

One embodiment of the invention is the method of treatment, use, bispecific antibody (for use), medicament or pharmaceutical formulation as described herein wherein patients suffering from an ocular vascular disease have been previously treated with anti-VEGF treatment (e.g monotherapy).

One embodiment of the invention is the method of treatment, use, bispecific antibody (for use), medicament or pharmaceutical formulation as described herein wherein the ocular vascular disease is DME and the treatment of patients suffering from DME includes a fixed every 8th week (Q8W) dosing schedule following treatment initiation (In one embodiment the treatment initiation includes 5 to 7 monthly administrations; in one embodiment the treatment initiation includes 6 monthly administrations).

One embodiment of the invention is the method of treatment, use, bispecific antibody (for use), medicament or pharmaceutical formulation as described herein wherein the ocular vascular disease is DME and the treatment of patients suffering from DME includes a fixed Q12W dosing schedule following treatment initiation (In one embodiment the treatment initiation includes 5 to 7 monthly administrations; in one embodiment the treatment initiation includes 6 monthly administrations). In one embodiment following the treatment initiation, first one dose cycle of Q8W follows before the fixed Q12W dosing schedule.

One embodiment of the invention is the method of treatment, use, bispecific antibody (for use), medicament or pharmaceutical formulation as described herein wherein the ocular vascular disease is DME and the treatment of patients suffering from DME includes following treatment initiation a dosing schedule that extends the administration interval in stable absence of disease, or shortens the interval if there is disease activity (In one embodiment the treatment initiation includes 3 to 7 monthly administrations; in one embodiment the treatment initiation includes 3 to 5 monthly administrations; in one embodiment the treatment initiation includes at least 4 monthly administrations; in one embodiment the treatment initiation includes 4 to 6 monthly administrations). In one embodiment such dosing schedule includes that the patient receives Q4W or Q8W or Q12W or Q16W dosing, dependent on their disease state. In one embodiment the stable absence of disease is determined as Central Subfield Thickness (CST) increased by <50 μm Best Corrected Visual Acuity (BCVA/ETDRS) decreased by <5 letters and the disease activity is determined as Central Subfield Thickness (CST) increased by ≥50 μm Best Corrected Visual Acuity (BCVA/ETDRS) decreased by ≥5 letters.

In one embodiment the stable absence of disease is determined as

Central Subfield Thickness (CST) is below about 300 μm (In one embodiment below 325 μm measured by spectral domain optical coherence tomography (SD-OCT) with a Spectralis™ device; in one embodiment below 315 μm measured by spectral domain optical coherence tomography (SD-OCT) with a Cirrus™ device; in one embodiment below 315 μm measured by spectral domain optical coherence tomography (SD-OCT) with a Topcon™ device; in one embodiment below 295 μm measured by spectral domain optical coherence tomography (SD-OCT) with a Optovue™ device), and the disease activity is determined as Central Subfield Thickness (CST) is above about 300 μm (In one embodiment above 325 μm measured by spectral domain optical coherence tomography (SD-OCT) with a Spectralis™ device; in one embodiment above 315 μm measured by spectral domain optical coherence tomography (SD-OCT) with a Cirrus™ device; in one embodiment above 315 μm measured by spectral domain optical coherence tomography (SD-OCT) with a Topcon™ device; in one embodiment above 295 μm measured by spectral domain optical coherence tomography (SD-OCT) with a Optovue™ device).

One embodiment of the invention the method of treatment, use, bispecific antibody (for use), medicament or pharmaceutical formulation as described herein wherein the ocular vascular disease is AMD (in one embodiment wet AMD) and the treatment of patients suffering from AMD (in one embodiment wet AMD) includes following treatment initiation a dosing schedule that extends the administration interval in stable absence of disease, or shortens the interval if there is disease activity (In one embodiment the treatment initiation includes 3 to 7 monthly administrations; in one embodiment the treatment initiation includes 3 to 5 monthly administrations; in one embodiment the treatment initiation includes at least 4 monthly administrations; in one embodiment the treatment initiation includes 4 to 6 monthly administrations). In one embodiment such dosing schedule includes that the patient receives Q4W or Q8W or Q12W or Q16W dosing, dependent on their disease state. In one embodiment the stable absence of disease is determined as Central Subfield Thickness (CST) increased by <50 μm; and/or Best Corrected Visual Acuity (BCVA/ETDRS) decreased by <5 letters and the disease activity is determined as Central Subfield Thickness (CST) increased by ≥50 μm; and/or Best Corrected Visual Acuity (BCVA/ETDRS) decreased by ≥5 letters.

In one embodiment the stable absence of disease is determined as

Central Subfield Thickness (CST) is below about 300 μm (In one embodiment below 325 μm measured by spectral domain optical coherence tomography (SD-OCT) with a Spectralis™ device; in one embodiment below 315 μm measured by spectral domain optical coherence tomography (SD-OCT) with a Cirrus™ device; in one embodiment below 315 μm measured by spectral domain optical coherence tomography (SD-OCT) with a Topcon™ device; in one embodiment below 295 μm measured by spectral domain optical coherence tomography (SD-OCT) with a Optovue™ device), and the disease activity is determined as Central Subfield Thickness (CST) is above about 300 μm (In one embodiment above 325 μm measured by spectral domain optical coherence tomography (SD-OCT) with a Spectralis™ device; in one embodiment above 315 μm measured by spectral domain optical coherence tomography (SD-OCT) with a Cirrus™ device; in one embodiment above 315 μm measured by spectral domain optical coherence tomography (SD-OCT) with a Topcon™ device; in one embodiment above 295 μm measured by spectral domain optical coherence tomography (SD-OCT) with a Optovue™ device).

In one embodiment the vascular ocular disease in such method, use, bispecific antibody (for use), medicament or pharmaceutical formulation is wetAMD (nAMD).

As used herein, "antibody" refers to a binding protein that comprises antigen-binding sites. The terms "binding site" or "antigen-binding site" as used herein denotes the region(s) of an antibody molecule to which a ligand actually binds. The term "antigen-binding site" comprises an antibody heavy chain variable domains (VH) and an antibody light chain variable domains (VL) (pair of VH/VL)).

Antibody specificity refers to selective recognition of the antibody for a particular epitope of an antigen. Natural antibodies, for example, are monospecific.

"Bispecific antibodies" according to the invention are antibodies which have two different antigen-binding specificities. Antibodies of the present invention are specific for two different antigens, VEGF as first antigen and ANG-2 as second antigen.

The term "monospecific" antibody as used herein denotes an antibody that has one or more binding sites each of which bind to the same epitope of the same antigen.

The term "valent" as used within the current application denotes the presence of a specified number of binding sites in an antibody molecule. As such, the terms "bivalent", "tetravalent", and "hexavalent" denote the presence of two binding site, four binding sites, and six binding sites, respectively, in an antibody molecule. The bispecific antibodies according to the invention are preferably "bivalent".

The terms "bispecific antibody which binds to human vascular endothelial growth factor (VEGF) and to human angiopoietin-2 (ANG-2)", "bispecific anti-VEGF/ANG2 antibody" and bispecific <VEGF/ANG2> antibody" as used herein are interchangeable and refer to an antibody which has at least two different antigen-binding sites, a first one which binds to VEGF and a second one which binds to ANG2.

Bispecific anti-VEGF/ANG2 antibodies are e.g. described in WO2010040508, WO2011/117329, WO2012/131078, WO2015/083978, WO2017/197199, and WO2014/009465. WO2014/009465 describes bispecific anti-VEGF/ANG2 antibodies especially designed for treatment of ocular vascular diseases. The bispecific anti-VEGF/ANG2 antibodies of WO2014/009465 (which is incorporated herein in its entirety) are especially useful in the treatment and treatment schedules of ocular vascular diseases as described herein.

In one embodiment the bispecific antibody which binds to human vascular endothelial growth factor (VEGF) and to human angiopoietin-2 (ANG-2) is a bispecific anti-VEGF/ANG2 antibody comprising a first antigen-binding site that specifically binds to human VEGF and a second antigen-binding site that specifically binds to human ANG-2, wherein i) said first antigen-binding site specifically binding to VEGF comprises in the heavy chain variable domain a CDR3H region of SEQ ID NO: 1, a CDR2H region of SEQ ID NO: 2, and a CDR1H region of SEQ ID NO:3, and in the light chain variable domain a CDR3L region of SEQ ID NO: 4, a CDR2L region of SEQ ID NO:5, and a CDR1L region of SEQ ID NO: 6; and ii) said second antigen-binding site specifically binding to ANG-2 comprises in the heavy chain variable domain a CDR3H region of SEQ ID NO: 9, a CDR2H region of, SEQ ID NO: 10, and a CDR1H region of SEQ ID NO: 11, and in the light chain variable domain a CDR3L region of SEQ ID NO: 12, a CDR2L region of SEQ ID NO: 13, and a CDR1L region of SEQ ID NO: 14, and wherein iii) the bispecific antibody comprises a constant heavy chain region of human IgG1 subclass comprising the mutations I253A, H310A, and H435A and the mutations L234A, L235A and P329G (numberings according to EU Index of Kabat).

In one embodiment such bispecific anti-VEGF/ANG2 antibody is bivalent.

In one embodiment such bispecific anti-VEGF/ANG2 antibody is characterized in that i) said first antigen-binding site specifically binding to VEGF comprises as heavy chain variable domain VH an amino acid sequence of SEQ ID NO: 7, and as light chain variable domain VL an amino acid sequence of SEQ ID NO: 8, and ii) said second antigen-binding site specifically binding to ANG-2 comprises as heavy chain variable domain VH an amino acid sequence of SEQ ID NO: 15, and as light chain variable domain VL an amino acid sequence of SEQ ID NO: 16.

In one aspect of the invention such bispecific, bivalent antibody according to the invention is characterized in comprising a) the heavy chain and the light chain of a first full length antibody that specifically binds to VEGF;

b) the modified heavy chain and modified light chain of a second full length antibody that specifically binds to ANG-2, wherein the constant domains CL and CH1 are replaced by each other.

This bispecific, bivalent antibody format for the bispecific antibody specifically binding to human vascular endothelial growth factor (VEGF) and human angiopoietin-2 (ANG-2) is described in WO 2009/080253 (including Knobs-into-Holes modified CH3 domains). The antibodies based on this bispecific, bivalent antibody format are named CrossMAbs.

In one embodiment such bispecific, bivalent anti-VEGF/ANG2 antibody is characterized in comprising a) as heavy chain of the first full length antibody the amino acid sequence of SEQ ID NO: 17, and as light chain of the first full length antibody the amino acid sequence of SEQ ID NO: 18, and b) as modified heavy chain of the second full length antibody the amino acid sequence of SEQ ID NO: 19, and as modified light chain of the second full length antibody the amino acid sequence of SEQ ID NO: 20.

In one embodiment such bispecific, bivalent anti-VEGF/ANG2 antibody is characterized in comprising the amino acid sequences of SEQ ID NO: 17, of SEQ ID NO: 18, of SEQ ID NO: 19, and of SEQ ID NO: 20. In one preferred embodiment the bispecific, bivalent anti-VEGF/ANG2 antibody is faricimab.

Accordingly, one embodiment of the invention is a bispecific, bivalent antibody comprising a first antigen-binding site that specifically binds to human VEGF and a second antigen-binding site that specifically binds to human ANG-2, characterized in comprising the amino acid sequences of SEQ ID NO: 17, of SEQ ID NO: 18, of SEQ ID NO: 19, and of SEQ ID NO: 20. In one preferred embodiment the bispecific, bivalent anti-VEGF/ANG2 antibody is faricimab.

In on embodiment the CH3 domains of the bispecific, bivalent antibody according to the invention is altered by the "knob-into-holes" technology which is described in detail with several examples in e.g. WO 96/027011, Ridgway J. B., et al., Protein Eng 9 (1996) 617-621; and Merchant, A. M., et al., Nat Biotechnol 16 (1998) 677-681. In this method the interaction surfaces of the two CH3 domains are altered to increase the heterodimerisation of both heavy chains containing these two CH3 domains. Each of the two CH3 domains (of the two heavy chains) can be the "knob", while the other is the "hole". The introduction of a disulfide bridge stabilizes the heterodimers (Merchant, A. M, et al., Nature Biotech 16 (1998) 677-681; Atwell, S., et al. J. Mol. Biol. 270 (1997) 26-35) and increases the yield.

In a preferred aspect of the invention the bispecific anti-VEGF/ANG2 antibodies according to the invention are characterized in that the CH3 domain of one heavy chain and the CH3 domain of the other heavy chain each meet at an interface which comprises an original interface between the antibody CH3 domains;

wherein said interface is altered to promote the formation of the bispecific antibody, wherein the alteration is characterized in that:

a) the CH3 domain of one heavy chain is altered, so that within the original interface the CH3 domain of one heavy chain that meets the original interface of the CH3 domain of the other heavy chain within the bispecific antibody, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and b) the CH3 domain of the other heavy chain is altered, so that within the original interface of the second CH3 domain that meets the original interface of the first CH3 domain within the bispecific antibody an amino acid residue is replaced with an amino acid residue having a smaller side chain volume, thereby generating a cavity within the interface of the second CH3 domain within which a protuberance within the interface of the first CH3 domain is positionable.

Thus the bispecific anti-VEGF/ANG2 antibodies for use described herein are preferably characterized in that the CH3 domain of the heavy chain of the full length antibody of a) and the CH3 domain of the heavy chain of the full length antibody of b) each meet at an interface which comprises an alteration in the original interface between the antibody CH3 domains;

wherein i) in the CH3 domain of one heavy chain an amino acid residue is replaced with an amino acid residue having a larger side chain volume, thereby generating a protuberance within the interface of the CH3 domain of one heavy chain which is positionable in a cavity within the interface of the CH3 domain of the other heavy chain and wherein ii) in the CH3 domain of the other heavy chain an amino acid residue is replaced with an amino acid residue having a smaller side chain volume, thereby generating a cavity within the interface of the second CH3 domain within which a protuberance within the interface of the first CH3 domain is positionable.

Preferably said amino acid residue having a larger side chain volume is selected from the group consisting of arginine (R), phenylalanine (F), tyrosine (Y), tryptophan (W).

Preferably said amino acid residue having a smaller side chain volume is selected from the group consisting of alanine (A), serine(S), threonine (T), valine (V).

In one aspect of the invention both CH3 domains are further altered by the introduction of cysteine (C) as amino acid in the corresponding positions of each CH3 domain such that a disulfide bridge between both CH3 domains can be formed.

In one embodiment, the bispecific antibody comprises a T366W mutation in the CH3 domain of the "knobs chain" and T366S, L368A, Y407V mutations in the CH3 domain of the "hole chain". An additional interchain disulfide bridge between the CH3 domains can also be used (Merchant, A. M, et al., Nature Biotech 16 (1998) 677-681) e.g. by introducing a S354C mutation into one CH3 domain and a Y349C mutation into the other CH3 domain.

In another preferred embodiment the bispecific antibody comprises S354C and T366W mutations in one of the two CH3 domains and Y349C, T366S, L368A, Y407V mutations in the other of the two CH3 domains In a another preferred embodiment the bispecific antibody comprises Y349C, T366W mutations in one of the two CH3 domains and S354C, T366S, L368A, Y407V mutations in the other of the two CH3 domains (the additional Y349C or S354C mutation in one CH3 domain and the additional S354C or Y349C mutation in the other CH3 domain forming a inter-chain disulfide bridge) (numbering always according to EU index of Kabat (Kabat, E. A., et al., Sequences of Proteins of Immunological Interest, 5th ed., Public Health Service, National Institutes of Health, Bethesda, MD (1991)).

Other techniques for CH3-modifications to enforce the heterodimerization are contemplated as alternatives of the invention and described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954 and WO 2013/096291.

In one embodiment the heterodimerization approach described in EP 1 870 459A1 is used alternatively. This approach is based on the introduction of substitutions/mutations of charged amino acids with the opposite charge at specific amino acid positions of the in the CH3/CH3 domain interface between both heavy chains. One preferred embodiment for said multispecific antibodies are amino acid R409D and K370E mutations in the CH3 domain of one heavy chain and amino acid D399K and E357K mutations in the CH3 domain of the other heavy chain of the multispecific antibody (numberings according to Kabat EU index).

In another embodiment said multispecific antibody comprises an amino acid T366W mutation in the CH3 domain of the "knobs chain" and amino acid T366S, L368A and Y407V mutations in the CH3 domain of the "hole chain"; and additionally comprises amino acid R409D and K370E mutations in the CH3 domain of the "knobs chain" and amino acid D399K and E357K mutations in the CH3 domain of the "hole chain".

In one embodiment the heterodimerization approach described in WO2013/157953 is used alternatively. In one embodiment the CH3 domain of one heavy chain comprises an amino acid T366K mutation and the CH3 domain of the other heavy chain comprises an amino acid L351D mutation. In a further embodiment the CH3 domain of the one heavy chain further comprises an amino acid L351K mutation. In a further embodiment the CH3 domain of the other heavy chain further comprises an amino acid mutation selected from Y349E, Y349D and L368E (in one embodiment L368E).

In one embodiment the heterodimerization approach described in WO2012/058768 is used alternatively. In one embodiment the CH3 domain of one heavy chain comprises amino acid L351Y and Y407A mutations and the CH3 domain of the other heavy chain comprises amino acid T366A and K409F mutations. In a further embodiment the CH3 domain of the other heavy chain further comprises an amino acid mutation at position T411, D399, S400, F405, N390 or K392. In one embodiment said amino acid mutation is selected from the group consisting of a) T411N, T411R, T411Q, T411K, T411D, T411E and T411W, b) D399R, D399W, D399Y and D399K, c) S400E, S400D, S400R and S400K, d) F405I, F405M, F405T, F405S, F405V and F405W, e) N390R, N390K and N390D, f) K392V, K392M, K392R, K392L, K392F and K392E.

In a further embodiment the CH3 domain of one heavy chain comprises amino acid L351Y and Y407A mutations and the CH3 domain of the other heavy chain comprises amino acid T366V and K409F mutations. In a further embodiment the CH3 domain of one heavy chain comprises an amino acid Y407A mutation and the CH3 domain of the other heavy chain comprises amino acid T366A and K409F mutations. In a further embodiment the CH3 domain of the other heavy chain further comprises amino acid K392E, T411E, D399R and S400R mutations.

In one embodiment the heterodimerization approach described in WO2011/143545 is used alternatively. In one embodiment the amino acid modification according to WO2011/143545 is introduced in the CH3 domain of the heavy chain at a position selected from the group consisting of 368 and 409.

In one embodiment the heterodimerization approach described in WO2011/090762 which also uses the knob-into-hole technology described above is used alternatively. In one embodiment the CH3 domain of one heavy chain comprises an amino acid T366W mutation and the CH3 domain of the other heavy chain comprises an amino acid Y407A mutation. In one embodiment the CH3 domain of one heavy chain comprises an amino acid T366Y mutation and the CH3 domain of the other heavy chain comprises an amino acid Y407T mutation.

In one embodiment the multispecific antibody is of IgG2 isotype and the heterodimerization approach described in WO2010/129304 is used alternatively.

In one embodiment the heterodimerization approach described in WO2009/089004 is used alternatively. In one embodiment the CH3 domain of one heavy chain comprises an amino acid substitution of K392 or N392 with a negatively-charged amino acid (in one embodiment glutamic acid (E) or aspartic acid (D); in a further embodiment a K392D or N392D mutation) and the CH3 domain of the other heavy chain comprises an amino acid substitution of D399, E356, D356, or E357 with a positively-charged amino acid (in one embodiment Lysine (K) or arginine (R), in a further embodiment a D399K, E356K, D356K or E357K substitution; and in an even further embodiment a D399K or E356K mutation). In a further embodiment the CH3 domain of the one heavy chain further comprises an amino acid substitution of K409 or R409 with a negatively-charged amino acid (in one embodiment glutamic acid (E) or aspartic acid (D); in a further embodiment a K409D or R409D mutation). In a further embodiment the CH3 domain of the one heavy chain further or alternatively comprises an amino acid substitution of K439 and/or K370 with a negatively-charged amino acid (in one embodiment glutamic acid (E) or aspartic acid (D)).

In one embodiment the heterodimerization approach described in WO2007/147901 is used alternatively. In one embodiment the CH3 domain of one heavy chain comprises amino acid K253E, D282K and K322D mutations and the CH3 domain of the other heavy chain comprises amino acid D239K, E240K and K292D mutations.

In one embodiment the heterodimerization approach described in WO2007/110205 is used alternatively.

In one embodiment the bispecific antibody which binds to human vascular endothelial growth factor (VEGF) and to human angiopoietin-2 (ANG-2) is a bispecific anti-VEGF/ANG2 antibody comprising a first antigen-binding site that specifically binds to human VEGF and a second antigen-binding site that specifically binds to human ANG-2, wherein
  i) said first antigen-binding site specifically binding to VEGF comprises in the heavy chain variable domain a CDR3H region of SEQ ID NO: 1, a CDR2H region of SEQ ID NO: 2, and a CDR1H region of SEQ ID NO:3, and in the light chain variable domain a CDR3L region of SEQ ID NO: 4, a CDR2L region of SEQ ID NO:5, and a CDR1L region of SEQ ID NO: 6; and
  ii) said second antigen-binding site specifically binding to ANG-2 comprises in the heavy chain variable domain a CDR3H region of SEQ ID NO: 9, a CDR2H region of, SEQ ID NO: 10, and a CDR1H region of SEQ ID NO: 11, and in the light chain variable domain a CDR3L region of SEQ ID NO: 12, a CDR2L region of SEQ ID NO: 13, and a CDR1L region of SEQ ID NO: 14, and wherein
  iii) the bispecific antibody comprises a constant heavy chain region of human IgG1 subclass comprising the mutations I253A, H310A, and H435A and the mutations L234A, L235A and P329G (numberings according to EU Index of Kabat; and wherein
  iv) in the constant heavy chain region a T366W mutation is comprised in one CH3 domain and T366S, L368A, Y407V mutations are comprised the other CH3 domain (numberings according to EU Index of Kabat).

In one embodiment the bispecific antibody which binds to human vascular endothelial growth factor (VEGF) and to human angiopoietin-2 (ANG-2) is a bispecific anti-VEGF/ANG2 antibody comprising a first antigen-binding site that specifically binds to human VEGF and a second antigen-binding site that specifically binds to human ANG-2, wherein
  i) said first antigen-binding site specifically binding to VEGF comprises in the heavy chain variable domain a CDR3H region of SEQ ID NO: 1, a CDR2H region of SEQ ID NO: 2, and a CDR1H region of SEQ ID NO:3, and in the light chain variable domain a CDR3L region of SEQ ID NO: 4, a CDR2L region of SEQ ID NO:5, and a CDR1L region of SEQ ID NO: 6; and
  ii) said second antigen-binding site specifically binding to ANG-2 comprises in the heavy chain variable domain a CDR3H region of SEQ ID NO: 9, a CDR2H region of, SEQ ID NO: 10, and a CDR1H region of SEQ ID NO: 11, and in the light chain variable domain a CDR3L region of SEQ ID NO: 12, a CDR2L region of SEQ ID NO: 13, and a CDR1L region of SEQ ID NO: 14, and wherein
  iii) the bispecific antibody comprises a constant heavy chain region of human IgG1 subclass comprising the mutations I253A, H310A, and H435A and the mutations L234A, L235A and P329G (numberings according to EU Index of Kabat; and wherein
  iv) in the constant heavy chain region a S354C and T366W mutations are comprised in one CH3 domain and Y349C, T366S, L368A and Y407V mutations are comprised the other CH3 domain (numberings according to EU Index of Kabat).

In one embodiment such bispecific anti-VEGF/ANG2 antibody is bivalent.

In one embodiment such bispecific anti-VEGF/ANG2 antibody is characterized in that
  i) said first antigen-binding site specifically binding to VEGF comprises as heavy chain variable domain VH an amino acid sequence of SEQ ID NO: 7, and as light chain variable domain VL an amino acid sequence of SEQ ID NO: 8, and
  ii) said second antigen-binding site specifically binding to ANG-2 comprises as heavy chain variable domain VH an amino acid sequence of SEQ ID NO: 15, and as light chain variable domain VL an amino acid sequence of SEQ ID NO: 16.

In one aspect of the invention such bispecific, bivalent antibody according to the invention is characterized in comprising a) the heavy chain and the light chain of a first full length antibody that specifically binds to VEGF;

b) the modified heavy chain and modified light chain of a second full length antibody that specifically binds to ANG-2, wherein the constant domains CL and CH1 are replaced by each other.

The term "VEGF" as used herein refers to human vascular endothelial growth factor (VEGF/VEGF-A,) the 165-amino acid human vascular endothelial cell growth factor (amino acid 27-191 of precursor sequence of human VEGF165: SEQ ID NO: 24; amino acids 1-26 represent the signal peptide), and related 121, 189, and 206 vascular endothelial cell growth factor isoforms, as described by Leung, D. W., et al., Science 246 (1989) 1306-9; Houck et al., Mol. Endocrin. 5 (1991) 1806-1814; Keck, P. J., et al., Science 246 (1989) 1309-12 and Connolly, D. T., et al., J. Biol. Chem. 264 (1989) 20017-24; together with the naturally occurring allelic and processed forms of those growth factors. VEGF is involved in the regulation of normal and abnormal angiogenesis and neovascularization associated with tumors and intraocular disorders (Ferrara, N., et al., Endocr. Rev. 18 (1997) 4-25; Berkman, R. A., et al., J. Clin. Invest. 91 (1993) 153-159; Brown, L. F., et al., Human Pathol. 26 (1995) 86-91; Brown, L. F., et al., Cancer Res. 53 (1993) 4727-4735; Mattern, J., et al., Brit. J. Cancer. 73 (1996) 931-934; and Dvorak, H. F., et al., Am. J. Pathol. 146 (1995) 1029-1039). VEGF is a homodimeric glycoprotein that has been isolated from several sources and includes several isoforms. VEGF shows highly specific mitogenic activity for endothelial cells. A VEGF antagonist/inhibitor inhibits binding of VEGF to its receptor VEGFR. Known VEGF antagonist/inhibitors include bispecific anti-VEGF/ANG2 antibodies as described in WO2014/009465.

The term "ANG-2" as used herein refers to human angiopoietin-2 (ANG-2) (alternatively abbreviated with ANGPT2 or ANG2) (SEQ ID NO: 25) which is described e.g. in Maisonpierre, P. C., et al, Science 277 (1997) 55-60 and Cheung, A. H., et al., Genomics 48 (1998) 389-91. The angiopoietins-1 (SEQ ID NO: 26) and -2 were discovered as ligands for the Ties, a family of tyrosine kinases that is selectively expressed within the vascular endothelium (Yancopoulos, G. D., et al., Nature 407 (2000) 242-48). There are now four definitive members of the angiopoietin family. Angiopoietin-3 and -4 (Ang-3 and Ang-4) may represent widely diverged counterparts of the same gene locus in mouse and man (Kim, I., et al., FEBS Let, 443 (1999) 353-56; Kim, I., et al., J Biol Chem 274 (1999) 26523-28). ANG-1 and ANG-2 were originally identified in tissue culture experiments as agonist and antagonist, respectively (see for ANG-1: Davis, S., et al., Cell 87 (1996) 1161-69; and for ANG-2: Maisonpierre, P. C., et al., Science 277 (1997) 55-60). All of the known angiopoietins bind primarily to its receptor TIE2 (SEQ ID NO: 27), and both Ang-1 and -2 bind to TIE2 with an affinity of 3 nM (Kd) (Maisonpierre, P. C., et al., Science 277 (1997) 55-60). An ANG2 antagonist/inhibitor inhibits binding of ANG2 to its receptor TIE2. Known ANG2 antagonist/inhibitors include bispecific anti-VEGF/ANG2 antibodies as described in WO2014/009465.

An antigen-binding sites of the bispecific antibody of the invention contain six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences.

The antibodies of the invention comprise immunoglobulin constant regions derived from human origin of one or more immunoglobulin classes, wherein such immunoglobulin classes include IgG, IgM, IgA, IgD, and IgE classes and, in the case of IgG and IgA, their subclasses, especially IgG1 and IgG4.

The terms "monoclonal antibody" or "monoclonal antibody composition" as used herein refer to a preparation of antibody molecules of a single amino acid composition.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies.". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. Nos. 5,202,238 and 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germline immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Brueggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole, A., et al. and Boerner, P., et al. are also available for the preparation of human monoclonal antibodies (Cole, A., et al., Monoclonal Antibodies and Cancer Therapy, Liss, A. L., p. 77 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to Clq binding and/or FcR binding, e.g. by "class switching" i.e. change or mutation of Fc parts (e.g. from IgG1 to IgG4 and/or IgG1/IgG4 mutation).

The term "recombinant antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant antibodies have variable and constant regions in a rearranged form. The recombinant antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain (VL), variable domain of a heavy chain (VH) as used herein denotes each of the pair of light and heavy chains which is involved directly in binding the antibody to the antigen. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat, E. A., et al., Sequences of Proteins of Immunological Interest, 5th ed., Public Health Service, National Institutes of Health, Bethesda, MD (1991).

The term "full length antibody" denotes an antibody consisting of two "full length antibody heavy chains" and two "full length antibody light chains". A "full length antibody heavy chain" is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH-CH1-HR-CH2-CH3; and optionally an antibody heavy chain constant domain 4 (CH4) in case of an antibody of the subclass IgE. Preferably the "full length antibody heavy chain" is a polypeptide consisting in N-terminal to C-terminal direction of VH, CH1, HR, CH2 and CH3. A "full length antibody light chain" is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ (lambda). The two full length antibody chains are linked together via inter-polypeptide disulfide bonds between the CL domain and the CH1 domain and between the hinge regions of the full length antibody heavy chains. Examples of typical full length antibodies are natural antibodies like IgG (e.g. IgG1 and IgG2), IgM, IgA, IgD, and IgE. The full length antibodies according to the invention can be from a single species e.g. human, or they can be chimerized or humanized antibodies. The full length antibodies according to the invention comprise two antigen binding sites each formed by a pair of VH and VL, which both specifically bind to the same antigen. The C-terminus of the heavy or light chain of said full length antibody denotes the last amino acid at the C-terminus of said heavy or light chain. The N-terminus of the heavy or light chain of said full length antibody denotes the last amino acid at the N-terminus of said heavy or light chain.

The term "constant region" as used within the current applications denotes the sum of the domains of an antibody other than the variable region. The constant region is not involved directly in binding of an antigen, but exhibits various effector functions. Depending on the amino acid sequence of the constant region of their heavy chains, antibodies are divided in the classes: IgA, IgD, IgE, IgG and IgM, and several of these may be further divided into subclasses, such as IgG1, IgG2, IgG3, and IgG4, IgA1 and IgA2. The heavy chain constant regions that correspond to the different classes of antibodies are called α, δ, ε, γ, and μ, respectively. The light chain constant regions which can be found in all five antibody classes are called κ (kappa) and λ (lambda).

The terms "constant region derived from human origin" or "human constant region" as used in the current application denotes a constant heavy chain region of a human antibody of the subclass IgG1, IgG2, IgG3, or IgG4 and/or a constant light chain kappa or lambda region. Such constant regions are well known in the state of the art and e.g. described by Kabat, E. A., et al., Sequences of Proteins of Immunological Interest, 5th ed., Public Health Service, National Institutes of Health, Bethesda, MD (1991) (see also e.g. Johnson, G., and Wu, T. T., Nucleic Acids Res. 28 (2000) 214-218; Kabat, E. A., et al., Proc. Natl. Acad. Sci. USA 72 (1975) 2785-2788). Within the application for the numbering of positions and mutations the EU numbering system (EU Index) according to Kabat, E. A., et al., Sequences of Proteins of Immunological Interest, 5th ed., Public Health Service, National Institutes of Health, Bethesda, MD (1991) is used and referred to as "numbering according to EU Index of Kabat".

In one embodiment the bispecific antibodies according to the invention have a constant region of human IgG1 subclass (derived from human IgG1 subclass). However, the C-terminal lysine (Lys447), or the C-terminal glycine (Gly446) and the C-terminal lysine (Lys447), of the Fc region may or may not be present.

In one embodiment the bispecific antibody as described herein is of IgG1 isotype/subclass and comprises a constant heavy chain domain of SEQ ID NO: 23 or the constant parts of the heavy chain amino acid sequence of SEQ ID NO: 17 and of the heavy chain amino acid sequence of SEQ ID NO: 18. In one embodiment additionally the C-terminal glycine (Gly446) is present. In one embodiment additionally the C-terminal glycine (Gly446) and the C-terminal lysine (Lys447) is present.

Unless otherwise specified herein, numbering of amino acid residues in the constant region is according to the EU numbering system, also called the EU index of Kabat, as described in Kabat, E. A. et al., Sequences of Proteins of Immunological Interest, 5th ed., Public Health Service, National Institutes of Health, Bethesda, MD (1991), NIH Publication 91-3242.

In one embodiment the bispecific antibody according to the invention is of human IgG1 subclass with mutations L234A (Leu235Ala), L235A (Leu234Ala) and P329G (Pro329Gly). Such antibody has a reduced FcR binding (especially they show no more binding to FcRgammaI, FcRgammaII and FcRgammaIII). This especially useful to reduce potential side effects like e.g. thrombosis (Meyer, T., et al., J. Thromb. Haemost. 7 (2009) 171-81).

While Pro329Ala mutation which was described already removes only two third of the FcgammaRIIIa sandwich interaction, the Pro329Gly in the antibodies according to the invention fully imparts binding of the Fc part to FcgammaRIII. This is especially useful as the binding to FcgammaRIII is involved in ADCC (antibody-dependent cellular toxicity) which leads to cell death, which may be helpful in the treatment of cancer diseases, but which can cause serious side effect in the antibody based treatment of other vascular or immunological diseases. So the antibodies according to the invention of IgG1 subclass with mutations L234A, L235A and P329G and IgG4 subclass with mutations S228P, L235E and P329G are especially useful, as they both show no more binding to FcRgammaI, FcRgammaII and FcRgammaIII.

An "effective amount" of an agent, e.g., a pharmaceutical formulation or bispecific anti-VEGF/ANG2 antibody, refers to an amount effective, at dosages and for periods of time necessary, to achieve the desired therapeutic or prophylactic result.

In one embodiment of the invention the bispecific antibody, medicament or pharmaceutical formulation as described herein is administered via intravitreal application, e.g. via intravitreal injection (is administered "intravitreally"). This can be performed in accordance with standard procedures known in the art. See, e.g., Ritter et al., J. Clin. Invest. 116 (2006) 3266-76; Russelakis-Carneiro et al., Neuropathol. Appl. Neurobiol. 25 (1999) 196-206; and Wray et al., Arch. Neurol. 33 (1976) 183-5.

In some embodiments, therapeutic kits of the invention can contain one or more doses of the bispecific antibody described present in a medicament or pharmaceutical formulation, a suitable device for intravitreal injection of the medicament or pharmaceutical formulation, and an instruction detailing suitable subjects and protocols for carrying out the injection. In these embodiments, the medicament or pharmaceutical formulation are typically administered to the subject in need of treatment via intravitreal injection. This can be performed in accordance with standard procedures known in the art. See, e.g., Ritter et al., J. Clin. Invest. 116 (2006) 3266-76; Russelakis-Carneiro et al., Neuropathol. Appl. Neurobiol. 25 (1999) 196-206; and Wray et al., Arch. Neurol. 33 (1976) 183-5.

Regardless of the route of administration selected, the bispecific antibody as described herein is formulated into pharmaceutically acceptable dosage forms by conventional methods known to those of skill in the art.

Description of the Amino Acid Sequences

| SEQ ID NO: | 1 | heavy chain CDR3H, <VEGF>ranibizumab |
|---|---|---|
| SEQ ID NO: | 2 | heavy chain CDR2H, <VEGF>ranibizumab |
| SEQ ID NO: | 3 | heavy chain CDR1H, <VEGF>ranibizumab |
| SEQ ID NO: | 4 | light chain CDR3L, <VEGF>ranibizumab |
| SEQ ID NO: | 5 | light chain CDR2L, <VEGF>ranibizumab |
| SEQ ID NO: | 6 | light chain CDR1L, <VEGF>ranibizumab |
| SEQ ID NO: | 7 | heavy chain variable domain VH, <VEGF>ranibizumab |
| SEQ ID NO: | 8 | light chain variable domain VL, <VEGF>ranibizumab |
| SEQ ID NO: | 9 | heavy chain CDR3H, <ANG-2> Ang2i_LC10 variant |
| SEQ ID NO: | 10 | heavy chain CDR2H, <ANG-2> Ang2i_LC10 variant |
| SEQ ID NO: | 11 | heavy chain CDR1H, <ANG-2> Ang2i_LC10 variant |
| SEQ ID NO: | 12 | light chain CDR3L, <ANG-2> Ang2i_LC10 variant |
| SEQ ID NO: | 13 | light chain CDR2L, <ANG-2> Ang2i_LC10 variant |
| SEQ ID NO: | 14 | light chain CDR1L, <ANG-2> Ang2i_LC10 variant |
| SEQ ID NO: | 15 | heavy chain variable domain VH, <ANG-2> Ang2i_LC10 variant |
| SEQ ID NO: | 16 | light chain variable domain VL, <ANG-2> Ang2i_LC10 variant |
| SEQ ID NO: | 17 | Heavy chain 1 of <VEGF-ANG-2> CrossMAb IgG1 with AAA mutations and P329G LALA mutations (VEGFang2-0016) |
| SEQ ID NO: | 18 | Heavy chain 2 of <VEGF-ANG-2> CrossMAb IgG1 with AAA mutations and P329G LALA mutations (VEGFang2-0016) |
| SEQ ID NO: | 19 | Light chain 1 of <VEGF-ANG-2> CrossMAb IgG1 with AAA mutations and P329G LALA mutations (VEGFang2-0016) |
| SEQ ID NO: | 20 | Light chain 2 of <VEGF-ANG-2> CrossMAb IgG1 with AAA mutations and P329G LALA mutations (VEGFang2-0016) |
| SEQ ID NO: | 21 | kappa light chain constant region |
| SEQ ID NO: | 22 | lambda light chain constant region |
| SEQ ID NO: | 23 | heavy chain constant region derived from human IgG1 |
| SEQ ID NO: | 24 | Human vascular endothelial growth factor (VEGF); precursor sequence of human VEGF165 |
| SEQ ID NO: | 25 | Human angiopoietin-2 (ANG-2) |
| SEQ ID NO: | 26 | Human angiopoietin-1 (ANG-1) |
| SEQ ID NO: | 27 | Human Tie-2 receptor |

In the Following, Embodiments of the Invention are Listed:

1. A bispecific antibody which binds to human vascular endothelial growth factor (VEGF) and to human angiopoietin-2 (ANG-2), for use in the treatment of an ocular vascular disease, 5 wherein the bispecific antibody is administered (is to be administered) intravitreally every 8 weeks or less frequently (in one embodiment every 9 weeks or less frequently; in one embodiment every 10 weeks or less frequently; in one embodiment every 11 weeks or less frequently; in one embodiment every 12 weeks or less frequently; in one embodiment every 13 weeks or less frequently; in one embodiment every 14 weeks or less frequently; in one embodiment every 15 weeks or less frequently).

2A. A bispecific antibody which binds to human vascular endothelial growth factor (VEGF) and to human angiopoietin-2 (ANG-2), for use in the treatment of a patient suffering from an ocular vascular disease, wherein the patient gains 12 or more letters (in one embodiment 13 or more letters, in one embodiment 14 or more letters, 15 or more letters) of Best Corrected Visual Acuity (BCVA) measured using Early Treatment Diabetic Retinopathy Study (ETDRS) like charts, compared to the patient's BCVA letter score prior to the dosing of the bispecific VEGF/ANG2 antibody.

2B. A bispecific antibody which binds to human vascular endothelial growth factor (VEGF) and to human angiopoietin-2 (ANG-2), for use in the treatment of a patient suffering from an ocular vascular disease, wherein the patient experiences an improvement in vision subsequent to the administration of the bispecific VEGF/ANG2 antibody as measured by gaining 12 or more letters (in one embodiment 13 or more letters, in one embodiment 14 or more letters, 15 or more letters) of Best Corrected Visual Acuity (BCVA) measured using Early Treatment Diabetic Retinopathy Study (ETDRS) like charts, compared to the patient's BCVA letter score prior to the dosing of the bispecific VEGF/ANG2 antibody.

3. The bispecific antibody (for use) according to any one of embodiments 2A to 2B,
wherein the bispecific antibody is administered (is to be administered) intravitreally every 8 weeks or less frequently (in one embodiment every 9 weeks or less frequently; in one embodiment every 10 weeks or less frequently; in one embodiment every 11 weeks or less frequently; in one embodiment every 12 weeks or less frequently; in one embodiment every 13 weeks or less frequently; in one embodiment every 14 weeks or less frequently; in one embodiment every 15 weeks or less frequently).

4. The bispecific antibody (for use) according to any one of embodiments 1 to 3, wherein the gain of letters in the BCVA BCVA/ETDRS is measured at 4 weeks, and/or at 8 weeks, and/or at 12 weeks, and/or at 16 weeks, and/or at 20 weeks, and/or at 24 weeks after treatment start, respectively.

The bispecific antibody (for use) according to any one of embodiments 1 to 3, wherein the gain of letters in the BCVA BCVA/ETDRS is measured at 45 weeks, and/or at 46 weeks, and/or at 47 weeks, and/or at 48 weeks, and/or at 49 weeks, and/or at 50 weeks, and/or at 51 weeks, and/or at 52 weeks, and/or at 53 weeks, and/or at 54 weeks, and/or at 55 weeks, and/or at 56 weeks, and/or at 57 weeks, and/or at 58 weeks, and/or at 59 weeks, and/or at 60 weeks after treatment start, respectively.

6. The bispecific antibody (for use) according to any one of embodiments 1 to 5, wherein the bispecific antibody is used to prolong the time to retreatment and/or to prolong the time to loss of visual acuity (e.g. Best Corrected Visual Acuity (BCVA) BCVA/ETDRS) and, wherein the retreatment is deemed necessary in case of disease activity which is determined as
Central Subfield Thickness (CST) increased by ≥50 μm (in one embodiment using spectral domain optical coherence tomography (SD-OCT)); and/or Best Corrected Visual Acuity (BCVA/ETDRS) decreased by ≥5 letters.

7. The bispecific antibody (for use) according to any one of embodiments 1 to 6 wherein the bispecific antibody is administered following a treatment initiation of 3 to 7 monthly administrations (in one embodiment the treatment initiation includes 3 to 5 monthly administrations, in one embodiment the treatment initiation includes 4 monthly administrations; in one embodiment the treatment initiation includes 5 to 7 monthly administrations, in one embodiment the treatment initiation includes 6 monthly administrations).

8. The bispecific antibody (for use) according to any one of embodiments 1 to 7, wherein the ocular vascular disease is selected from the group of: wet age-related macular degeneration (wet AMD), neovascular AMD, diabetic macular edema (DME), cystoid macular edema (CME), nonproliferative diabetic retinopathy (NPDR), proliferative diabetic retinopathy (PDR), macular edema secondary to central retinal vein occlusion, secondary to hemiretinal vein occlusion or secondary to branch vein occlusion, retinitis, conjunctivitis, uveitis, choroiditis, choroidal neovascularization (CNV) secondary to ocular inflammation including secondary to ocular histoplasmosis or presumed histoplasmosis or choroiditis; myopic choroidal neovascularization (mCNV). And choroidal neovascularization secondary to trauma, retinopathy of prematurity and rubeosis iridis/rubeotic glaucoma.

9. The bispecific antibody (for use) according to any one of embodiments 1 to 7 wherein the ocular vascular disease is diabetic macular edema (DME).

10. The bispecific antibody (for use) according to any one of embodiments 1 to 7, wherein the ocular vascular disease is wet age-related macular degeneration (wet AMD), or neovascular age-related macular degeneration (nAMD).

11. The bispecific antibody (for use) according to any one of embodiments 1 to 10, wherein the bispecific antibody which binds to VEGF and to human ANG-2 is a VEGF antagonist/inhibitor and an ANG2 antagonist/inhibitor or inhibits binding of VEGF to its receptor VEGFR and inhibits binding of ANG2 to its receptor TIE2.

12. The bispecific antibody (for use) according to any one of embodiments 1 to 11, wherein the bispecific antibody is administered every 10 to 12 weeks.

13. The bispecific antibody (for use) according to any one of embodiments 1 to 11, wherein the bispecific antibody is administered every 11 to 13 weeks.

14. The bispecific antibody (for use) according to any one of embodiments 1 to 11 wherein the bispecific antibody is administered every 12 to 14 weeks.

15. The bispecific antibody (for use) according to any one of embodiments 1 to 11 wherein the bispecific antibody is administered every 13 to 15 weeks.

16. The bispecific antibody (for use) according to any one of embodiments 1 to 11 wherein the bispecific antibody is administered every 14 to 16 weeks.

17. The bispecific antibody (for use) according to any one of embodiments 1 to 16, wherein the bispecific antibody which binds to human VEGF and to human ANG2 is a bispecific, bivalent anti-VEGF/ANG2 antibody comprising a first antigen-binding site that specifically binds to human VEGF and a second antigen-binding site that specifically binds to human ANG-2, wherein
i) said first antigen-binding site specifically binding to VEGF comprises in the heavy chain variable domain a CDR3H region of SEQ ID NO: 1, a CDR2H region of SEQ ID NO: 2, and a CDR1H region of SEQ ID NO:3, and in the light chain variable domain a CDR3L region of SEQ ID NO: 4, a CDR2L region of SEQ ID NO:5, and a CDR1L region of SEQ ID NO: 6; and
ii) said second antigen-binding site specifically binding to ANG-2 comprises in the heavy chain variable domain a CDR3H region of SEQ ID NO: 9, a CDR2H region of, SEQ ID NO: 10, and a CDR1H region of SEQ ID NO: 11, and in the light chain variable domain a CDR3L region of SEQ ID NO: 12, a CDR2L region of SEQ ID NO: 13, and a CDR1L region of SEQ ID NO: 14, and wherein iii) the bispecific antibody comprises a constant heavy chain region of human IgG1 subclass comprising the mutations I253A, H310A, and H435A and the mutations L234A, L235A and P329G (numberings according to EU Index of Kabat).

18. The bispecific antibody (for use) according to embodiment 17, wherein i) said first antigen-binding site specifically binding to VEGF comprises as heavy chain variable domain VH an amino acid sequence of SEQ ID NO: 7, and as light chain variable domain VL an amino acid sequence of SEQ ID NO: 8, and ii) said second antigen-binding site specifically binding to ANG-2 comprises as heavy chain variable domain VH an amino acid sequence of SEQ ID NO: 15, and as light chain variable domain VL an amino acid sequence of SEQ ID NO: 16.

19. The bispecific antibody (for use) according to embodiment 18, wherein the bispecific antibody which binds to human VEGF and human ANG2 comprises the amino acid sequences of SEQ ID NO: 17, of SEQ ID NO: 18, of SEQ ID NO: 19, and of SEQ ID NO: 20.

20. The bispecific antibody (for use) according to any one of embodiments 17 to 19, wherein the bispecific antibody is administered in a dose of about 5 to 7 mg (at each treatment).

21. The bispecific antibody (for use) according to any one of embodiments 17 to 19, wherein the bispecific antibody is administered in a dose of about 6 mg (at each treatment) (in one embodiment in a dose of 6 mg+/−10% (at each treatment); (in one embodiment in a dose of 6 mg (at each treatment)))

22. The bispecific antibody (for use) according to any one of embodiments 20 to 21, wherein the bispecific antibody is administered at a concentration of about 30 mg/ml.

23. The bispecific antibody (for use) according to any one of embodiments 20 to 21, wherein the bispecific antibody is administered at a concentration of about 120 mg/ml.

24. The bispecific antibody (for use) according to any one of the preceding embodiments wherein patients suffering from an ocular vascular disease have not been previously treated with anti-VEGF treatment (e.g monotherapy) (are treatment naïve).

25. The bispecific antibody (for use) according to any one of the preceding embodiments wherein patients suffering from an ocular vascular disease have been previously treated with anti-VEGF treatment (e.g monotherapy).

26. The bispecific antibody (for use) according to the preceding embodiments wherein the ocular vascular disease is DME and the treatment of patients suffering from DME includes a fixed every 8th week (Q8W) dosing schedule following treatment initiation (In one embodiment the treatment initiation includes 5 to 7 monthly administrations; in one embodiment the treatment initiation includes 6 monthly administrations).

27. The bispecific antibody (for use) according to the preceding embodiments wherein the ocular vascular disease is DME and the treatment of patients suffering from DME includes a fixed Q12W dosing schedule following treatment initiation (In one embodiment the treatment initiation includes 5 to 7 monthly administrations; in one embodiment the treatment initiation includes 6 monthly administrations).

28. The bispecific antibody (for use) according to embodiment 27 wherein, following the treatment initiation, first one dose cycle of Q8W follows before the fixed Q12W dosing schedule.

29. The bispecific antibody (for use) according to the preceding embodiments wherein the ocular vascular disease is DME and the treatment of patients suffering from DME includes following treatment initiation a dosing schedule that extends the administration interval in stable absence of disease, or shortens the interval if there is disease activity (In one embodiment the treatment initiation includes 3 to 7 monthly administrations; in one embodiment the treatment initiation includes 4 to 6 monthly administrations).

30. The bispecific antibody (for use) according to embodiment 29 wherein such dosing schedule includes that the patient receives Q8W or Q12W or Q16W dosing, dependent on their disease state (in one embodiment Q4W or Q8W or Q12W or Q16W dosing, dependent on their disease state)

31. The bispecific antibody (for use) according to embodiment 29 or 30, wherein the stable absence of disease is determined as Central Subfield Thickness (CST) increased by <50 μm; and/or Best Corrected Visual Acuity (BCVA/ETDRS) decreased by <5 letters and the disease activity is determined as Central Subfield Thickness (CST) increased by ≥50 μm; and/or Best Corrected Visual Acuity (BCVA/ETDRS) decreased by ≥5 letters.

32. The method according to embodiment 29 or 30, wherein the stable absence of disease is determined as Central Subfield Thickness (CST) is below about 300 μm (In one embodiment below 325 μm measured by spectral domain optical coherence tomography (SD-OCT) with a Spectralis™ device; in one embodiment below 315 μm measured by spectral domain optical coherence tomography (SD-OCT) with a Cirrus™ device; in one embodiment below 315 μm measured by spectral domain optical coherence tomography (SD-OCT) with a Topcon™ device; in one embodiment below 295 μm measured by spectral domain optical coherence tomography (SD-OCT) with a Optovue™ device), and the disease activity is determined as Central Subfield Thickness (CST) is above about 300 μm (In one embodiment above 325 μm measured by spectral domain optical coherence tomography (SD-OCT) with a Spectralis™ device; in one embodiment above 315 μm measured by spectral domain optical coherence tomography (SD-OCT) with a Cirrus™ device; in one embodiment above 315 μm measured by spectral domain optical coherence tomography (SD-OCT) with a Topcon™ device; in one embodiment above 295 μm measured by spectral domain optical coherence tomography (SD-OCT) with a Optovue™ device).

33. The bispecific antibody (for use) according to the preceding embodiments wherein the ocular vascular disease is AMD (in one embodiment wet AMD) and the treatment of patients suffering from AMD (in one embodiment wet AMD) includes following treatment initiation (In one embodiment the treatment initiation includes 3 to 7 monthly administrations; in one embodiment the treatment initiation includes 4 to 6 monthly administrations) a dosing schedule that extends the administration interval in stable absence of disease, or shortens the interval if there is disease activity.

34. The bispecific antibody (for use) according to embodiment 33 wherein such dosing schedule includes that the patient receives Q8W or Q12W or Q16W dosing, dependent on their disease state (in one embodiment Q4W or Q8W or Q12W or Q16W dosing, dependent on their disease state).

35. The bispecific antibody (for use) according to embodiment 33 or 34, wherein the stable absence of disease is determined as Central Subfield Thickness (CST) increased by <50 μm; and/or Best Corrected Visual Acuity (BCVA/ETDRS) decreased by <5 letters and the disease activity is determined as Central Subfield Thickness (CST) increased by ≥50 μm; and/or Best Corrected Visual Acuity (BCVA/ETDRS) decreased by ≥5 letters.

36. The bispecific antibody (for use) according to embodiment 33 or 34, wherein the stable absence of disease is determined as Central Subfield Thickness (CST) is below about 300 μm (In one embodiment below 325 μm measured by spectral domain optical coherence tomography (SD-OCT) with a Spectralis™ device; in one embodiment below 315 μm measured by spectral domain optical coherence tomography (SD-OCT) with a Cirrus™ device; in one embodiment below 315 μm measured by spectral domain optical coherence tomography (SD-OCT) with a Topcon™ device; in one embodiment below 295 μm measured by spectral domain optical coherence tomography (SD-OCT) with a Optovue™ device), and the disease activity is determined as Central Subfield Thickness (CST) is above about 300 μm (In one embodiment above 325 μm measured by spectral domain optical coherence tomography (SD-OCT) with a Spectralis™ device; in one embodiment above 315 μm measured by spectral domain optical coherence tomography (SD-OCT) with a Cirrus™ device; in one embodiment above 315 μm measured by spectral domain optical coherence tomography (SD-OCT) with a Topcon™ device; in one embodiment above 295 μm measured by spectral domain optical coherence tomography (SD-OCT) with a Optovue™ device).

In the Following, Embodiments of the Invention are Listed:

1. A method of treating a patient suffering from an ocular vascular disease the method comprising administering to the patient an effective amount of a bispecific antibody which binds to human vascular endothelial growth factor (VEGF) and to human angiopoietin-2 (ANG-2), wherein the bispecific antibody is administered intravitreally every 8 weeks or less frequently (in one embodiment every 9 weeks or less frequently; in one embodiment every 10 weeks or less frequently; in one embodiment every 11 weeks or less frequently; in one embodiment every 12 weeks or less frequently; in one embodiment every 13 weeks or less frequently; in one embodiment every 14 weeks or less frequently; in one embodiment every 15 weeks or less frequently).

2A. A method of treating a patient suffering from an ocular vascular disease the method comprising administering to the patient an effective amount of a bispecific antibody which binds to human vascular endothelial growth factor (VEGF) and to human angiopoietin-2 (ANG-2), wherein the patient gains 12 or more letters (in one embodiment 13 or more letters, in one embodiment 14 or more letters, in one embodiment 15 or more letters) of Best Corrected Visual Acuity (BCVA) measured using Early Treatment Diabetic Retinopathy Study (ETDRS) like charts, compared to the patient's BCVA letter score prior to the dosing of the bispecific VEGF/ANG2 antibody.

2B. A method of treating a patient suffering from a ocular vascular disease the method comprising administering to the patient an effective amount of a bispecific antibody which binds to human vascular endothelial growth factor (VEGF) and to human angiopoietin-2 (ANG-2), wherein the patient experiences an improvement in vision subsequent to the administration of the bispecific VEGF/ANG2 antibody as measured by gaining 12 or more letters (in one embodiment 13 or more letters, in one embodiment 14 or more letters, in one embodiment 15 or more letters) of Best Corrected Visual Acuity (BCVA) measured using Early Treatment Diabetic Retinopathy Study (ETDRS) like charts, compared to the patient's BCVA letter score prior to the dosing of the bispecific VEGF/ANG2 antibody.

3. The method according to any one of embodiments 2A to 2B, wherein the bispecific antibody is administered (is to be administered) intravitreally every 8 weeks or less frequently (in one embodiment every 9 weeks or less frequently; in one embodiment every 10 weeks or less frequently; in one embodiment every 11 weeks or less frequently; in one embodiment every 12 weeks or less frequently; in one embodiment every 13 weeks or less frequently; in one embodiment every 14 weeks or less frequently; in one embodiment every 15 weeks or less frequently).

4. The method according to any one of embodiments 1 to 3, wherein the gain of letters in the BCVA/ETDRS letter score is measured at 4 weeks, and/or at 8 weeks, and/or at 12 weeks, and/or at 16 weeks, and/or at 20 weeks, and/or at 24 weeks after treatment start, respectively.

5. The method according to any one of embodiments 1 to 3, wherein the gain of letters in the BCVA/ETDRS letter score is measured at 45 weeks, and/or at 46 weeks, and/or at 47 weeks, and/or at 48 weeks, and/or at 49 weeks, and/or at 50 weeks, and/or at 51 weeks, and/or at 52 weeks, and/or at 53 weeks, and/or at 54 weeks, and/or at 55 weeks, and/or at 56 weeks, and/or at 57 weeks, and/or at 58 weeks, and/or at 59 weeks, and/or at 60 weeks after treatment start, respectively.

6. The method according to any one of embodiments 1 to 5, wherein the bispecific antibody is used to prolong the time to retreatment and/or to prolong the time to loss of visual acuity and, wherein the retreatment with the bispecific antibody is administered in case of a disease activity which is determined as Central Subfield Thickness (CST) increase by ≥50 μm (in one embodiment using spectral domain optical coherence tomography (SD-OCT)); and/or Best Corrected Visual Acuity (BCVA/ETDRS) decrease by ≥5 letters.

7. The method according to any one of embodiments 1 to 6, wherein the bispecific antibody is administered following a treatment initiation of 3 to 7 monthly administrations (in one embodiment the treatment initiation includes 3 to 5 monthly administrations, in one embodiment the treatment initiation includes 4 monthly administrations in one embodiment the treatment initiation includes 5 to 7 monthly administrations, in one embodiment the treatment initiation includes 6 monthly administrations).

8. The method according to any one of embodiments 1 to 7, wherein the ocular vascular disease is selected from the group of: wet age-related macular degeneration (wet AMD), neovascular AMD, diabetic macular edema (DME), cystoid macular edema (CME), non-proliferative diabetic retinopathy (NPDR), proliferative diabetic retinopathy (PDR), macular edema secondary to central retinal vein occlusion, secondary to hemiretinal vein occlusion or secondary to branch vein occlusion, retinitis, conjunctivitis, uveitis, choroiditis, choroidal neovascularization (CNV) secondary to ocular inflammation including secondary to ocular histoplasmosis or presumed histoplasmosis or choroiditis; myopic choroidal neovascularization (mCNV). And choroidal neovascularization secondary to trauma, retinopathy of prematurity and rubeosis iridis/rubeotic glaucoma.

9. The method according to any one of embodiments 1 to 7, wherein the ocular vascular disease is diabetic macular edema (DME).

10. The method according to any one of embodiments 1 to 7, wherein the ocular vascular disease is wet age-related macular degeneration (wet AMD), or neovascular age-related macular degeneration (nAMD).

11. The method according to any one of embodiments 1 to 10, wherein the a bispecific antibody which binds to VEGF and to human ANG-2 is a VEGF antagonist/inhibitor and an ANG2 antagonist/inhibitor or inhibits binding of VEGF to its receptor VEGFR and inhibits binding of ANG2 to its receptor TIE2.

12. The method according to any one of embodiments 1 to 11, wherein the bispecific antibody is administered every 10 to 12 weeks.

13. The method according to any one of embodiments 1 to 11, wherein the bispecific antibody is administered every 11 to 13 weeks 14. The method according to any one of embodiments 1 to 11, wherein the bispecific antibody is administered every 12 to 14 weeks.

15. The method according to any one of embodiments 1 to 11, wherein the bispecific antibody is administered every 13 to 15 weeks.

16. The method according to any one of embodiments 1 to 11, wherein the bispecific antibody is administered every 14 to 16 weeks.

17. The method according to any one of embodiments 1 to 16, wherein the bispecific antibody which binds to human VEGF and to human ANG2 is a bispecific, bivalent anti-VEGF/ANG2 antibody comprising a first antigen-binding site that specifically binds to human VEGF and a second antigen-binding site that specifically binds to human ANG-2, wherein i) said first antigen-binding site specifically binding to VEGF comprises in the heavy chain variable domain a CDR3H region of SEQ ID NO: 1, a CDR2H region of SEQ ID NO: 2, and a CDR1H region of SEQ ID NO:3, and in the light chain variable domain a CDR3L region of SEQ ID NO: 4, a CDR2L region of SEQ ID NO:5, and a CDR1L region of SEQ ID NO: 6; and ii) said second antigen-binding site specifically binding to ANG-2 comprises in the heavy chain variable domain a CDR3H region of SEQ ID NO: 9, a CDR2H region of, SEQ ID NO: 10, and a CDR1H region of SEQ ID NO: 11, and in the light chain variable domain a CDR3L region of SEQ ID NO: 12, a CDR2L region of SEQ ID NO: 13, and a CDR1L region of SEQ ID NO: 14, and wherein iii) the bispecific antibody comprises a constant heavy chain region of human IgG1 subclass comprising the mutations I253A, H310A, and H435A and the mutations L234A, L235A and P329G (numberings according to EU Index of Kabat).

18. The method according to embodiment 17, wherein i) said first antigen-binding site specifically binding to VEGF comprises as heavy chain variable domain VH an amino acid sequence of SEQ ID NO: 7, and as light chain variable domain VL an amino acid sequence of SEQ ID NO: 8, and ii) said second antigen-binding site specifically binding to ANG-2 comprises as heavy chain variable domain VH an amino acid sequence of SEQ ID NO: 15, and as light chain variable domain VL an amino acid sequence of SEQ ID NO: 16.

19. The method according to embodiment 18, wherein the bispecific antibody which binds to human VEGF and human ANG2 comprises the amino acid sequences of SEQ ID NO: 17, of SEQ ID NO: 18, of SEQ ID NO: 19, and of SEQ ID NO: 20.

20. The method according to any one of embodiments 17 to 19, wherein the bispecific antibody is administered in a dose of about 5 to 7 mg (at each treatment).

21. The method according to any one of embodiments 17 to 19, wherein the bispecific antibody is administered in a dose of about 6 mg (at each treatment) (in one embodiment in a dose of 6 mg+/−10% (at each treatment) (in one embodiment in a dose of 6 mg (at each treatment))).

22. The method according to any one of embodiments 20 to 21, wherein the bispecific antibody is administered at a concentration of about 30 mg/ml.

23. The method according to any one of embodiments 20 to 21, wherein the bispecific antibody is administered at a concentration of about 120 mg/ml.

24. The method according to any one of the preceding embodiments wherein patients suffering from an ocular vascular disease have not been previously treated with anti-VEGF treatment (e.g monotherapy) (are treatment naïve).

25. The method according to any one of the preceding embodiments wherein patients suffering from an ocular vascular disease have been previously treated with anti-VEGF treatment (e.g monotherapy).

26. The method according to the preceding embodiments wherein the ocular vascular disease is DME and the treatment of patients suffering from DME includes a fixed every 8th week (Q8W) dosing schedule following treatment initiation (In one embodiment the treatment initiation includes 5 to 7 monthly administrations; in one embodiment the treatment initiation includes 6 monthly administrations).

27. The method according to the preceding embodiments wherein the ocular vascular disease is DME and the treatment of patients suffering from DME includes a fixed Q12W dosing schedule following treatment initiation (In one embodiment the treatment initiation includes 5 to 7 monthly administrations; in one embodiment the treatment initiation includes 6 monthly administrations).

28. The method according to embodiment 27 wherein, following the treatment initiation, first one dose cycle of Q8W follows before the fixed Q12W dosing schedule.

29. The method according to the preceding embodiments wherein the ocular vascular disease is DME and the treatment of patients suffering from DME includes following treatment initiation a dosing schedule that extends the administration interval in stable absence of disease, or shortens the interval if there is disease activity (In one embodiment the treatment initiation includes 3 to 7 monthly administrations; in one embodiment the treatment initiation includes 4 to 6 monthly administrations).

30. The method according to embodiment 29 wherein such dosing schedule includes that the patient receives Q8W or Q12W or Q16W dosing, dependent on their disease state (in one embodiment Q4W or Q8W or Q12W or Q16W dosing, dependent on their disease state).

31. The method according to embodiment 28 or 29, wherein the stable absence of disease is determined as
Central Subfield Thickness (CST) increased by <50 μm; and/or
Best Corrected Visual Acuity (BCVA/ETDRS) decreased by <5 letters
and the disease activity is determined as
Central Subfield Thickness (CST) increased by ≥50 μm; and/or
Best Corrected Visual Acuity (BCVA/ETDRS) decreased by ≥5 letters.

32. The method according to embodiment 28 or 29, wherein the stable absence of disease is determined as
Central Subfield Thickness (CST) is below about 300 μm (In one embodiment below 325 μm measured by spectral domain optical coherence tomography (SD-OCT) with a Spectralis™ device; in one embodiment below 315 μm measured by spectral domain optical coherence tomography (SD-OCT) with a Cirrus™ device; in one embodiment below 315 μm measured by spectral domain optical coherence tomography (SD-OCT) with a Topcon™ device; in one embodiment below 295 μm measured by spectral domain optical coherence tomography (SD-OCT) with a Optovue™ device),
and the disease activity is determined as
Central Subfield Thickness (CST) is above about 300 μm (In one embodiment above 325 μm measured by spectral domain optical coherence tomography (SD-OCT) with a Spectralis™ device; in one embodiment above 315 μm measured by spectral domain optical coherence tomography (SD-OCT) with a Cirrus™ device; in one embodiment above 315 μm measured by spectral domain optical coherence tomography (SD-OCT) with a Topcon™ device; in one embodiment above 295 μm measured by spectral domain optical coherence tomography (SD-OCT) with a Optovue™ device).

33. The method according to the preceding embodiments wherein the treatment of patients suffering from AMD (in one embodiment wet AMD) includes following treatment initiation (In one embodiment the treatment initiation includes 3 to 7 monthly administrations; in one embodiment the treatment initiation includes 4 to 6 monthly administrations) a dosing schedule that extends the administration interval in stable absence of disease, or shortens the interval if there is disease activity 34. The method according to embodiment 33 wherein such dosing schedule includes that the patient receives Q8W or Q12W or Q16W dosing, dependent on their disease state (in one embodiment Q4W or Q8W or Q12W or Q16W dosing, dependent on their disease state).

35. The method according to embodiment 33 or 34, wherein the stable absence of disease is determined as
Central Subfield Thickness (CST) increased by <50 μm; and/or
Best Corrected Visual Acuity (BCVA/ETDRS) decreased by <5 letters
and the disease activity is determined as
Central Subfield Thickness (CST) increased by ≥50 μm; and/or
Best Corrected Visual Acuity (BCVA/ETDRS) decreased by ≥5 letters.

36. The method according to embodiment 33 or 34, wherein the stable absence of disease is determined as
Central Subfield Thickness (CST) is below about 300 μm (In one embodiment below 325 μm measured by spectral domain optical coherence tomography (SD-OCT) with a Spectralis™ device; in one embodiment below 315 μm measured by spectral domain optical coherence tomography (SD-OCT) with a Cirrus™ device; in one embodiment below 315 μm measured by spectral domain optical coherence tomography (SD-OCT) with a Topcon™ device; in one embodiment below 295 μm measured by spectral domain optical coherence tomography (SD-OCT) with a Optovue™ device),
and the disease activity is determined as
Central Subfield Thickness (CST) is above about 300 μm (In one embodiment above 325 μm measured by spectral domain optical coherence tomography (SD-OCT) with a Spectralis™ device; in one embodiment above 315 μm measured by spectral domain optical coherence tomography (SD-OCT) with a Cirrus™ device; in one embodiment above 315 μm measured by spectral domain optical coherence tomography (SD-OCT) with a Topcon™ device; in one embodiment above 295 μm measured by spectral domain optical coherence tomography (SD-OCT) with a Optovue™ device).

EXAMPLES

Treatment of Patient Suffering from Vascular Eye Diseases with a Bispecific Antibody that Binds to Human VEGE and Human ANG2

Example 1A: Efficacy and Durability of Treatment of Patients Suffering from Diabetic Macular Edema (DME)

Objectives

Primary Objective

The Primary Objective of this Study were:
To evaluate the efficacy of the bispecific antibody that binds to human VEGF and human ANG2 comprising the amino acid sequences of SEQ ID NO: 17, of SEQ ID NO: 18, of SEQ ID NO: 19, and of SEQ ID NO: 20 (this antibody VEGFang2-0016 and its production is also described in detail in WO2014/009465 which is incorporated by reference) compared with an active comparator in treatment naïve patients with center-involving diabetic macular edema (CI-DME). Designations of this bispecific anti-VEGF/ANG2 antibody herein are RO6867461 or RG7716 or VEGFang2-0016, or faricimab. Vials of sterile, colorless to brownish, preservative-free solution of RO6867461 for IVT administration of either 1.5 mg or 6 mg dose every 4 weeks were used. The concentration of the bispecific antibody was about 120 mg/ml.

Secondary Objectives

The Secondary Objectives for this Study were as Follows:
To investigate pharmacodynamics and anatomical outcomes informing on the mechanism of action of RO6867461
To investigate the formation of plasma anti RO6867461 antibodies
To explore the duration of effect of RO6867461

Exploratory Objectives

The Exploratory Objectives for this Study were as Follows:
To explore the predictive effect of previous IVT anti-VEGF treatment on efficacy of RO6867461

To evaluate the efficacy and safety of RO6867461 compared with the active comparator in patients with CI DME with previous IVT anti-VEGF treatment.

To evaluate RO6867461 effects on plasma levels of markers of angiogenesis and inflammation To investigate RO6867461 concentration and, if sample volume allows, biomarkers of angiogenesis and inflammation in aqueous humor samples (optional) and vitreous (optional)

To evaluate improvement in diabetic retinopathy (DR) severity score

Study Design

This was a multiple-center, multiple-dose, randomized, active comparator-controlled, double masked, three parallel group, 36-week study in patients with CI-DME.

The three groups of this study were as follows:

Arm A: 0.3 mg ranibizumab IVT

Arm B: 1.5 mg RO6867461 IVT

Arm C: 6 mg RO6867461 IVT

Only one eye was selected as the study eye. Where both eyes met all eligibility criteria, the eye with the worse BCVA was defined as the study eye. Where both eyes met all eligibility criteria and have the same BCVA letter score at Day 1, study eye selection was at the investigator's discretion.

Number of Patients

Up to 210 patients were randomized.

Approximately 150 treatment-naïve patients and approximately 60 patients who have been previously treated with IVT anti-VEGF were enrolled in the study.

Approximately 50 treatment-naïve patients were randomized on each arm (1:1:1 randomization scheme) and approximately 30 patients previously treated with IVT anti-VEGF were randomized into arms A and C.

Target Population

Male and female patients of ≥18 years of age with CI-DME.

Inclusion/Exclusion Criteria

Inclusion Criteria

Patients must have met the following criteria for study entry:

Ocular Criteria for Study Eye:

Macular edema associated with DR defined as macular thickening by spectral domain optical coherence tomography (SD-OCT) involving the center of the macula: central subfield thickness (CST) of ≥325 µm with Spectralis™ (Heidelberg) at screening (where Spectralis™ is not available, the following devices and CST thresholds were acceptable: CST≥315 µm for Cirrus™, CST≥315 µm for Topcon, CST≥295 µm for Optovue™).

Decreased visual acuity attributable primarily to DME, with best corrected visual acuity (BCVA) letter score of 73-24 letters (inclusive) on Early Treatment Diabetic Retinopathy Study (ETDRS)-like charts (20/40-20/320 Snellen equivalent) on Day 1.

Clear ocular media and adequate pupillary dilatation to allow acquisition of good quality retinal images to confirm diagnosis General Criteria:

Diagnosis of diabetes mellitus (DM; Type 1 or Type 2), as defined by the World Health Organization and/or American Diabetes Association Able and willing to provide written informed consent and to comply with the study protocol according to International Conference on Harmonisation (ICH) and local regulations.

Alternatively, a legally authorized representative must be able to consent for the patient according to ICH and local regulations.

Age≥18 Years

For women who were not postmenopausal (i.e. ≥12 months of non-therapy-induced amenorrhea, confirmed by FSH, if not on hormone replacement) or surgically sterile (absence of ovaries and/or uterus) agreement to remain abstinent or use combined contraceptive methods that result in a failure rate of <1% per year during the treatment period and at least through 4 weeks after last dose.

Abstinence is only acceptable if it is in line with the preferred and usual lifestyle of the patient. Periodic abstinence (e.g., calendar, ovulation, symptothermal, or postovulation methods) and withdrawal were not acceptable methods of contraception;

Examples of contraceptive methods with an expected failure rate of <1% per year include male sterilization, hormonal implants, proper use of combined oral or injected hormonal contraceptives, and certain intrauterine devices. Alternatively, two methods (e.g., two barrier methods such as a condom and a cervical cap) may be combined to achieve a failure rate of <1% per year, barrier methods must always be supplemented with the use of a spermicide.

For men: agreement to use a barrier method of contraception during the treatment period for at least 4 weeks after the last dose of study drug Patients must be willing not to participate in any other clinical trial including an investigational medical product (IMP) or device up to completion of the current study.

Exclusion Criteria

Patients who meet any of the following criteria were excluded from study entry:

Ocular Criteria for Study Eye:

Any signs of high-risk PDR defined as:

any vitreous or pre-retinal hemorrhage

NVE≥½ disc area within an area equivalent to the standard mydriatic ETDRS 7-field on clinical examination NVD≥⅓ disc area on clinical examination Any IVT anti-VEGF treatment within 3 months prior to Day 1

Any panretinal photocoagulation (PRP) treatment prior to Day 1

Any macular laser photocoagulation within 3 months prior to Day 1

History of Vitreoretinal Surgery

Any IVT or periocular corticosteroid treatment within 3 months prior to Day 1. Any history of Iluvien® or Ozurdex® implants prior to Day 1 will not be permitted Any cataract surgery or treatment for complications of cataract surgery with steroids within 3 months prior to Day 1

History of Incisional Glaucoma Surgery

Uncontrolled glaucoma (e.g., progressive loss of visual fields or defined as intraocular pressure [IOP]≥25 mmHg despite treatment with anti-glaucoma medication)

Concurrent Ocular Conditions in the Study Eye:

History of Rubeosis

Any current or history of ocular disease other than DME that may confound assessment of the macula or affect central vision (e.g., age-related macular degeneration, retinal vein occlusion, uveitis, angioid streaks, histoplasmosis, active or inactive cytomegalovirus, pathological myopia, retinal detachment, macular traction, macular hole, significant cataract)

Any current ocular condition for which, in the opinion of the investigator, visual acuity loss would not improve from resolution of macular edema (e.g., foveal atrophy, pigment abnormalities, dense sub-foveal hard exudates, non-retinal condition)

Any active ocular infection on Day 1

Any active intraocular inflammation (grade trace or above) on Day 1

Characteristics for Fellow Eye:

Any anti-VEGF treatment within 7 days prior to Day 1

Any retinal condition that, in the opinion of the investigator, might require anti-VEGF treatment within 7 days from Day 1

General Criteria:

Any systemic anti-VEGF within 6 months prior to Day 1

Any major illness or major surgical procedure within 1 month prior to Day 1

Any febrile illness within 1 week prior to Day 1

Any stroke or myocardial infarction within 12 months prior to Day 1

Uncontrolled blood pressure (BP; defined as systolic>180 mmHg and/or diastolic>100 mmHg while patient at rest). If a patient's initial reading exceeds these values, a second reading may be taken either 30 or more minutes later on the same day or on another day during the screening period. If the patient's BP needs to be controlled by antihypertensive medication, the patient should be taking the same medication continuously for at least 1 month prior to Day 1.

Patients with glycosylated hemoglobin HbA1c>12% at screening

Untreated diabetes mellitus or initiation of oral anti-diabetic medication or insulin within 4 months prior to Day 1 or anticipated change of anti-diabetic medications within the duration of the study Renal failure requiring renal transplant, hemodialysis, or peritoneal dialysis within 6 months prior to Day 1 or anticipated to require hemodialysis or peritoneal dialysis at any time during the study History of other disease, metabolic dysfunction, physical examination finding, or clinical laboratory finding giving reasonable suspicion of a condition that contraindicated the use of the IMP or that might affect interpretation of the results of the study or renders the patient at high risk for treatment complications in the opinion of the investigator For females of childbearing potential, a positive blood pregnancy test Lactating female Use of systemic corticosteroids within 1 month prior to Day 1

Any known hypersensitivity to active comparator, fluorescein, any ingredient of the formulation used, dilating eye drops, or any anesthetics and microbial drops used Any other restriction accorded to the use of the active comparator Any treatment with an IMP in the 3 months prior to Day 1

Length of Study

The total duration of the study was up to 40 weeks (from screening through study completion) for each enrolled patient as follows:

Screening: up to 4 weeks

Baseline: Day 1

Study treatment administration period: from Day 1 to Week 20

Observational period: From Week 20 up to Week 36

Safety follow up call: During the observational period and 7 days after ranibizumab administration End of Study The end of the study was defined as the date when the last patient last observation (LPLO) occurs. LPLO was expected to occur 36 weeks after the last patient is enrolled.

Efficacy and Pharmacodynamic Outcome Measures

The primary analysis population was treatment naïve patients. Additional analyses may be performed in the overall population and in patients previously treated with IVT anti-VEGF.

The primary efficacy outcome measure for this study was the mean change in BCVA (ETDRS letters) from baseline at Week 24 in treatment-naïve patients.

Anatomic Outcome Measures by SD-OCT:

Mean change from baseline in foveal center point thickness at Week 24

Mean change from baseline in mean CST (1 mm diameter) at Week 24

Proportion of patients with resolution of subretinal and intraretinal fluid at Week 24

Anatomic outcome measures by fundus fluorescein angiography (FFA)

Proportion of patients with resolution of leakage at the macula at Week 24

Change from baseline in the size of the foveal avascular zone at Week 24

Exploratory Outcome Measures

The exploratory outcome measures for this study included but were not limited to the following:

BCVA:

Difference in mean BCVA change from baseline between the treatment-naïve patients and patients with previous IVT anti-VEGF (differential effect of RO6867461)

Durability-Related Exploratory Outcome Measures:

Time to increase of CST by >50 µm and/or loss of ≥5 letters of BCVA due to DME compared to values at Week 20

Time to retreatment with 0.3 mg ranibizumab after Week 20

Results

The primary efficacy analyses included all randomized patients, with patients grouped according to the treatment assigned at randomization.

The primary efficacy variable was the BCVA change from baseline to Week 24. The primary efficacy analysis was performed using a Mixed Model for Repeated Measurement (MMRM) model.

Best Corrected Visual Acuity

BCVA at a starting test distance of 4 meters was measured prior to dilating eyes by a trained and certified VA examiner masked to study drug arm assignment.

BCVA was measured by using the set of three Precision Vision™ or Lighthouse distance acuity charts (modified ETDRS Charts 1, 2, and R). A VA Manual was provided to the investigators. VA examiner and VA examination room certifications were obtained before any VA examinations were performed.

The BCVA examiner was masked to study eye and treatment assignment and will only perform the refraction and BCVA assessment (e.g. Visual Acuity Specification Manual). The BCVA examiner has also been masked to the BCVA letter scores of a patient's previous visits and only knew the patient's refraction data from previous visits. The BCVA examiner was not allowed to perform any other tasks involving direct patient care.

TABLE

| | | | | |
|---|---|---|---|---|
| Baseline Ocular Characteristics in the Study Eye Summary of Baseline Ocular Characteristics in Interest in the Study Eye, All Patients, Treatment Naïve Patients Protocol: BP30099 | | | | |
| | 0.3 mg Ranibizumab (N = 59) | 1.5 mg RO6867461 (N = 54) | 6 mg RO6867461 (N = 55) | All Patients (N = 168) |
| Best Corrected Visual Acuity result | | | | |
| n | 58 | 54 | 53 | 165 |
| Mean (SD) | 61.24 (9.87) | 60.94 (11.11) | 60.15 (10.80) | 60.79 (10.53) |
| Median | 64.00 | 63.50 | 63.0 | 63.00 |
| Min-Max | 33.0-73.0 | 35.0-85.0 | 25.0-73.0 | 25.0-85.0 |
| Best Corrected Visual Acuity Category | | | | |
| n | 58 | 54 | 53 | 165 |
| 20/40 or better | 13 (22.4%) | 15 (27.8%) | 11 (20.8%) | 39 (23.6%) |
| 20/200 or worse | 4 (6.9%) | 3 (5.6%) | 3 (5.7%) | 10 (6.1%) |
| Better than 20/200 but worse than 20/40 | 41 (70.7%) | 36 (66.7%) | 39 (73.6%) | 116 (70.3%) |
| Baseline BCVA 20/40 or better/worse than 20/40 | | | | |
| n | 58 | 54 | 53 | 165 |
| Worse than 20/40 | 45 (77.6%) | 39 (72.2%) | 42 (79.2%) | 126 (76.4%) |
| 20/40 or better | 13 (22.4%) | 15 (27.8%) | 11 (20.8%) | 39 (23.6%) |
| Baseline BCVA 20/200 or worse/better than 20/200 | | | | |
| n | 58 | 54 | 53 | 165 |
| Better than 20/200 | 54 (93.1%) | 51 (94.4%) | 50 (94.3%) | 155 (93.9%) |
| 20/200 or worse | 4 (6.9%) | 3 (5.6%) | 3 (5.7%) | 10 (6.1%) |
| Central Subfield Thickness | | | | |
| n | 58 | 54 | 53 | 165 |
| Mean (SD) | 490.88 (139.01) | 535.44 (163.13) | 495.57 (132.70) | 506.97 (145.95) |
| Median | 476.00 | 489.00 | 466.00 | 478.00 |
| Min-Max | 316.0-999.0 | 302.0-1000.0 | 234.0-825.0 | 234.0-1000.0 |

Primary Efficacy Outcome Measure is shown in FIG. 1. The FIG. 1 displays the primary efficacy endpoint: BCVA change from Baseline over Time to Week 24 for so far treatment naive patients. VA2 refers to the bispecific anti-VEGF/ANG2 antibody RO6867461 comprising the amino acid sequences of SEQ ID NO: 17, of SEQ ID NO: 18, of SEQ ID NO: 19, and of SEQ ID NO: 20 (administered intravitreally with a 6.0 mg or 1.5 mg dose), RBZ refers to ranibizumab (Lucentis®) (administered intravitreally with a 0.3 mg dose).

Central Subfield Thickness (CST) Change from Baseline (Study Eye)

Figure 2:
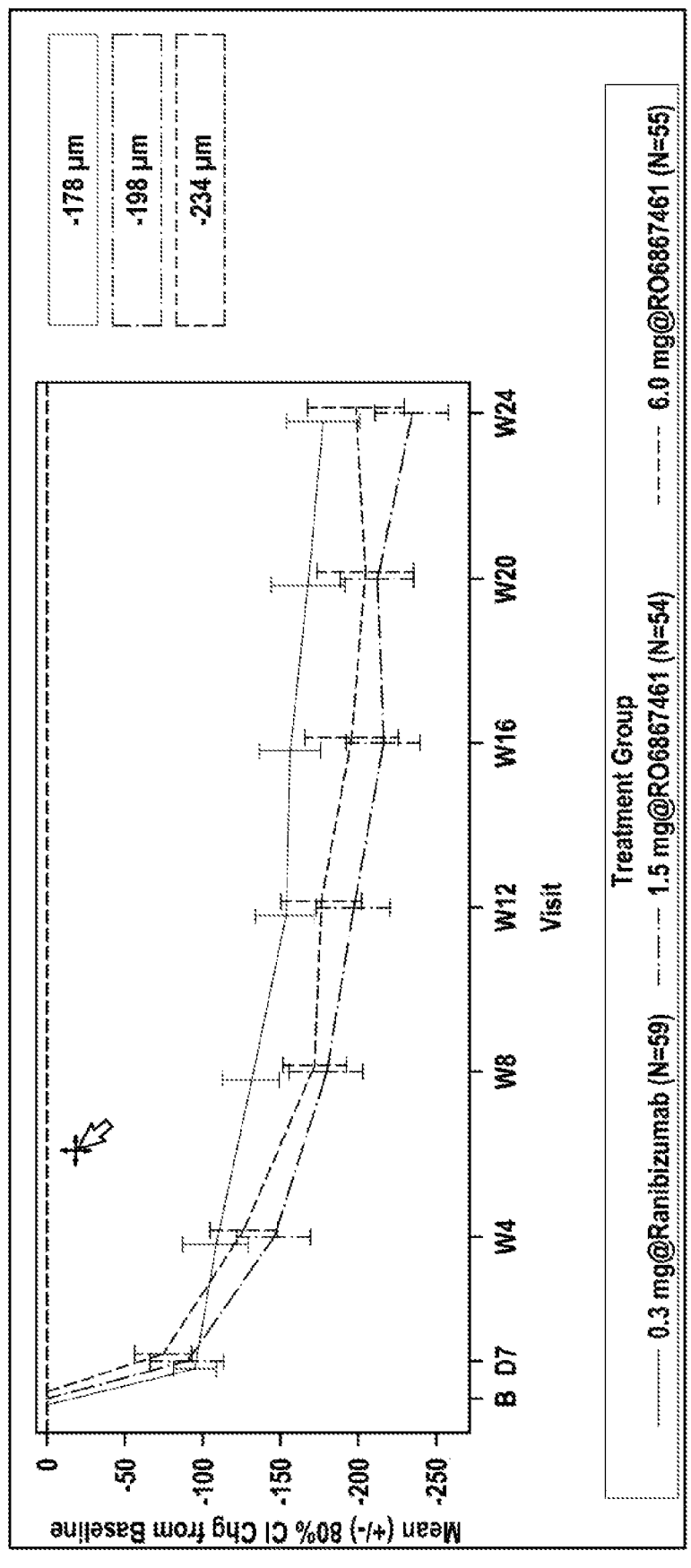
FIG. 2: CST, central subfield thickness measured by SD OCT. CST change of DME patients treated from Baseline over Time to Week 24 (treatment naive patients). The bispecific anti-VEGF/ANG2 antibody RO6867461 comprising the amino acid sequences of SEQ ID NO: 17, of SEQ ID NO: 18, of SEQ ID NO: 19, and of SEQ ID NO: 20 (administered intravitreally with a 6.0 mg or 1.5 mg dose), was compared to ranibizumab (Lucentis®) ((administered intravitreally with a 0.3 mg dose)).

A key secondary endpoint was the change from baseline in CST, central subfield thickness. Results are shown in FIG. 2. The bispecific anti-VEGF/ANG2 antibody RO6867461 comprising the amino acid sequences of SEQ ID NO: 17, of SEQ ID NO: 18, of SEQ ID NO: 19, and of SEQ ID NO: 20 (administered intravitreally with a 6.0 mg or 1.5 mg dose), was compared to ranibizumab (Lucentis®) (administered intravitreally with a 0.3 mg dose). This secondary anatomical endpoint directionally supports BCVA primary outcome.

Durability/Time to Retreatment

Criteria for Treatment with Ranibizumab During Observational Period

At each visit following the last dose of study treatment (week 20 visit), BCVA was assessed and SD-OCT imaging was performed (except for week 26 visit).

BCVA and CST values obtained at week 24 were compared to those obtained at visit week 20. BCVA and CST values obtained at weeks 28, 32 and 36 were compared to those of week 24.

If the patient met both of the following criteria the patient received a single dose of 0.3 mg ranibizumab and exited the study:

CST increased by ≥50 μm,

BCVA decreased by ≥5 letters due to DME

Figure 3:
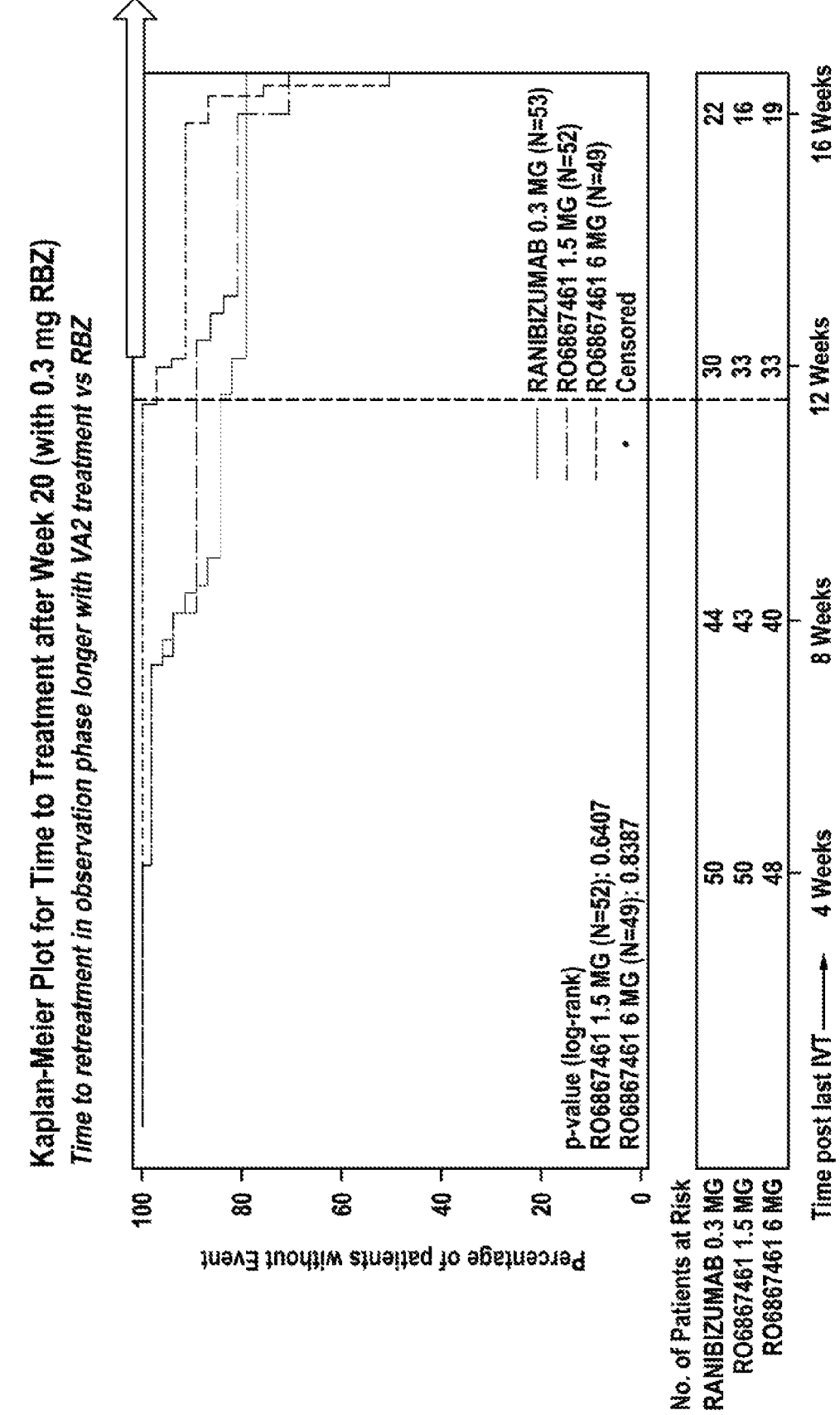
FIG. 3: Time to necessary retreatment based on disease activity assessed by both: BCVA decreased by ≥5 letters and CST increased by ≥50 μm (after dosing has discontinued (after 20 weeks or 6 monthly doses=Time post last intravitreal (IVT) administration). The bispecific anti-VEGF/ANG2 antibody RO6867461 comprising the amino acid sequences of SEQ ID NO: 17, of SEQ ID NO: 18, of SEQ ID NO: 19, and of SEQ ID NO: 20 (administered intravitreally with a 6.0 mg or 1.5 mg dose), was compared to ranibizumab (Lucentis®) ((administered intravitreally with a 0.3 mg dose)).

Results are shown in FIG. 3: FIG. 3 shows the time to retreatment after dosing has discontinued (after 20 weeks or 6 monthly doses=Time post last intravitreal (IVT) administration) based on disease activity assessed by both: BCVA decreased by ≥5 letters and CST increased by ≥50 μm. The bispecific anti-VEGF/ANG2 antibody RO6867461 comprising the amino acid sequences of SEQ ID NO: 17, of SEQ ID NO: 18, of SEQ ID NO: 19, and of SEQ ID NO: 20 (administered intravitreally with a 6.0 mg or 1.5 mg dose), was compared to ranibizumab (Lucentis®) (administered intravitreally with a 0.3 mg dose).

Figure 4:
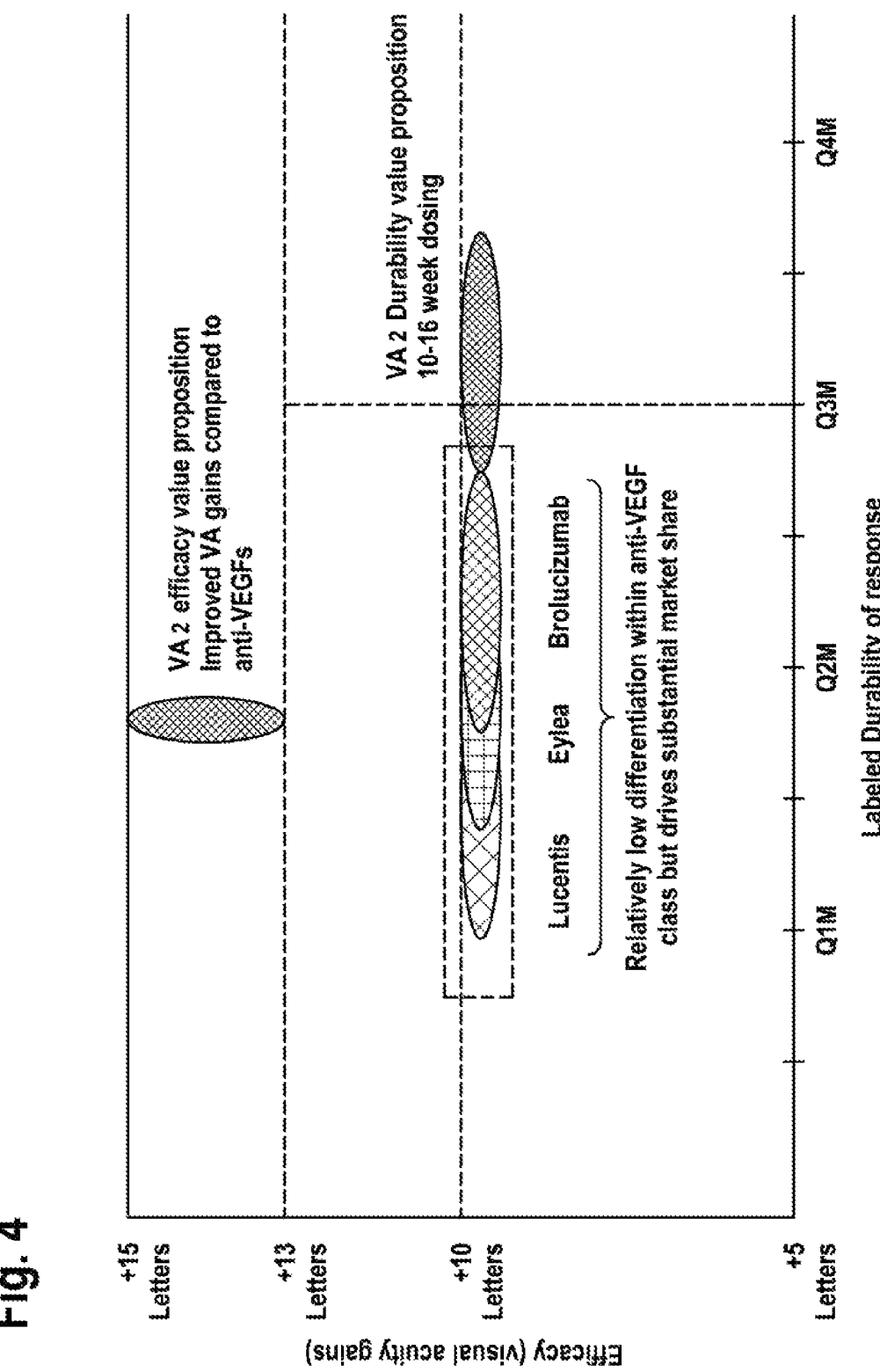
FIG. 4: Schematic comparison to other treatment options of DME based on published results (Compared agents Lucentis® (ranibizumab), Eylea® (aflibercept), brolucizumab and VA2 (RO6867461/RG7716).

For overview FIG. 4 represents a schematic comparison to other treatment options of DME based on published results (The following agents are compared Lucentis® (ranibizumab), Eylea® (aflibercept), brolucizumab and VA2 (RO6867461/RG7716).

Example 1B: Efficacy and Durability of Treatment of Patients Suffering from Diabetic Macular Edema (DME)

In a further study analogous to the above described study under Example 1A, patients suffering from DME (e.g center-involving diabetic macular edema (CI-DME)). are treated with the bispecific antibody that binds to human VEGF and human ANG2 comprising the amino acid sequences of SEQ ID NO: 17, of SEQ ID NO: 18, of SEQ ID NO: 19, and of SEQ ID NO: 20. As active comparator in treatment e.g. aflibercept and/or ranibizumab and/or brolicuzimab will be used. Patients include anti-VEGF treatment-naïve patients (have not been previously treated with anti-VEGF monotherapy with e.g. e.g. aflibercept and/or ranibizumab and/or brolicuzimab)) and also a group of patients which have been previously treated with anti-VEGF monotherapy. Designations of the respective bispecific antibody that binds to human VEGF and human ANG2 are RO6867461 or RG7716. Vials of sterile, colorless to brownish, preservative-free solution of RO6867461 for IVT administration of either 1.5 mg or 6 mg dose are used.

One or more of the following dosing schedules are used:

a) patients suffering from DME will be treated with a fixed Q8W dosing schedule following treatment initiation (e.g. 6 initial monthly injections)

b) patients suffering from DME will be treated with a fixed Q12W dosing (in one schedule with one cycle of Q8W dosing first), following treatment initiation (e.g. 6 initial monthly injections)

c) patients suffering from DME will be treated following treatment initiation (e.g. with 3-7 initial monthly injections) with a dosing regimen that extends the injection interval in stable absence of disease, or shortens the interval if there is disease activity. Such regimen includes e.g. that patient receive Q4W/Q8W/Q12W/Q16W dosing, dependent on their disease state The disease stability assessment would be based on best-corrected visual acuity (BCVA) and on CST as well as retinal thickness based on Optical coherence tomography (OCT). Outcome measure and results will be evaluated as described e.g. in Example 1A. Primary endpoints will be between 45 and 60 weeks.

In one embodiment patients suffering from DME are treatment naïve (have not been previously treated with anti-VEGF monotherapy with e.g. aflibercept and/or ranibizumab and/or brolicuzimab)

In one embodiment patients suffering from DME have been previously treated with anti-VEGF monotherapy with e.g. aflibercept and/or ranibizumab and/or brolicuzimab.

In one embodiment patients suffering from DME will be treated with a fixed Q8W dosing schedule following treatment initiation (e.g. 6 initial monthly injections).

In one embodiment patients suffering from DME will be treated with a fixed Q12W dosing (in one embodiment with one cycle of Q8W dosing first), following treatment initiation (e.g. 6 initial monthly injections).

In one embodiment patients suffering from DME will be treated following treatment initiation (e.g. with 3-7 initial monthly injections) with a dosing regimen that extends the injection interval in stable absence of disease, or shortens the interval if there is disease activity. In one embodiment such regimen includes that patient receive Q4w/Q8w/Q12w/Q16w dosing, dependent on their disease state.

In one embodiment patients suffering from AMD will be treated following treatment initiation (e.g. with 3-4 initial monthly injections) with a dosing regimen that extends the injection interval in stable absence of disease, or shortens the interval if there is disease activity. In one embodiment such regimen includes that patient receive Q4W/Q8W/Q12W/Q16W dosing, dependent on their disease state.

Example 2A: Efficacy and Durability of Treatment of Patients Suffering from Age-Related Macular Degeneration (AMD)

Objectives and Endpoints

This study has evaluated the efficacy, safety, and pharmacokinetics of RO6867461 administered at 12- and 16-week intervals in patients with neovascular age-related macular degeneration (nAMD). RO6867461 is a bispecific antibody that binds to human VEGF and human ANG2 comprising the amino acid sequences of SEQ ID NO: 17, of SEQ ID NO: 18, of SEQ ID NO: 19, and of SEQ ID NO: 20 (this antibody VEGFang2-0016 and its production is also described in detail in WO2014/009465 which is incorporated by reference). Designations of this bispecific anti-VEGF/ANG2 antibody herein are RO6867461 or RG7716 or VEGFang2-0016 or faricimab.

Specific objectives and corresponding endpoints for the study are outlined below.

Objectives and Corresponding Endpoints

Primary Efficacy Objective

To evaluate the efficacy of RO6867461 on visual acuity when administered at 12- and 16-week intervals
Corresponding Endpoint
Mean change from baseline BCVA at Week 40 using the ETDRS-like charts Secondary Efficacy Objectives 1) To evaluate the efficacy of RO6867461 on additional visual acuity outcomes Corresponding Endpoints
Mean change from baseline BCVA over time using the ETDRS-like charts
Proportion of patients gaining ≥15, ≥10, ≥5, or ≥0 letters from baseline BCVA over time
Proportion of patients avoiding loss of ≥15, ≥10, ≥5, or ≥0 letters from baseline BCVA over time
Proportion of patients with BCVA of 20/40 or better over time
Proportion of patients with BCVA of 20/200 or worse over time
2) To evaluate the efficacy of RO6867461 on anatomic outcome measures using SD-OCT
Corresponding Endpoints
Mean change from baseline in CFT over time
Mean change from baseline in mean CST (1 mm diameter) over time
Proportion of patients with intraretinal fluid, subretinal fluid, cysts, or pigment epithelial detachment over time
3) To evaluate the efficacy of RO6867461 on anatomic outcome measures using FFA
Corresponding Endpoints
Mean change from baseline in total area of CNV at Week 40 and Week 52
Mean change from baseline in total area of CNV component at Week 40 and Week 52
Mean change from baseline in total area of leakage at Week 40 and Week 52
Exploratory Efficacy Objective
To investigate the incidence of disease activity at Week 24
Corresponding Endpoints
Proportion of patients with disease activity at Week 24
Safety Objective
To evaluate the safety of multiple IVT doses of RO6867461 at 12- and 16-week intervals
Corresponding Endpoints
Incidence and severity of ocular adverse events
Incidence and severity of non-ocular adverse events
Other safety data, including but not limited to, reasons for withdrawal from study, laboratory data, concomitant medications, vital signs, and physical examination results will be listed and summarized descriptively Exploratory Pharmacokinetic/Pharmacodynamic Objectives 1) To assess the systemic PK profile of RO6867461

Corresponding Endpoints

Plasma concentration of RO6867461 at specified time-points

2) To evaluate the RO6867461, ranibizumab, free VEGF-A, and Ang-2 profile in aqueous humor Relationship between aqueous humor RO6867461 concentrations or PK parameters and free VEGF-A and Ang-2 concentrations Corresponding Endpoints Relationship between aqueous humor ranibizumab concentrations or PK parameters and free VEGF-A and Ang-2 concentrations Time course of free VEGF-A and Ang-2 concentrations in aqueous humor Immunogenicity Objective To investigate the formation of plasma anti-RO6867461 antibodies Corresponding Endpoints Incidence of ADAs during the study Exploratory Biomarker Objective To explore levels of potential biomarkers of angiogenesis and inflammation in aqueous humor at baseline and at additional timepoints to assess their response to RO6867461

Corresponding Endpoints

Relationship between aqueous humor concentration of potential biomarkers with primary and secondary endpoints Abbreviations Used Above:

ADA=anti-drug antibody; Ang-2=angiopoietin-2; BCVA=best corrected visual acuity; CFT=central foveal thickness; CNV=choroidal neovascularization; CST=central subfield thickness; ETDRS=Early Treatment Diabetic Retinopathy Study; FFA=fundus fluorescein angiography; IVT=intravitreal; PK=pharmacokinetic; SD-OCT=spectral domain optical coherence tomography; VEGF-A=vascular endothelial growth factor A.

Figure 5:
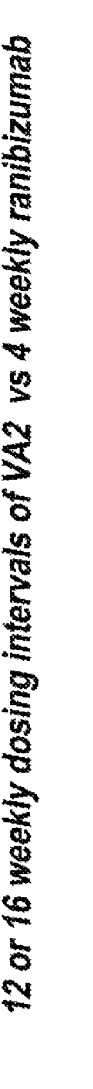
FIG. 5: Overview of the study design for the evaluation of the bispecific antibody RO6867461 administered at 12- and 16-week intervals in patients with neovascular age-related macular degeneration (nAMD).
Figure 5:
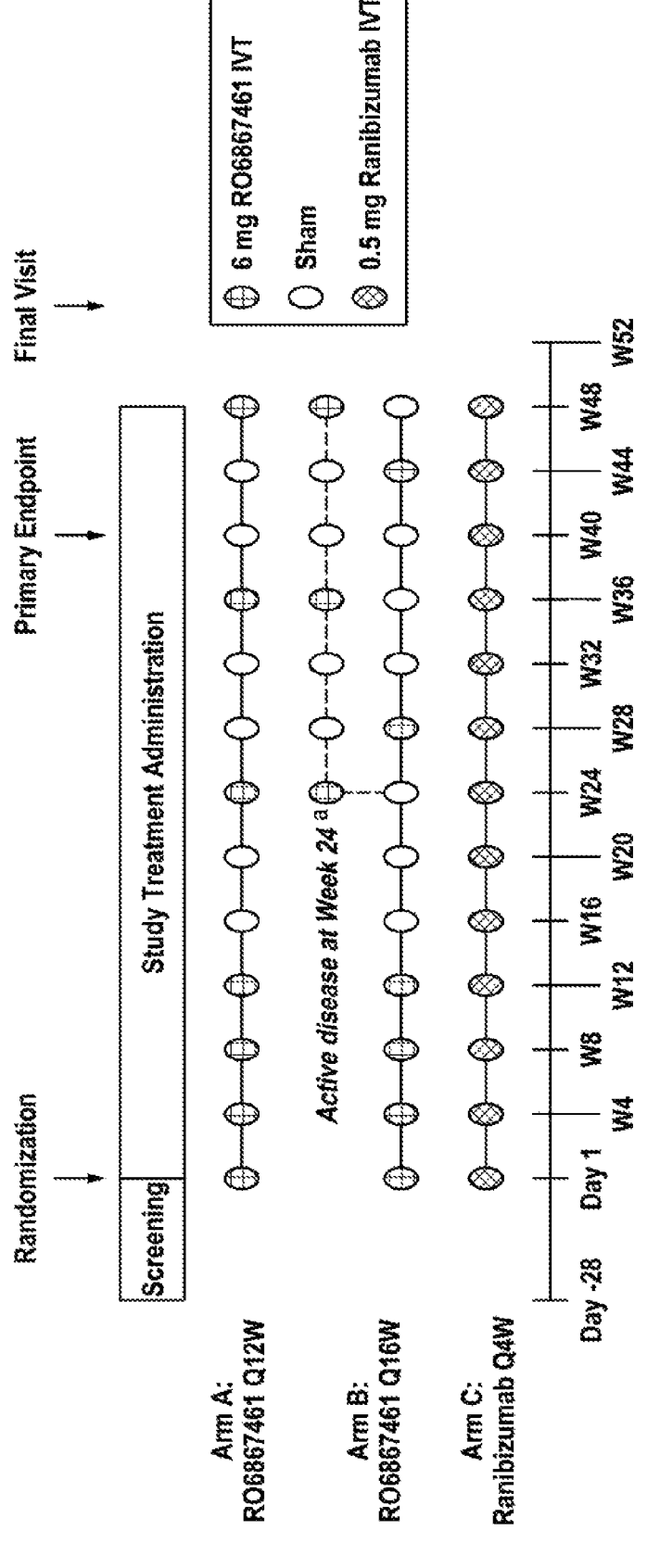

Study Design (FIG. 5 Presents an Overview of the Study Design)

Description of Study

This was a Phase II, multicenter, randomized, active comparator-controlled, subject and outcome assessor masked, parallel group, 52-week study to investigate the efficacy, safety, and pharmacokinetics of RO6867461 administered at 12- and 16-week intervals in treatment-naive patients with nAMD.

Approximately 75 patients were enrolled and randomized in a 2:2:1 ratio to one of three treatment arms:

Arm A (Q12W): 6 mg RO6867461 intravitreally (IVT) every 4 weeks up to Week 12 (4 injections), followed by 6 mg RO6867461 IVT every 12 weeks up to Week 48 (injections at Weeks 24, 36, and 48; 3 injections)

Arm B (Q16W): 6 mg RO6867461 IVT every 4 weeks up to Week 12 (4 injections), followed by 6 mg RO6867461 IVT every 16 weeks up to Week 48 (injections at Weeks 28 and 44; 2 injections) A protocol-defined assessment of disease activity at Week 24 requires Arm B patients with active disease (see criteria below) to switch to a 12-weekly dosing regimen of 6 mg RO6867461 for the remainder of the study, with injections commencing at Week 24 and repeated at Weeks 36 and 48.

Arm C (comparator arm): 0.5 mg ranibizumab IVT every 4 weeks for 48 weeks (13 injections) Only one eye will be chosen as the study eye. The total duration of the study for each patient will be up to 56 weeks, divided as follows:

Screening: up to 4 weeks prior to or on the same day as randomization

Randomization: Day 1

Study Treatment Administration: from Day 1 to Week 48

Final Visit: Week 52

Patients have undergone a screening examination within 4 weeks of study treatment administration. The screening and Week 1/Day 1 (randomization) visit may have occurred as a combined visit if all assessments (with the exception of informed consent) were completed within 48 hours. During screening (or the combined screening/Day 1 visit), the patient's eligibility was assessed, including a central review of fundus photography (FP), spectral domain optical coherence tomography (SD-OCT), and fundus fluorescein angiography (FFA) to ensure that CNV secondary to AMD meets the predefined ocular criteria in the study. Patients who were deemed ineligible based on screening results for any of the following reasons were allowed to be re-screened:

Uncontrolled blood pressure

Administrative reason (e.g., unable to schedule Day 1 within 28 days from the screening visit)

Not meeting eligibility criteria for the study eye (in the event the patient might be eligible to participate for the second eye after the initial screening period)

At re-screening, all screening visit assessments were performed (except for FFA imaging collection), provided the Central Reading Center-eligible FFA images were taken within 4 weeks before the new Day 1 visit (randomization).

On Day 1, eligible patients received their first IVT administration of either RO6867461 or ranibizumab according to the randomization schedule described above and following established standard administration procedures. Patients returned to the eye clinic 7 days after their first IVT administration and then every 4 weeks for study treatment administration and assessments as outlined in the schedule of activities in the protocol. Sham IVT administration was delivered to patients randomized to Arms A and B to maintain masking throughout the study period.

All patients were assessed for disease activity at Week 24. Patients randomized to Arm B who had active disease at Week 24 (see criteria below) switched to the Q12W dosing regimen of 6 mg RO6867461 for the remainder of the study, with injections commencing at Week 24 and repeated at Weeks 36 and 48.

Determination of active disease was made if any of the following criteria were met:

Increase in central subfield thickness (CST of >50 μm on Spectralis® OCT compared to average CST over last 2 visits (Weeks 16 and 20)

Or

Increase in CST of ≥75 μm compared to lowest CST recorded at either Week 16 or Week 20

Or

Decrease of at least 5 letters of best corrected visual acuity (BCVA) compared with average BCVA over last 2 visits (Weeks 16 and 20) due to nAMD disease activity Or Decrease of ≥10 letters of BCVA compared to highest BCVA recorded at either Week 16 or Week 20 due to nAMD disease activity Or Presence of new macular hemorrhage due to nAMD activity Patients will return for a final visit at Week 52. After the final visit, adverse events should be followed up as outlined in the protocol. Assessments performed in case of an unscheduled visit(s) are at the discretion of the investigator Number of Patients: Approximately 75 treatment-naive patients with nAMD were expected to be enrolled and randomized in this study in the United States.

Target Population

Inclusion Criteria

Patients met the following criteria for study entry: Ocular Criteria for Study Eye Treatment-naive CNV secondary to AMD (nAMD)

Subfoveal CNV or juxtafoveal CNV with a subfoveal component related to the CNV activity by FFA or SD-OCT (as evidenced by subretinal fluid, subretinal hyper-reflective material, evidence of leakage, or hemorrhage)

CNV lesion of all types (predominantly classic, minimally classic, or occult) with: Total lesion size (including blood, atrophy, fibrosis, and neovascularization) of ≤6 disc areas by FFA And CNV component area of ≥50% of total lesion size by FFA And Active CNV confirmed by FFA (evidence of leakage) And CNV exudation confirmed by SD-OCT (presence of fluid)

Clear ocular media and adequate pupillary dilatation to allow acquisition of good quality retinal images to confirm diagnosis General Criteria Signed Informed Consent Form Age≥50 years on Day 1

Ability to comply with the study protocol, in the investigator's judgment

For women of childbearing potential: agreement to remain abstinent (refrain from heterosexual intercourse) or use a contraceptive method with a failure rate of <1% per year during the treatment period and for at least 28 days after the last dose of study treatment Patients must be willing not to participate in any other clinical trial including an investigational medicinal product (IMP) or device up to completion of the current study Exclusion Criteria Patients who met any of the following criteria were excluded from study entry:

Ocular Criteria for Study Eye

CNV due to causes other than AMD, such as ocular histoplasmosis, trauma, pathological myopia, angioid streaks, choroidal rupture, or uveitis Central serous chorioretinopathy at screening Retinal pigment epithelial tear involving the macula On FFA Subretinal hemorrhage of >50% of the total lesion area and/or that involves the fovea Fibrosis or atrophy of >50% of the total lesion area and/or that involves the fovea Any prior or concomitant treatment for CNV including (but not restricted to) IVT treatment (steroids, antivascular endothelial growth factor [VEGF], tissue plasminogen activator, ocriplasmin, C3F8 gas, air), periocular pharmacological intervention, argon LASER photocoagulation, verteporfin photodynamic therapy, diode laser, transpupillary thermotherapy, or surgical intervention•Cataract surgery within 3 months of baseline assessments (Day 1)

Any other intraocular surgery (pars plana vitrectomy, glaucoma surgery, corneal transplant, radiotherapy)

Prior IVT treatment (including anti-VEGF medication) except for management of cataract complication with steroid IVT treatment•Prior periocular pharmacological intervention for other retinal diseases Concurrent Ocular Conditions Any concurrent intraocular condition in the study eye (e.g., amblyopia, aphakia, retinal detachment, cataract, diabetic retinopathy or maculopathy, or epiretinal membrane with traction) that, in the opinion of the investigator, could either reduce the potential for visual improvement or require medical or surgical intervention during the course of the study Active intraocular inflammation (grade trace or above) in the study eye on Day 1 (prior to randomization)•BCVA letter score of 73 to 24 letters (inclusive) on Early Treatment Diabetic Retinopathy Study (ETDRS)-like charts (20/40 to 20/320 Snellen equivalent) on Day 1

Current vitreous hemorrhage in the study eye

Uncontrolled glaucoma (e.g., progressive loss of visual fields or defined as intraocular pressure [IOP]≥25 mmHg despite treatment with anti-glaucoma medication) in the study eye Spherical equivalent of refractive error demonstrating more than 8 diopters of myopia in the study eye History of idiopathic or autoimmune-associated uveitis in either eye Active infectious conjunctivitis, keratitis, scleritis, or endophthalmitis in either eye on Day 1 (prior to randomization) General Criteria Any major illness or major surgical procedure within 1 month before screening Uncontrolled blood pressure ([BP] defined as systolic>180 mmHg and/or diastolic>100 mmHg while patient at rest). If a patient's initial reading exceeds these values, a second reading may be taken later on the same day, or on another day during the screening period. If the patient's BP is controlled by antihypertensive medication, the patient should be taking the same medication continuously for at least 30 days prior to Day 1.

Stroke or myocardial infarction within 3 months prior to Day 1

History of other disease, metabolic dysfunction, physical examination finding, or clinical laboratory findings giving reasonable suspicion of a condition that contraindicated the use of the investigational drug or that might affect interpretation of the results of the study or renders the patient at high risk for treatment complications in the opinion of the investigator Pregnant or breastfeeding, or intending to become pregnant during the study Women of childbearing potential must have a negative urine pregnancy test result within 28 days prior to initiation of study treatment. If the urine pregnancy test is positive, it must be confirmed by a serum pregnancy test.

Known hypersensitivity to ranibizumab, fluorescein, any ingredients of the formulation used, dilating eye drops, or any of the anesthetic and antimicrobial drops used Treatment with investigational therapy within 3 months prior to initiation of study treatment End of Study The end of the study was defined as the date when the last patient last visit (LPLV) occurs. LPLV was expected to occur 52 weeks after the last patient is enrolled.

Length of Study

The total length of the study, from screening of the first patient to the end of the study, was expected to be approximately 18-19 months.

Investigational Medicinal Products Test Product

RO6867461 Drug Product (120 mg/mL) was provided as a sterile, colorless to brownish liquid and contains no preservatives. Vials of sterile, colorless to brownish, preservative-free solution of RO6867461 for IVT administration of 6 mg dose every were used. The concentration of the bispecific antibody was about 120 mg/ml.

Dosage and Administration,

RO6867461, Ranibizumab, and Sham

Patients were given a 50-µL IVT injection of RO6867461 or ranibizumab into the study eye, or a sham administration, according to the randomization schedule as described below Arm A (Q12W): 6 mg RO6867461 IVT every 4 weeks up to Week 12 (4 injections), followed by 6 mg RO6867461 IVT every 12 weeks up to Week 48 (injections at Weeks 24, 36, and 48; 3 injections)

Arm B (Q16W): 6 mg RO6867461 IVT every 4 weeks up to Week 12 (4 injections), followed by 6 mg RO6867461 IVT every 16 weeks up to Week 48 (injections at Weeks 28 and 44; 2 injections)

Arm C (comparator arm): 0.5 mg ranibizumab IVT every 4 weeks for 48 weeks (13 injections)

Only one eye was chosen as the study eye.

Study Assessments

At timepoints when several assessments coincide, the following sequence was suggested, at the discretion of the investigator. The order could be adjusted to optimize site personnel and patient's time management, except where explicitly stated as mandatory (i.e., text in italics):

Vital signs

Blood sampling: At visits where FFA is performed, blood sampling and angiography can be performed from the same venous cannula. Blood samples must be collected before angiography.

Ocular assessments and imaging

BCVA: BCVA must have been conducted before pupil dilation. At screening and Day 1 visits, BCVA could be performed before vital signs and blood sampling to avoid unnecessary investigations in those patients who may be a screen failure as a result of BCVA letter score.

Slitlamp examination

Pupil dilation

SD-OCT

FP (+infrared reflectance)

FFA

Dilated binocular indirect high-magnification ophthalmoscopy

IOP: mandatory to be performed after all imaging assessments, and the same method should be used throughout the study period Aqueous humor sampling (optional)

Disease-Specific Assessments

Unless otherwise noted in schedule of activities (Appendix 1), all ocular assessments were performed for both eyes.

Best Corrected Visual Acuity

BCVA at a starting test distance of 4 meters was measured prior to dilating eyes by a trained and certified visual acuity (VA) examiner masked to study eye treatment assignment.

BCVA was measured using the set of three Precision Vision™ or Lighthouse distance acuity charts (modified ETDRS Charts 1, 2, and R). A VA Procedure Manual was provided to the investigators. VA examiner and VA examination room certifications were obtained before any VA examinations were performed.

The BCVA examiner was masked to the study eye and treatment assignment and will perform the refraction and BCVA assessments (e.g., VA Specification Manual). The BCVA examiner was also masked to the BCVA letter scores of a patient's previous visits and may only know patient refraction data from previous visits.

Additional Ocular Assessments

Additional ocular assessments which were performed during the study include the following:

Slitlamp examination (scales for grading flare/cells and vitreous hemorrhage density are detailed in Appendix 2)

Dilated binocular indirect high-magnification ophthalmoscopy

IOP

The method of IOP measurement used for a patient remained consistent throughout the study. IOP measurement of both eyes were performed after all imaging.

At study treatment visits, IOP pressure was conducted prior to study treatment administration and 30 (±15) minutes post-treatment administration in the study eye, and if IOP≥30 mmHg, IOP should be re-assessed 30 (±15) minutes later. If IOP continued to be elevated, treatment was undertaken at the discretion of the investigator.

Finger count vision assessment

In the study eye, a post-treatment optic nerve head perfusion was assessed for each patient immediately after study treatment administration (maximum within 15 minutes after treatment administration) by testing finger count vision, hand motion, or light perception as appropriate.

Ocular Imaging

The Central Reading Center provided sites with the Central Reading Center Manual and training materials for study-mandated ocular imaging. Before study images were obtained, site personnel and imaging systems (where applicable) was certified by the reading center as specified in the Central Reading Center Manual. All study subject ocular images were obtained only by trained and Central Reading Center certified personnel on certified/registered equipment at the study sites. A copy of all study subject ocular images were transferred to the central reading center for storage and for independent analysis, including for confirmation of eligibility of defined image-related criteria.

Week 24 Assessment of Disease Activity

All patients were assessed for disease activity at Week 24. Patients randomized to Arm B who had active disease at Week 24 (see criteria below) switched to the Q12W dosing regimen of 6 mg RO6867461 for the remainder of the study, with injections commencing at Week 24 and repeated at Weeks 36 and 48.

Determination of active disease was made if any of the following criteria are met:

Increase in CST of >50 µm on Spectralis OCT compared to average CST over last 2 visits (Weeks 16 and 20)

Or

Increase in CST of ≥75 µm compared to lowest CST recorded at either Week 16 or Week 20

Or

Decrease of at least 5 letters of BCVA compared with average BCVA over last 2 visits (Weeks 16 and 20), due to nAMD disease activity Or Decrease of ≥10 letters of BCVA compared to highest BCVA recorded at either Week 16 or Week 20 due to nAMD disease activity Or Presence of new macular hemorrhage due to nAMD activity Results Best Corrected Visual Acuity (BCVA) and Durability of BCVA Gains (Time to Retreatment to Maintain BCVA Gain)

Figure 6:
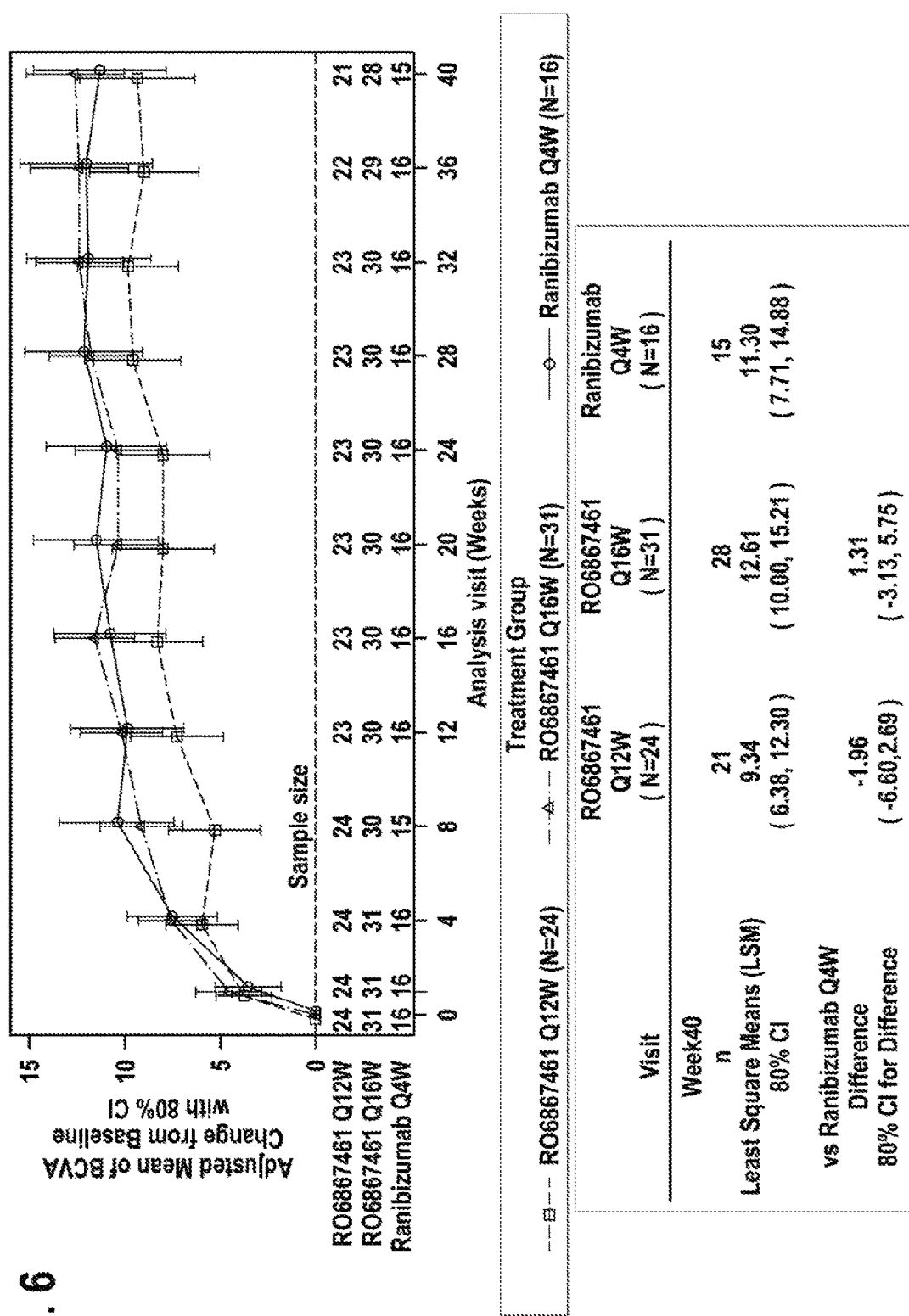
FIG. 6: BCVA gains from baseline of patients with neovascular age-related macular degeneration (nAMD) comparing the bispecific antibody RO6867461 (comprising the amino acid sequences of SEQ ID NO: 17, of SEQ ID NO: 18, of SEQ ID NO: 19, and of SEQ ID NO: 20 (administered intravitreally with a 6.0 mg) at 12- and 16-week intervals and ranibizumab (Lucentis®) ((administered intravitreally with a 0.3 mg dose)) at 4-week intervals.

Primary Efficacy Outcome Measure is shown in FIG. 6. The FIG. 6 displays the primary efficacy endpoint: BCVA change from Baseline over Time to Week 40. RO6867461 refers to the bispecific anti-VEGF/ANG2 antibody RO6867461 comprising the amino acid sequences of SEQ ID NO: 17, of SEQ ID NO: 18, of SEQ ID NO: 19, and of SEQ ID NO: 20 (administered intravitreally with a 6.0 mg dose either Q12W or Q16W), ranibizumab (Lucentis®) was administered intravitreally with a 0.3 mg dose Q4W. The initial BCVA gains were fully maintained for the RO6867461 Q12W or Q16W groups and in a similar range as the ranibizumab (Lucentis®) Q4W group.

Central Subfield Thickness (CST) Change from Baseline (Study Eye)

Figure 7:
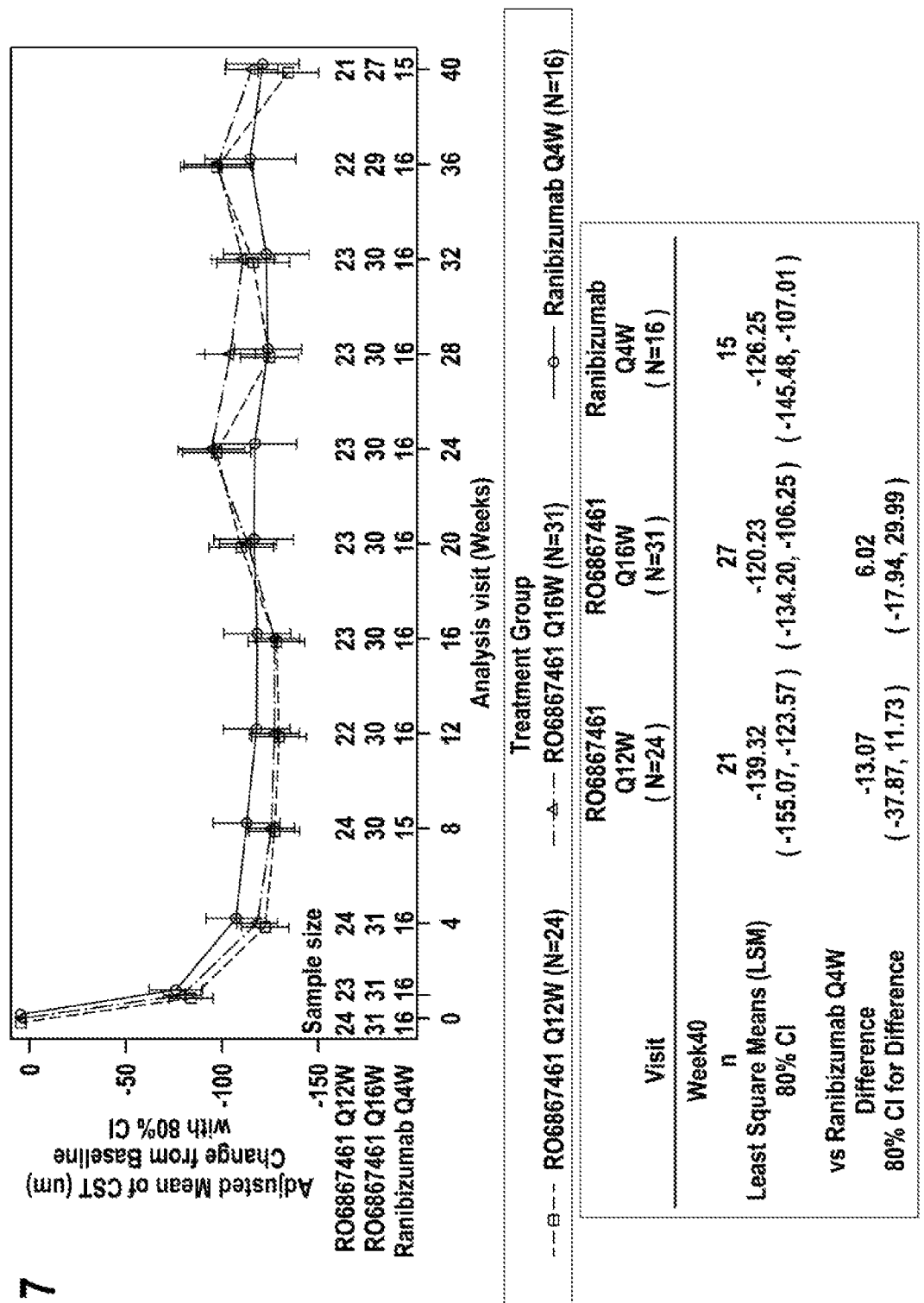
FIG. 7: Change from baseline CST (measured via OCT) of patients with neovascular age-related macular degeneration (nAMD) comparing the bispecific antibody RO6867461 (comprising the amino acid sequences of SEQ ID NO: 17, of SEQ ID NO: 18, of SEQ ID NO: 19, and of SEQ ID NO: 20 (administered intravitreally with a 6.0 mg) at 12- and 16-week intervals and ranibizumab (Lucentis®) ((administered intravitreally with a 0.3 mg dose)) at 4-week intervals.

A key secondary endpoint was the change from baseline in CST, central subfield thickness. Results are shown in FIG. 7. The bispecific anti-VEGF/ANG2 antibody RO6867461 comprising the amino acid sequences of SEQ ID NO: 17, of SEQ ID NO: 18, of SEQ ID NO: 19, and of SEQ ID NO: 20 (administered intravitreally with a 6.0 mg dose either Q12W or Q16W), was compared to ranibizumab (Lucentis®) (administered intravitreally with a 0.3 mg dose Q4W). This secondary anatomical endpoint directionally supports BCVA primary outcome There were grater reductions in CST with bispecific anti-VEGF/ANG2 antibody RO6867461 during treatment initiation than with ranibizumab.

Example 2B: Efficacy and Durability of Treatment of Patients Suffering from Age-Related Macular Degeneration (AMD)

In a further study analogous to the above described study under Example 2A, patients suffering from AMD (e.g. wet age-related macular degeneration (wAMD), especially neovascular AMD) are treated with the bispecific antibody that binds to human VEGF and human ANG2 comprising the amino acid sequences of SEQ ID NO: 17, of SEQ ID NO: 18, of SEQ ID NO: 19, and of SEQ ID NO: 20. As active comparator in treatment e.g aflibercept and/or ranibizumab and/or brolicuzimab will be used. Patients include anti-VEGF treatment-naïve patients (have not been previously treated with anti-VEGF monotherapy with e.g. aflibercept and/or ranibizumab and/or brolicuzimab) and also a group of patients which have been previously treated with anti-VEGF monotherapy with e.g. aflibercept and/or ranibizumab and/or brolicuzimab. Designations of the respective bispecific antibody that binds to human VEGF and human ANG2 are RO6867461 or RG7716. Vials of sterile, colorless to brownish, preservative-free solution of RO6867461 for IVT administration of either 1.5 mg or 6 mg dose are used.

E.g. the following dosing schedules is used:

Patients suffering from AMD will be treated following treatment initiation (e.g. with 3-7 initial monthly injections) with a dosing regimen that extends the injection interval in stable absence of disease, or shortens the interval if there is disease activity. Such regimen includes e.g. that patient receive Q4W/Q8W/Q12W/Q16W dosing, dependent on their disease state The disease stability assessment would be based on best-corrected visual acuity (BCVA) and on CST as well as retinal thickness based on Optical coherence tomography (OCT). Outcome measure and results will be evaluated as described e.g. in Example 1A. Primary endpoints will be between 45 and 60 weeks.

Example 3

Binding to of the anti-VEGF/ANG2 antibody to VEGF, Ang2, FcgammaR and FcRn

VEGF isoforms kinetic affinity including assessment of species-crossreactivity

Around 12000 resonance units (RU) of the capturing system (10 µg/ml goat anti human F(ab)'$_2$; Order Code: 28958325; GE Healthcare Bio-Sciences AB, Sweden) were coupled on a CM5 chip (GE Healthcare BR-1005-30) at pH 5.0 by using an amine coupling kit supplied by the GE Healthcare. The sample and system buffer was PBS-T (10 mM phosphate buffered saline including 0.05% Tween® 20) pH 7.4. The flow cell was set to 25° C.—and the sample block set to 12° C.—and primed with running buffer twice. The bispecific antibody was captured by injecting a 50 nM solution for 30 sec at a flow of 5 µl/min. Association was measured by injection of human hVEGF121, mouse mVEGF120 or rat rVEGF164 in various concentrations in solution for 300 sec at a flow of 30 µl/min starting with 300 nM in 1:3 dilutions. The dissociation phase was monitored for up to 1200 sec and triggered by switching from the sample solution to running buffer. The surface was regenerated by 60 sec washing with a Glycine pH 2.1 solution at a flow rate of 30 µl/min. Bulk refractive index differences were corrected by subtracting the response obtained from a goat anti human F(ab')$_2$ surface. Blank injections are also subtracted (=double referencing). For calculation of apparent $K_D$ and other kinetic parameters the Langmuir 1:1 model was used. Results are shown in Table 5.

Ang2 Solution Affinity Including Assessment of Species-Crossreactivity

Solution affinity measures the affinity of an interaction by determining the concentration of free interaction partners in an equilibrium mixture. The solution affinity assay involves the mixing of an <VEGF-ANG-2> bispecific antibody, kept at a constant concentration, with a ligand (=Ang2) at varying concentrations. Maximum possible resonance units (e.g. 17000 resonance units (RU)) of an antibody was immobilized on the CM5 chip (GE Healthcare BR-1005-30) surface at pH 5.0 using an amine coupling kit supplied by the GE Healthcare. The sample and system buffer was HBS-P pH 7.4. Flow cell was set to 25° C. and sample block to 12° C. and primed with running buffer twice. To generate a calibration curve increasing concentrations of Ang2 were injected into a BIAcore™ flowcell containing the immobilized VEGF-ANG-2> bispecific antibody. The amount of bound Ang2 was determined as resonance units (RU) and plotted against the concentration. Solutions of each ligand (11 concentrations from 0 to 200 nM for the VEGF-ANG-2> bispecific antibody) were incubated with 10 nM Ang2 and allowed to reach equilibrium at room temperature. Free Ang2 concentrations were determined from calibration curve generated before and after measuring the response of solutions with known amounts of Ang2. A 4-parameter fit was set with XLfit4 (IDBS Software) using Model 201 using free Ang2 concentration as y-axis and used concentration of antibody for inhibition as x-axis. The affinity was calculated by determining the inflection point of this curve. The surface was regenerated by one time 30 sec washing with a 0.85% H$_3$PO$_4$ solution at a flow rate of 30 µl/min. Bulk refractive index differences were corrected by subtracting the response obtained from a blank-coupled surface. Results are shown in Table 6.

FcRn Steady State Affinity

For FcRn measurement a steady state affinity was used to compare bispecific antibodies against each other. Human FcRn was diluted into coupling buffer (10 µg/ml, Na-Acetate pH5.0) and immobilized on a C1-Chip (GE Healthcare BR-1005-35) by targeted immobilization procedure using a BIAcore™ wizard to a final response of 200 RU. Flow cell was set to 25° C. and sample block to 12° C. and primed with running buffer twice. The sample and system buffer was PBS-T (10 mM phosphate buffered saline including 0.05% Tween® 20) pH 6.0. To assess different IgG concentrations for each antibody, a concentration of 62.5 nM, 125 nM and 250 nM, 500 nM was prepared. Flow rate was set to 30 µl/min and the different samples were injected consecutively onto the chip surface choosing 180 sec association time. The surface was regenerated by injected PBS-T pH 8 for 60 sec at a flow rate of 30 µl/min. Bulk refractive index differences were corrected by subtracting the response obtained from a blank surface. Buffer injections are also subtracted (=double referencing). For calculation of steady state affinity the method from the Bia-Evaluation software was used. Briefly, the RU values (RU max) were plotted against the analysed concentrations, yielding a dose-response curve. Based on a 2-parametric fit, the upper asymptote is calculated, allowing the determination of the half-maximal RU value and hence the affinity. Results are shown in FIG. 5 and Table 7. Analogously the affinity to cyno, mouse and rabbit FcRn can be determined.

FcgammaRIIIa Measurement

For FcgammaRIIIa measurement a direct binding assay was used. Around 3000 resonance units (RU) of the capturing system (1 µg/ml Penta-His; Qiagen) were coupled on a CM5 chip (GE Healthcare BR-1005-30) at pH 5.0 by using an amine coupling kit supplied by the GE Healthcare. The sample and system buffer was HBS-P+ pH 7.4. The flow cell was set to 25° C.—and sample block to 12° C.—and primed with running buffer twice. The FcgammaRIIIa-His-receptor was captured by injecting a 100 nM solution for 60 sec at a flow of 5 µl/min. Binding was measured by injection of 100 nM of bispecific antibody or monospecific control antibodies (anti-Dig for IgG1 subclass and an IgG4 subclass antibody) for 180 sec at a flow of 30 µl/. The surface was regenerated by 120 sec washing with Glycine pH 2.5 solution at a flow rate of 30 µl/min. Because FcgammaRIIIa binding differs from the Langmuir 1:1 model, only binding/no binding was determined with this assay. In a similar manner FcgammaRIa, and FcgammaRIIa binding can be determined. Results are shown in FIG. 6, where it follows that by introduction of the mutations P329G LALA no more binding to FcgammaRIIIa could be detected.

Assessment of Independent VEGF- and Ang2-Binding to the <VEGF-ANG-2> Bispecific Antibodies Around 3500 resonance units (RU) of the capturing system (10 µg/ml goat anti human IgG; GE Healthcare Bio-Sciences AB, Sweden) were coupled on a CM4 chip (GE Healthcare BR-1005-34) at pH 5.0 by using an amine coupling kit supplied by the GE Healthcare. The sample and system buffer was PBS-T (10 mM phosphate buffered saline including 0.05% Tween® 20) pH 7.4. The temperature of the flow cell was set to 25° C. and of the sample block to 12° C. Before capturing, the flow cell was primed with running buffer twice.

The bispecific antibody was captured by injecting a 10 nM solution for 60 sec at a flow of 5 µl/min. Independent binding of each ligand to the bispecific antibody was analysed by determining the active binding capacity for each ligand, either added sequentially or simultaneously (flow of 30 µl/min):

1. Injection of human VEGF with a concentration of 200 nM for 180 sec (identifies the single binding of the antigen).
2. Injection of human Ang2 with a concentration of 100 nM for 180 sec (identifies single binding of the antigen).
3. Injection of human VEGF with a concentration of 200 nM for 180 sec followed by an additional injection of human Ang2 with a concentration of 100 nM for 180 sec (identifies binding of Ang2 in the presence of VEGF).
4. Injection of human Ang2 with a concentration of 100 nM for 180 sec followed by an additional injection of human VEGF with a concentration of 200 nM (identifies binding of VEGF in the presence of Ang2).
5. Co-Injection of human VEGF with a concentration of 200 nM and of human Ang2 with a concentration of 100 nM for 180 sec (identifies the binding of VEGF and of Ang2 at the same time).

The surface was regenerated by 60 sec washing with a 3 mM MgCl2 solution at a flow rate of 30 µl/min. Bulk refractive index differences were corrected by subtracting the response obtained from a goat anti human IgG surface.

The bispecific antibody is able to bind both antigens mutual independently if the resulting final signal of the approaches 3, 4 & 5 equals or is similar to the sum of the individual final signals of the approaches 1 and 2. Results are shown in the Table below, where VEGFang2-0016 (=RO6867461), is shown to be able to bind mutual independently to VEGF and ANG2

Assessment of Simultaneous VEGF- and Ang2-Binding to the <VEGF-ANG-2> Bispecific Antibodies First, around 1600 resonance units (RU) of VEGF (20 µg/ml) were coupled on a CM4 chip (GE Healthcare BR-1005-34) at pH 5.0 by using an amine coupling kit supplied by the GE Healthcare. The sample and system buffer was PBS-T (10 mM phosphate buffered saline including 0.05% Tween® 20) pH 7.4. Flow cell was set to 25° C. and sample block to 12° C. and primed with running buffer twice. Second, 50 nM solution of the bispecific antibody was injected for 180 sec at a flow of 30 µl/min. Third, hAng-2 was injected for 180 sec at a flow of 30 µl/min. The binding response of hAng-2 depends from the amount of the bispecific antibody bound to VEGF and shows simultaneous binding. The surface was regenerated by 60 sec washing with a 0.85% H3PO4 solution at a flow rate of 30 µl/min. Simultaneous binding is shown by an additional specific binding signal of hAng2 to the previous VEGF bound <VEGF-ANG-2> bispecific antibodies.

TABLE

| Results: Kinetic affinities to VEGF isoforms from different species | |
| --- | --- |
| | VEGFang2-0016-apparent affinity |
| Human VEGF 121 | ≤1 pM (out of Biacore specification) |
| mouseVEGF 120 | no binding |
| Rat VEGF 164 | 14 nM |

TABLE

| Results: Solution affinities to Ang2 | |
| --- | --- |
| | VEGFang2-0016 KD [nM] |
| humanAng2 | 20 |
| cynoAng2 | 13 |
| mouseAng2 | 13 |
| rabbitAng2 | 11 |

TABLE

| Results: Affinity to FcRn of <VEGF-ANG-2> bispecific antibodies | |
| --- | --- |
| | VEGFang2-0016 [affinity] |
| Human FcRn | no binding |
| Cyno FcRn | no binding |
| Mouse FcRn | no binding |

TABLE

| Results Binding to FcgammaRI-IIIa | |
| --- | --- |
| | VEGFang2-0016 |
| FcγRIa | No binding |
| FcγRIIa | No binding |
| FcγRIIIa | No binding |

TABLE

| Results: Independent binding of VEGF- and Ang2 to <VEGF-ANG-2> bispecific antibodies | | | | | |
| --- | --- | --- | --- | --- | --- |
| | 1) Ang2 [RUmax] | 2) VEGF [RUmax] | 3) first VEGF then Ang2 [RUmax] | 4) first Ang2 then VEGF [RUmax] | 5) Coinjection Ang2 + VEGF [RUmax] |
| VEGFang2-0016 | 174 | 50 | 211 | 211 | 211 |

The invention claimed is:

1. A method of treating a patient suffering from an ocular vascular disease, the method comprising:
administering to the patient an effective amount of a bispecific antibody which binds to human vascular endothelial growth factor (VEGF) and to human angiopoietin-2 (ANG-2), and comprises the amino acid sequences of SEQ ID NO: 17, of SEQ ID NO: 18, of SEQ ID NO: 19, and of SEQ ID NO: 20,
wherein the bispecific antibody is administered intravitreally every 8 weeks or less frequently following a treatment initiation comprising 3 to 7 monthly administrations, in a dose of about 5 to 7 mg,
wherein the ocular vascular disease is Age-Related Macular Degeneration (AMD).

2. The method according to claim 1, wherein AMD is neovascular (wet) AMD (nAMD).

3. The method according to claim 1, wherein the bispecific antibody is administered every 10 to 12 weeks.

4. The method according to claim 1, wherein the bispecific antibody is administered every 11 to 13 weeks.

5. The method according to claim 1, wherein the bispecific antibody is administered every 12 to 14 weeks.

6. The method according to claim 1, wherein the bispecific antibody is administered every 13 to 15 weeks.

7. The method according to claim 1, wherein the bispecific antibody is administered every 14 to 16 weeks.

8. The method according to claim 1, wherein the bispecific antibody is administered in a dose of about 6 mg.

9. The method according to claim 8, wherein the bispecific antibody is administered at a concentration of about 120 mg/ml.

10. The method according to claim 1, wherein the patient has not been previously treated with an anti-VEGF treatment.

11. The method according to claim 1, wherein the patient has been previously treated with an anti-VEGF treatment.

12. The method according to claim 1, wherein the treatment initiation comprises 4 to 6 monthly administrations.

13. The method according to claim 12, wherein administration following the treatment initiation comprises a dosing schedule that extends the administration interval in stable absence of disease, or shortens the interval if there is disease activity.

14. The method according to claim 13 wherein such dosing schedule includes that the patient receives Q8W or Q12W or Q16W dosing.

15. The method according to claim 13, wherein the stable absence of disease is determined as:

Central Subfield Thickness (CST) increased by <50 μm; and/or

Best Corrected Visual Acuity (BCVA/ETDRS) decreased by <5 letters and the disease activity is determined as Central Subfield Thickness (CST) increased by ≥50 μm; and/or Best Corrected Visual Acuity (BCVA/ETDRS) decreased by ≥5 letters.

16. The method according to claim 13 wherein such dosing schedule includes that the patient receives Q8W dosing.

17. The method according to claim 13 wherein such dosing schedule includes that the patient receives Q12W dosing.

18. The method according to claim 13 wherein such dosing schedule includes that the patient receives Q16W dosing.

19. The method according to claim 1, wherein the effective amount of the bispecific antibody prolongs the time to retreatment and/or prolongs the time to loss of visual acuity and, wherein the retreatment with the bispecific antibody is administered in presence of a disease activity which is determined as:

Central Subfield Thickness (CST) increase by ≥50 μm; and/or

Best Corrected Visual Acuity (BCVA/ETDRS) decrease by ≥5 letters.

* * * * *

SEQUENCE LISTING

```
Sequence total quantity: 27
SEQ ID NO: 1              moltype = AA   length = 14
FEATURE                   Location/Qualifiers
REGION                    1..14
                          note = heavy chain CDR3H, ranibizumab
                          note = heavy chain CDR3H, ranibizumab
source                    1..14
                          mol_type = protein
                          organism = synthetic construct
SEQUENCE: 1
YPYYYGTSHW YFDV                                                      14

SEQ ID NO: 2              moltype = AA   length = 17
FEATURE                   Location/Qualifiers
REGION                    1..17
                          note = heavy chain CDR2H, ranibizumab
source                    1..17
                          mol_type = protein
                          organism = synthetic construct
SEQUENCE: 2
WINTYTGEPT YAADFKR                                                   17

SEQ ID NO: 3              moltype = AA   length = 5
FEATURE                   Location/Qualifiers
REGION                    1..5
                          note = heavy chain CDR1H, ranibizumab
source                    1..5
                          mol_type = protein
                          organism = synthetic construct
SEQUENCE: 3
HYGMN                                                                5

SEQ ID NO: 4              moltype = AA   length = 9
FEATURE                   Location/Qualifiers
REGION                    1..9
                          note = light chain CDR3L,  ranibizumab
source                    1..9
                          mol_type = protein
                          organism = synthetic construct
SEQUENCE: 4
QQYSTVPWT                                                            9

SEQ ID NO: 5              moltype = AA   length = 7
FEATURE                   Location/Qualifiers
REGION                    1..7
                          note = light chain CDR2L,  ranibizumab
source                    1..7
                          mol_type = protein
                          organism = synthetic construct
```

```
SEQUENCE: 5
FTSSLHS                                                                  7

SEQ ID NO: 6            moltype = AA   length = 11
FEATURE                 Location/Qualifiers
REGION                  1..11
                        note = light chain CDR1L,  ranibizumab
source                  1..11
                        mol_type = protein
                        organism = synthetic construct
SEQUENCE: 6
SASQDISNYL N                                                             11

SEQ ID NO: 7            moltype = AA   length = 123
FEATURE                 Location/Qualifiers
REGION                  1..123
                        note = heavy chain variable domain VH,  ranibizumab
source                  1..123
                        mol_type = protein
                        organism = synthetic construct
SEQUENCE: 7
EVQLVESGGG LVQPGGSLRL SCAASGYDFT HYGMNWVRQA PGKGLEWVGW INTYTGEPTY  60
AADFKRRFTF SLDTSKSTAY LQMNSLRAED TAVYYCAKYP YYYGTSHWYF DVWGQGTLVT  120
VSS                                                                      123

SEQ ID NO: 8            moltype = AA   length = 107
FEATURE                 Location/Qualifiers
REGION                  1..107
                        note = light chain variable domain VL,  ranibizumab
source                  1..107
                        mol_type = protein
                        organism = synthetic construct
SEQUENCE: 8
DIQLTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIK                     107

SEQ ID NO: 9            moltype = AA   length = 20
FEATURE                 Location/Qualifiers
REGION                  1..20
                        note = heavy chain CDR3H,  Ang2i_LC10 variant
source                  1..20
                        mol_type = protein
                        organism = synthetic construct
SEQUENCE: 9
SPNPYYYDSS GYYYPGAFDI                                                    20

SEQ ID NO: 10           moltype = AA   length = 17
FEATURE                 Location/Qualifiers
REGION                  1..17
                        note = heavy chain CDR2H,  Ang2i_LC10 variant
source                  1..17
                        mol_type = protein
                        organism = synthetic construct
SEQUENCE: 10
WINPNSGGTN YAQKFQG                                                       17

SEQ ID NO: 11           moltype = AA   length = 5
FEATURE                 Location/Qualifiers
REGION                  1..5
                        note = heavy chain CDR1H,  Ang2i_LC10 variant
source                  1..5
                        mol_type = protein
                        organism = synthetic construct
SEQUENCE: 11
GYYMH                                                                    5

SEQ ID NO: 12           moltype = AA   length = 11
FEATURE                 Location/Qualifiers
REGION                  1..11
                        note = light chain CDR3L,  Ang2i_LC10 variant
source                  1..11
                        mol_type = protein
                        organism = synthetic construct
SEQUENCE: 12
QVWDSSSDHW V                                                             11

SEQ ID NO: 13           moltype = AA   length = 7
FEATURE                 Location/Qualifiers
REGION                  1..7
```

-continued

```
                              note = light chain CDR2L,  Ang2i_LC10 variant
source                        1..7
                              mol_type = protein
                              organism = synthetic construct
SEQUENCE: 13
DDSDRPS                                                             7

SEQ ID NO: 14                 moltype = AA  length = 11
FEATURE                       Location/Qualifiers
REGION                        1..11
                              note = light chain CDR1L,  Ang2i_LC10 variant
source                        1..11
                              mol_type = protein
                              organism = synthetic construct
SEQUENCE: 14
GGNNIGSKSV H                                                        11

SEQ ID NO: 15                 moltype = AA  length = 129
FEATURE                       Location/Qualifiers
REGION                        1..129
                              note = heavy chain variable domain VH,  Ang2i_LC10
                               variant
source                        1..129
                              mol_type = protein
                              organism = synthetic construct
SEQUENCE: 15
QVQLVQSGAE VKKPGASVKV SCKASGYTFT GYYMHWVRQA PGQGLEWMGW INPNSGGTNY   60
AQKFQGRVTM TRDTSISTAY MELSRLRSDD TAVYYCARSP NPYYYDSSGY YYPGAFDIWG   120
QGTMVTVSS                                                           129

SEQ ID NO: 16                 moltype = AA  length = 110
FEATURE                       Location/Qualifiers
REGION                        1..110
                              note = light chain variable domain VL,  Ang2i_LC10
                               variant
source                        1..110
                              mol_type = protein
                              organism = synthetic construct
SEQUENCE: 16
SYVLTQPPSV SVAPGQTARI TCGGNNIGSK SVHWYQQKPG QAPVLVVYDD SDRPSGIPER   60
FSGSNSGNTA TLTISRVEAG DEADYYCQVW DSSSDHWVFG GGTKLTVLSS              110

SEQ ID NO: 17                 moltype = AA  length = 451
FEATURE                       Location/Qualifiers
REGION                        1..451
                              note = Heavy chain 1 of  CrossMAb IgG1 with
                               AAA mutations and P329G LALA mutations (VEGFang2-0016)
source                        1..451
                              mol_type = protein
                              organism = synthetic construct
SEQUENCE: 17
EVQLVESGGG LVQPGGSLRL SCAASGYDFT HYGMNWVRQA PGKGLEWVGW INTYTGEPTY   60
AADFKRRFTF SLDTSKSTAY LQMNSLRAED TAVYYCAKYP YYYGTSHWYF DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMAS RTPEVTCVVV DVSHEDPEVK FNWYVDGVEV HNAKTKPREE   300
QYNSTYRVVS VLTVLAQDWL NGKEYKCKVS NKALGAPIEK TISKAKGQPR EPQVYTLPPC   360
RDELTKNQVS LWCLVKGFYP SDIAVEWESN GQPENNYKTT PPVLDSDGSF FLYSKLTVDK   420
SRWQQGNVFS CSVMHEALHN AYTQKSLSLS P                                  451

SEQ ID NO: 18                 moltype = AA  length = 461
FEATURE                       Location/Qualifiers
REGION                        1..461
                              note = Heavy chain 2 of  CrossMAb IgG1 with
                               AAA mutations and P329G LALA mutations (VEGFang2-0016)
source                        1..461
                              mol_type = protein
                              organism = synthetic construct
SEQUENCE: 18
QVQLVQSGAE VKKPGASVKV SCKASGYTFT GYYMHWVRQA PGQGLEWMGW INPNSGGTNY   60
AQKFQGRVTM TRDTSISTAY MELSRLRSDD TAVYYCARSP NPYYYDSSGY YYPGAFDIWG   120
QGTMVTVSSA SVAAPSVFIF PPSDEQLKSG TASVVCLLNN FYPREAKVQW KVDNALQSGN   180
SQESVTEQDS KDSTYSLSST LTLSKADYEK HKVYACEVTH QGLSSPVTKS FNRGECDKTH   240
TCPPCPAPEA AGGPSVFLFP PKPKDTLMAS RTPEVTCVVV DVSHEDPEVK FNWYVDGVEV   300
HNAKTKPREE QYNSTYRVVS VLTVLAQDWL NGKEYKCKVS NKALGAPIEK TISKAKGQPR   360
EPQVCTLPPS RDELTKNQVS LSCAVKGFYP SDIAVEWESN GQPENNYKTT PPVLDSDGSF   420
FLVSKLTVDK SRWQQGNVFS CSVMHEALHN AYTQKSLSLS P                       461

SEQ ID NO: 19                 moltype = AA  length = 214
```

-continued

```
FEATURE              Location/Qualifiers
REGION               1..214
                     note = Light chain 1 of   CrossMAb IgG1 with
                      AAA mutations and P329G LALA mutations (VEGFang2-0016)
source               1..214
                     mol_type = protein
                     organism = synthetic construct
SEQUENCE: 19
DIQLTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 20          moltype = AA  length = 213
FEATURE              Location/Qualifiers
REGION               1..213
                     note = Light chain 2 of   CrossMAb IgG1 with
                      AAA mutations and P329G LALA mutations (VEGFang2-0016)
source               1..213
                     mol_type = protein
                     organism = synthetic construct
SEQUENCE: 20
SYVLTQPPSV SVAPGQTARI TCGGNNIGSK SVHWYQQKPG QAPVLVVYDD SDRPSGIPER  60
FSGSNSGNTA TLTISRVEAG DEADYYCQVW DSSSDHWVFG GGTKLTVLSS ASTKGPSVFP  120
LAPSSKSTSG GTAALGCLVK DYFPEPVTVS WNSGALTSGV HTFPAVLQSS GLYSLSSVVT  180
VPSSSLGTQT YICNVNHKPS NTKVDKKVEP KSC                              213

SEQ ID NO: 21          moltype = AA  length = 107
FEATURE              Location/Qualifiers
source               1..107
                     mol_type = protein
                     organism = Homo sapiens
SEQUENCE: 21
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC               107

SEQ ID NO: 22          moltype = AA  length = 105
FEATURE              Location/Qualifiers
source               1..105
                     mol_type = protein
                     organism = Homo sapiens
SEQUENCE: 22
QPKAAPSVTL FPPSSEELQA NKATLVCLIS DFYPGAVTVA WKADSSPVKA GVETTTPSKQ  60
SNNKYAASSY LSLTPEQWKS HRSYSCQVTH EGSTVEKTVA PTECS                 105

SEQ ID NO: 23          moltype = AA  length = 328
FEATURE              Location/Qualifiers
source               1..328
                     mol_type = protein
                     organism = Homo sapiens
SEQUENCE: 23
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSP                                     328

SEQ ID NO: 24          moltype = AA  length = 191
FEATURE              Location/Qualifiers
source               1..191
                     mol_type = protein
                     organism = Homo sapiens
SEQUENCE: 24
MNFLLSWVHW SLALLLYLHH AKWSQAAPMA EGGGQNHHEV VKFMDVYQRS YCHPIETLVD  60
IFQEYPDEIE YIFKPSCVPL MRCGGCCNDE GLECVPTEES NITMQIMRIK PHQGQHIGEM  120
SFLQHNKCEC RPKKDRARQE NPCGPCSERR KHLFVQDPQT CKCSCKNTDS RCKARQLELN  180
ERTCRCDKPR R                                                      191

SEQ ID NO: 25          moltype = AA  length = 496
FEATURE              Location/Qualifiers
source               1..496
                     mol_type = protein
                     organism = Homo sapiens
SEQUENCE: 25
MWQIVFFTLS CDLVLAAAYN NFRKSMDSIG KKQYQVQHGS CSYTFLLPEM DNCRSSSSPY  60
VSNAVQRDAP LEYDDSVQRL QVLENIMENN TQWLMKLENY IQDNMKKEMV EIQQNAVQNQ  120
TAVMIEIGTN LLNQTAEQTR KLTDVEAQVL NQTTRLELQL LEHSLSTNKL EKQILDQTSE  180
INKLQDKNSF LEKKVLAMED KHIIQLQSIK EEKDQLQVLV SKQNSIIEEL EKKIVTATVN  240
```

-continued

```
NSVLQKQQHD LMETVNNLLT MMSTSNSAKD PTVAKEEQIS FRDCAEVFKS GHTTNGIYTL   300
TFPNSTEEIK AYCDMEAGGG GWTIIQRRED GSVDFQRTWK EYKVGFGNPS GEYWLGNEFV   360
SQLTNQQRYV LKIHLKDWEG NEAYSLYEHF YLSSEELNYR IHLKGLTGTA GKISSISQPG   420
NDFSTKDGDN DKCICKCSQM LTGGWWFDAC GPSNLNGMYY PQRQNTNKFN GIKWYYWKGS   480
GYSLKATTMM IRPADF                                                   496

SEQ ID NO: 26           moltype = AA  length = 498
FEATURE                 Location/Qualifiers
source                  1..498
                        mol_type = protein
                        organism = Homo sapiens
SEQUENCE: 26
MTVFLSFAFL AAILTHIGCS NQRRSPENSG RRYNRIQHGQ CAYTFILPEH DGNCRESTTD   60
QYNTNALQRD APHVEPDFSS QKLQHLEHVM ENYTQWLQKL ENYIVENMKS EMAQIQQNAV   120
QNHTATMLEI GTSLLSQTAE QTRKLTDVET QVLNQTSRLE IQLLENSLST YKLEKQLLQQ   180
TNEILKIHEK NSLLEHKILE MEGKHKEELD TLKEEKENLQ GLVTRQTYII QELEKQLNRA   240
TTNNSVLQKQ QLELMDTVHN LVNLCTKEGV LLKGGKREEE KPFRDCADVY QAGFNKSGIY   300
TIYINNMPEP KKVFCNMDVN GGGWTVIQHR EDGSLDFQRG WKEYKMGFGN PSGEYWLGNE   360
FIFAITSQRQ YMLRIELMDW EGNRAYSQYD RFHIGNEKQN YRLYLKGHTG TAGKQSSLIL   420
HGADFSTKDA DNDNCMCKCA LMLTGGWWFD ACGPSNLNGM FYTAGQNHGK LNGIKWHYFK   480
GPSYSLRSTT MMIRPLDF                                                 498

SEQ ID NO: 27           moltype = AA  length = 1124
FEATURE                 Location/Qualifiers
source                  1..1124
                        mol_type = protein
                        organism = Homo sapiens
SEQUENCE: 27
MDSLASLVLC GVSLLLSGTV EGAMDLILIN SLPLVSDAET SLTCIASGWR PHEPITIGRD   60
FEALMNQHQD PLEVTQDVTR EWAKKVVWKR EKASKINGAY FCEGRVRGEA IRIRTMKMRQ   120
QASFLPATLT MTVDKGDNVN ISFKKVLIKE EDAVIYKNGS FIHSVPRHEV PDILEVHLPH   180
AQPQDAGVYS ARYIGGNLFT SAFTRLIVRR CEAQKWGPEC NHLCTACMNN GVCHEDTGEC   240
ICPPGFMGRT CEKACELHTF GRTCKERCSG QEGCKSYVFC LPDPYGCSCA TGWKGLQCNE   300
ACHPGFYGPD CKLRCSCNNG EMCDRFQGCL CSPGWQGLQC EREGIPRMTP KIVDLPDHIE   360
VNSGKFNPIC KASGWPLPTN EEMTLVKPDG TVLHPKDFNH TDHFSVAIFT IHRILPPDSG   420
VWVCSVNTVA GMVEKPFNIS VKVLPKPLNA PNVIDTGHNF AVINISSEPY FGDGPIKSKK   480
LLYKPVNHYE AWQHIQVTNE IVTLNYLEPR TEYELCVQLV RRGEGGEGHP GPVRRFTTAS   540
IGLPPPRGLN LLPKSQTTLN LTWQPIFPSS EDDFYVEVER RSVQKSDQQN IKVPGNLTSV   600
LLNNLHPREQ YVVRARVNTK AQGEWSEDLT AWTLSDILPP QPENIKISNI THSSAVISWT   660
ILDGYSISSI TIRYKVQGKN EDQHVDVKIK NATITQYQLK GLEPETAYQV DIFAENNIGS   720
SNPAFSHELV TLPESQAPAD LGGGKMLLIA ILGSAGMTCL TVLLAFLIIL QLKRANVQRR   780
MAQAFQNVRE EPAVQFNSGT LALNRKVKNN PDPTIYPVLD WNDIKFQDVI GEGNFGQVLK   840
ARIKKDGLRM DAAIKRMKEY ASKDDHRDFA GELEVLCKLG HHPNIINLLG ACEHRGYLYL   900
AIEYAPHGNL LDFLRKSRVL ETDPAFAIAN STASTLSSQQ LLHFAADVAR GMDYLSQKQF   960
IHRDLAARNI LVGENYVAKI ADFGLSRGQE VYVKKTMGRL PVRWMAIESL NYSVYTTNSD   1020
VWSYGVLLWE IVSLGGTPYC GMTCAELYEK LPQGYRLEKP LNCDDEVYDL MRQCWREKPY   1080
ERPSFAQILV SLNRMLEERK TYVNTTLYEK FTYAGIDCSA EEAA                   1124
```